(12) United States Patent
Berodier et al.

(10) Patent No.: US 11,254,611 B2
(45) Date of Patent: Feb. 22, 2022

(54) CEMENT PRODUCTION

(71) Applicant: GCP Applied Technologies Inc., Cambridge, MA (US)

(72) Inventors: Elise Berodier, Lausanne (CH); Nathan A. Tregger, Northborough, MA (US); Josephine H. Cheung, Lexington, MA (US); David F. Myers, Somerville, MA (US); Li Zhang, Acton, MA (US); Dorota Kazmierczak, Acton, MA (US); Lawrence R. Roberts, Acton, MA (US); Denise A. Silva, Los Alamitos, CA (US); Richard Sibbick, Northborough, MA (US); Jeffrey Thomas, Winchester, MA (US); Mark F. Roberts, North Andover, MA (US); Riccardo Stoppa, Milan (IT); Elizabeth Burns, Windham, NH (US)

(*) Notice: Subject to any disclaimer, the term of this patent is extended or adjusted under 35 U.S.C. 154(b) by 327 days.

(21) Appl. No.: 16/465,448

(22) PCT Filed: Dec. 20, 2018

(86) PCT No.: PCT/US2018/066665
§ 371 (c)(1),
(2) Date: May 30, 2019

(87) PCT Pub. No.: WO2020/091821
PCT Pub. Date: May 7, 2020

(65) Prior Publication Data
US 2021/0094876 A1    Apr. 1, 2021

Related U.S. Application Data

(60) Provisional application No. 62/755,102, filed on Nov. 2, 2018.

(51) Int. Cl.
*C04B 7/02* (2006.01)
*C04B 7/36* (2006.01)
(Continued)

(52) U.S. Cl.
CPC ............ *C04B 7/02* (2013.01); *B02C 17/1805* (2013.01); *B02C 17/1815* (2013.01);
(Continued)

(58) Field of Classification Search
CPC ............ G01N 21/3563; G01N 21/359; G01N 21/4788; G01N 33/383; C04B 7/52;
(Continued)

(56) References Cited

U.S. PATENT DOCUMENTS 3,632,018 A    5/1972  Ross
4,026,717 A    5/1977  Harris et al.
(Continued)

FOREIGN PATENT DOCUMENTS

EP    0463960    2/1992
EP    0974561    1/2000
(Continued)

OTHER PUBLICATIONS

Wallace, "The Benefit of NIR Spectroscopy in the Production of Polymers", Polymer Rheology Conference 2001, Paper 16, pp. 1-3. (Year: 2001).*
(Continued)

*Primary Examiner* — Dominic J Bologna
(74) *Attorney, Agent, or Firm* — Craig K. Leon

(57) ABSTRACT

The present invention provides a method and system for manufacturing cement wherein ground particles of cement and calcium sulfate are subjected to infrared sensors, laser sensors, or both, so that emanated, irradiated, transmitted, and/or absorbed energy having wavelengths principally within the range of 700 nanometers to 1 millimeter can be
(Continued)

monitored and compared to stored data previously obtained from ground cement and sulfate particles and preferably correlated with stored strength, calorimetric, or other data values, such that adjustments can be made to the mill processing conditions, such as the form or amounts of calcium sulfate (e.g., gypsum, plaster, anhydride), or cement additive levels. The strength and other properties of cement can be thus adjusted, and its quality can be more uniform.

27 Claims, 17 Drawing Sheets

(51) Int. Cl.
    *C04B 7/52*     (2006.01)
    *G01N 21/3563*     (2014.01)
    *G01N 21/359*     (2014.01)
    *G01N 21/47*     (2006.01)
    *G01N 33/38*     (2006.01)
    *B02C 23/22*     (2006.01)
    *B02C 25/00*     (2006.01)
    *B02C 17/18*     (2006.01)
    *C04B 103/00*     (2006.01)
    *C04B 103/12*     (2006.01)

(52) U.S. Cl.
    CPC .............. *B02C 23/22* (2013.01); *B02C 25/00* (2013.01); *C04B 7/362* (2013.01); *C04B 7/52* (2013.01); *G01N 21/359* (2013.01); *G01N 21/3563* (2013.01); *G01N 21/4788* (2013.01); *G01N 33/383* (2013.01); *C04B 2103/001* (2013.01); *C04B 2103/12* (2013.01); *Y02P 40/10* (2015.11); *Y02P 40/121* (2015.11)

(58) Field of Classification Search
    CPC ..... C04B 7/362; C04B 7/02; C04B 2103/001; C04B 2103/12
    See application file for complete search history.

(56) References Cited

U.S. PATENT DOCUMENTS

| | | | |
|---|---|---|---|
| 4,077,763 A | | 3/1978 | Jäger et al. |
| 4,081,285 A | * | 3/1978 | Pennell ............... C04B 7/43 106/740 |
| 4,229,560 A | | 10/1980 | Chernikhov et al. |
| 4,300,879 A | | 11/1981 | Goldmann et al. |
| 4,404,640 A | | 9/1983 | Dumbeck et al. |
| 4,498,930 A | | 2/1985 | Rake et al. |
| 4,582,992 A | | 4/1986 | Atwell et al. |
| 4,586,146 A | | 4/1986 | Dumbeck et al. |
| 4,635,858 A | | 1/1987 | Welch et al. |
| 4,749,273 A | | 6/1988 | Reinhold |
| 4,976,540 A | | 12/1990 | Kitamura et al. |
| 5,021,662 A | | 6/1991 | Johnson |
| 5,040,972 A | | 8/1991 | Kleinhenz et al. |
| 5,305,887 A | | 4/1994 | Krieg et al. |
| 5,339,751 A | | 8/1994 | Tutt |
| 5,475,220 A | | 12/1995 | Hughes et al. |
| 5,510,619 A | | 4/1996 | Zachmann et al. |
| 5,513,803 A | * | 5/1996 | Czekai ................ B02C 17/161 241/16 |
| 5,523,957 A | | 6/1996 | Perron et al. |
| 5,754,423 A | | 5/1998 | Teutenberg et al. |
| 5,882,190 A | | 3/1999 | Doumet |
| 5,888,256 A | | 3/1999 | Morrison |
| 5,975,891 A | | 11/1999 | Hundeb |
| 6,009,419 A | | 12/1999 | Coveney et al. |
| 6,050,813 A | | 4/2000 | Doumet |
| 6,142,771 A | | 11/2000 | Doumet |
| 6,183,244 B1 | | 2/2001 | Doumet |
| 6,221,151 B1 | * | 4/2001 | Campbell ............. C04B 22/143 106/772 |
| 6,362,477 B1 | | 3/2002 | Sowerby et al. |
| 6,383,283 B1 | | 5/2002 | Doumet |
| 6,668,201 B1 | | 12/2003 | Bonissone et al. |
| 6,790,034 B1 | | 9/2004 | Kearns et al. |
| 6,816,791 B2 | | 11/2004 | Myers et al. |
| 7,551,982 B2 | | 6/2009 | Hammerling |
| 7,924,414 B2 | | 4/2011 | Mound |
| 8,442,688 B2 | | 5/2013 | Loutfi |
| 8,868,242 B2 | | 10/2014 | Loutfi |
| 8,887,806 B2 | | 11/2014 | Iverson et al. |
| 9,679,244 B2 | | 6/2017 | Ohno et al. |
| 2003/0015663 A1 | | 1/2003 | Mikula et al. |
| 2003/0046130 A1 | | 3/2003 | Golightly et al. |
| 2003/0060993 A1 | | 3/2003 | Russell et al. |
| 2003/0236721 A1 | | 12/2003 | Plumer et al. |
| 2004/0021077 A1 | | 2/2004 | Ambuel |
| 2004/0021862 A1 | | 2/2004 | Panigrahi et al. |
| 2004/0232339 A1 | | 11/2004 | Lanoue |
| 2005/0132933 A1 | | 6/2005 | Blum |
| 2006/0287773 A1 | | 12/2006 | Andersen et al. |
| 2010/0329515 A1 | * | 12/2010 | Edgerton ........... G01N 21/3563 382/110 |
| 2011/0000401 A1 | * | 1/2011 | Stratton .................. C04B 28/02 106/712 |
| 2017/0363552 A1 | * | 12/2017 | Enders ..................... C04B 7/345 |
| 2019/0265162 A1 | * | 8/2019 | Fujiyama ................ G06T 7/001 |

FOREIGN PATENT DOCUMENTS

| | | |
|---|---|---|
| EP | 1862795 | 5/2006 |
| EP | 1382905 | 9/2007 |
| EP | 2640499 | 5/2012 |
| GB | 111193 | 6/1983 |
| WO | 9531710 | 11/1995 |
| WO | 9940419 | 8/1999 |
| WO | 9946584 | 9/1999 |
| WO | 9958959 | 11/1999 |
| WO | 0025115 | 5/2000 |
| WO | 0222246 | 3/2002 |
| WO | 0235213 | 5/2002 |
| WO | 03059852 | 7/2003 |
| WO | 03102574 | 11/2003 |
| WO | 2004101178 | 11/2004 |
| WO | 2004106874 | 12/2004 |
| WO | 2006054154 | 5/2006 |
| WO | 2007128832 | 11/2007 |
| WO | 2007128833 | 11/2007 |

OTHER PUBLICATIONS

Moessner, "Utility of near-infrared analyzers for real-time process control", Process Control and Quality, 2(1992) 237-247, Elsevier Science Publishers B.V. Amsterdam.

Walling & Dabney, "Process control of shampoo with near-infrared reflectance spectroscopy", Journal of the Society of Cosmetic Chemists, 39, 191-199 (May/Jun. 1988).

Cooper, "NIR Analysis for Process Control", Cereal Foods World 1983, pp. 241-245.

Wu et al., "Remote in-line monitoring of emulsion polymerization of styrene by short-wavelength near-infrared spectroscopy / Part I. Performance during normal runs", Process and Quality 8 (1996), 1-23.

Fontoura et al., "Monitoring and Control of Styrene Solution Polymerization Using NIR Spectroscopy", Journal of Applied Polymer Science, vol. 90, 1273-1289 (2003).

\* cited by examiner

CEMENT PRODUCTION

FIELD OF THE INVENTION

The invention relates to cement manufacturing; and, more particularly, it relates to monitoring and adjusting of calcium sulfate and cement additives in a cement grinding mill to optimize strength of the ground cement.

BACKGROUND OF THE INVENTION

Cement-based materials, such as concrete and mortar, are among the most widely used construction materials in the world, as they are necessary for making roads, bridges, tunnels, foundations, buildings, dams, and other infrastructure. The manufacture of cement and the study of its impact on cement hydration and material strength, however, involve heterogeneous factors that give rise to complex issues.

FIG. 1 illustrates a typical process whereby clinker is made and ground in a mill to provide cement, which is the binder material for concrete and mortar. Raw materials containing calcium, iron, silicon and aluminum (designated at 2), are crushed and blended (4), stored (6), optionally preheated (8), and fed into the kiln (10), where they are heated to very high temperatures (e.g., 1500° C.). Heating in the kiln is sufficient to fuse the raw materials into clinker "nodules" which are cooled or allowed to cool (12) and are optionally stored (14). The clinker nodules are added with a source of calcium sulfate (16) and fed into the cement mill (18) which grinds the materials to produce the finished cement (20).

Supplemental cementitious materials, such as fly ash, slag, other pozzolans, and/or limestone, may be added with the clinker before (at 16) or after the grinding mill stage (18). The produced cement is typically cooled and then tested (20), stored in silos (22) until being delivered to the customer (22), who uses the cement to make concrete, mortar, or other construction materials.

Typically, sulfate, in the form of gypsum, is added into the cement mill (18), where the clinker and gypsum are ground to a specific particle size (20). The resultant ground particles of clinker, and gypsum are commonly referred to as Portland cement. Blended cements are Portland cements combined with supplementary cementitious materials (e.g., fly ash) before or after the mill.

The manufacture of Portland cement generates a significant amount of carbon dioxide. This occurs especially during firing of the kiln (10) where calcination of the limestone occurs (releasing carbon dioxide). For each metric ton of cement produced, approximately 0.84 tons of carbon dioxide are released (See e.g., WBCSD Cement Sustainability Initiative reports). As annual production is about 4 billion metric tons of cement, this amount represents approximately 5% of all carbon dioxide generated by man-made processes. Reducing carbon dioxide is of great importance to sustainability initiatives in cement production.

It can be difficult to obtain consistent quality in cement products despite expensive process controls. Major reasons include high variability of the raw materials (due to their origin within a given quarry as well as across multiple quarries) and of processing conditions—such as kiln temperature, oxygen levels within the kiln, rate of cooling, and kiln fuel changes that can affect the interaction of chemical constituents as the clinker is formed.

The present inventors believe that improving control over cement hydration, despite numerous factors that fluctuate during manufacturing, such as aluminate content and sulfate availability, provides many benefits. They propose to implement monitoring and adjustment processes not currently used or envisioned today in the cement manufacturing field, so that greater consistency of cement product quality can be realized.

By focusing on consistency by accounting for the variation in clinker, sulfate and other materials introduced into the cement mill as well as the grinding process conditions, the present inventors believe that they can enhance the consistency of strength in the cement product, as well as reduce its large carbon footprint.

Furthermore, the inventors believe that the performance of cement additives can also benefit by accounting for variation in the clinker and other materials introduced into the cement mill as well as the grinding process conditions. Cement additives are chemical products used to improve the efficiency of cement grinding mills (grinding aids) and/or to improve the performance of mortars and concretes made with the cement (quality improvers). One such performance parameter is cement compressive strength. Cement additives are often used to increase the strength of the cement at one or more ages. FIG. 2 shows some typical response curves of compressive strengths obtained by using the testing methods described in EN-196-1:2016 on mortars as a function of two strength enhancing chemicals commonly used in cement additives. As can be seen, different cement additives have different optimum dosage requirements with respect to achieving optimum cement strength (in this case 1 day compressive strength). Typically, the dose of a cement additive is determined based on the production parameters of the mill (such as mill output) and quality parameters of the cement (such as fineness, residue in the "#325 sieve", powder flow, pack-set, set time, rheological behavior, and compressive strength). Most plants are equipped with flowmeters that allow accurate monitoring of the volume of cement additive being introduced in the mill. Cement additives can be used to further reduce the inconsistencies and to improve the quality of the cement. Knowledge of the variations can allow cement additives to be adjusted in type or amount, with a variety of goals including, but not limited to, maximizing strength, achieving a target early age strength without exceeding a later age maximum, increasing the use of supplementary cementitious materials, controlling set time or rheology, and other advantages. Thus, within a closed-loop framework, additives can be used to increase consistency of the final cement product.

Ground Portland cement is primarily composed of hydratable calcium silicates. The calcium silicates are essentially a mixture of tricalcium silicate (otherwise referred to as alite, $3CaO.SiO_2$, or "$C_3S$" in cement chemists' notation) and dicalcium silicate (otherwise referred to as belite, $2CaO.SiO_2$, or "$C_2S$") in which the former is the dominant form, with lesser amounts of tricalcium aluminate ($3CaO.Al_2O_3$, "$C_3A$") and tetracalcium aluminoferrite ($4CaO.Al_2O_3.Fe_2O_3$, "$C_4AF$"). See e.g., Dodson, Vance H., Concrete Admixtures (Van Nostrand Reinhold, New York N.Y. 1990), page 1.

In order to control the early calcium aluminate reaction, cement manufacturers typically add an amount of sulfate, often in the form of gypsum, to the cement clinker. It is the sulfate which, upon contact with water when mixed with cement (e.g., to make concrete or mortar), reacts with calcium aluminate to form a hydrated product called ettringite. This reaction consumes aluminates and thus lowers aluminum concentration in solution, which allows proper formation of the calcium silicate hydrates (C—S—H) and thereby confer strength to the concrete or mortar made from the cement.

The present inventors shall use calcium sulfate as an example of a "source of sulfate" which will be introduced into a grinding mill along with clinker to produce cement. Gypsum (i.e., calcium sulfate dihydrate) is a form of calcium sulfate that reacts readily with calcium aluminate in the cement during hydration. Other forms of calcium sulfate are "plaster" (e.g., calcium sulfate hemihydrate, or bassanite), and calcium sulfate anhydrite. Thus, gypsum is 1 mole of calcium sulfate associated with 2 moles of water ($Ca_2SO_4.2H_2O$); plaster is 1 mole of calcium sulfate associated with 0.5 moles of water ($Ca_2SO_4 \cdot \frac{1}{2}H_2O$); and anhydrite is calcium sulfate that is not associated with water ($Ca_2SO_4$).

The hemihydrate form of calcium sulfate (plaster) is also relied upon as a calcium sulfate source in the cement plant to control the aluminate reaction. The advantage of using hemihydrate is due mainly to its faster solubility in water. Although plaster is rarely added as a source of sulfate directly into the mill, varying amounts of calcium sulfate hemihydrate are present in the finished cement as a result of the dehydration of gypsum (the dihydrate form). This dehydration is prompted by high temperatures (e.g., above 100° C.) in the grinding mill environment that tend to evaporate water from gypsum and convert it into plaster.

In spite of attempts to control temperature and relative humidity conditions in the milling system, cement plant owners are not readily equipped to control precisely the amount of plaster being transformed from gypsum within the grinding process. This transformation is commonly seen in ball mill systems that readily generate heat; but not typically seen in vertical roller mills (VRMs) wherein the temperature of the mill is typically lower than the dehydration temperature of the gypsum, and additionally, the humidity is relatively higher, due primarily from water being added to stabilize the VRMs. Both conditions lead to decreased dehydration of gypsum to plaster.

Calcium sulfates can react with the aluminate phases to form ettringite, thus decreasing calcium aluminate hydration that otherwise decreases workability and strength of the cement. Although calcium sulfates can balance the aluminate reaction by keeping the sulfate concentration high enough to limit aluminate reactions in advance of the silicate reactions to prevent flash set and poor strength development (through hindrance of the calcium silicate reaction), a number of generally accepted standards in the industry (e.g., ASTM C1157, EN 197-1:2011) impose limits on total sulfate content. Such standards impose limits on the maximum amount of sulfate in cements under the theory that excessive sulfate levels give rise to detrimental expansion and false setting of cements. Other standards have evolved to permit higher sulfate levels as long as deleterious expansion is avoided (e.g. ASTM C150/C150M-18 does not limit the sulfate as long as tests under ASTM C1038/C1038M-14b do not demonstrate deleterious expansion).

Thus, an optimum amount of sulfate is desired to control the calcium aluminate reaction while maintaining performance factors such as strength, workability shrinkage, and expansion.

Despite the importance of adding the optimum amount of sulfate, testing for optimum sulfate levels in the grinding mill is typically done on an infrequent basis. Strength testing requires at least 24 hours, while calorimetric testing requires 8-24 hours. See e.g., Sandberg, P. "The use of isothermal calorimetry in cement production," http://downloads.calmetrix.com/Downloads/CCW2016/Paul_Sandberg_The_use_of_Isothermal_calorimetry_in_cement_production.pdf).

Given that large cement plants can produce 10,000 metric tons (MT) of cement every day, the present inventors believe that processing conditions (e.g., quality and ratio of raw materials fed into the kiln (10), the fuel used for heating the kiln, and other factors) present too many variables for the typical cement manufacturer to consider at present time.

The present inventors believe that a consistent quality of cement cannot be attained by adjusting sulfate levels annually, semi-annually or even monthly, because variations in the clinker over shorter time increments can alter the ideal sulfate level for reaching maximum strength at a given age of the cement.

In preparing for summary of the present invention, which culminates in the next section, the present inventors describe specific difficulties in testing the relationship between sulfate levels and optimum strength in cement, as well as current practices which have tended to mask discovery and resolution of those difficulties to this point in time.

FIG. 3A illustrates compressive strength data (at 1 day age) for cement containing various amounts of gypsum (dihydrate form). The gypsum is added incrementally into ground cement clinker in accordance with ASTM C563-17, and is dosed as a percentage of the cement mass. The cement made from variously dosed gypsum levels is used to form mortar test samples, which are crushed to obtain compressive strength values, in accordance with ASTM C109/109M-16a or EN-196-1:2016. The results shown in FIG. 3A are made in accordance to EN-196-1:2016.

The strength curve data of FIG. 3A suggests that the cement has optimum 1 day compressive strength when sulfate (in the form of gypsum) is added to the cement clinker in the amount of 1.5%-2.0% based on weight of cement.

Compared to compressive strength testing, calorimetric testing of cement samples using varying amounts of sulfate is undoubtedly more convenient. FIG. 3B graphically illustrates cumulative heat output testing, over a period of 24 hours, of hydrating cement samples containing gypsum (the dihydrate form) in varying amounts. According to the data illustrated in FIG. 3B, the optimum sulfate content (gypsum) for achieving maximum cumulative exothermic value in the cement is approximately 1.5%-2.0% based on the weight of the cement, essentially giving the same result as the compressive strength tests.

The present inventors note that, to this point in time, a process manager or the quality control manager of a cement clinker grinding mill would typically determine optimum sulfate content using a procedure such as the one described in ASTM C563-17. A small number of mortar samples with varying amounts of gypsum are formed into test samples which are crushed to obtain strength data (e.g., ASTM C109/109M-16a, EN-196-1:2016). FIG. 3C illustrates a typical four point curve using this conventional method. A mill operator might estimate, using such a small number of samples (for compressive strength testing or for calorimetric testing) that the optimum amount of sulfate (e.g., gypsum), for example, is 1.75% based on weight of cement. Based on this data, the mill operator would tend to set the level of gypsum addition in the mill at this amount for an extended amount of time, (e.g. the next 12 months).

However, the present inventors believe this conventional approach does not guarantee optimum strength because clinker components, kiln fuel, as well as the form or amount of sulfate likely fluctuate over the 12 month period and potentially on the daily and hourly periods. They also believe that optimum strength of the cement cannot be achieved consistently based on this conventional practice.

As explained in the background, the present inventors realize that the heat of the mill conditions could transform gypsum (dihydrate form) to the plaster form, which is more soluble (hemihydrate form). They also realize that the humidity levels in and around the mill could fluctuate greatly throughout any extended period of time, such that the amount of rapidly available sulfate could fluctuate.

Indeed, the present inventors believe that the amount of sulfate contained in the clinker itself, an amount of sulfate which albeit is typically small, can vary substantially and become a factor influencing strength of the cement at some point within any extended period of time (e.g. 12 months).

The present inventors believe that mill operators do not usually do multi-point compressive strength or calorimetry testing with enough frequency to obtain useful information regarding sulfate content and relative strength at certain ages; and that they do not routinely consider the myriad process conditions that change from moment to moment and that affect cement properties.

Although it is possible in a laboratory setting to measure sulfate levels in cement using X-Ray Diffraction (XRD) or X-Ray Florescence (XRF) after the cement is ground, there is no method to calculate the optimum gypsum (calcium sulfate dihydrate) or plaster (calcium sulfate hemihydrate) content based on XRF or XRD data.

Furthermore, there is no method that is used in the cement industry for adjusting the amount of dihydrate and hemihydrate forms of calcium sulfate to obtain optimum strength for certain cement ages. As a result, cements being produced today can demonstrate large fluctuations in terms of quality (e.g. set time and strength), despite investments in quality control systems by the cement manufacturers.

Cement manufacturers have attempted to mitigate the risks stemming from the variabilities of cement production by "overdesigning" their cement products. For example, this might be done by using more clinker and less supplemental cementitious materials (e.g., fly ash, slag) or by grinding cement particles to finer Blaine specific surface areas to increase the average compressive strength and make it less likely that strength fluctuation result in the cement not meeting specification. In either case, these approaches involve higher carbon dioxide generation (due to clinker kiln operation or milling electricity) and are not energy efficient.

Concrete producers also have used more cement to overcome inconsistent strength performance. Up to twenty percent extra cement might be used to ensure that strength targets are met. This again means more carbon dioxide is generated due to the greater demand for cement.

SUMMARY OF THE INVENTION

In surmounting the disadvantages of prior art approaches, the present invention addresses several issues in providing a method and system for optimizing sulfate and cement additive levels, cement fineness and other factors to attain target strength (at certain ages) or other performance targets when the cement is hydrated.

The present inventors take into consideration that (A) clinker components vary (e.g., ratio of calcium (from limestone), iron, silica, aluminate); (B) nature and type of kiln fuel varies (e.g., coal, municipal waste, recycled tires, etc.); (C) kiln conditions vary (e.g. oxygen levels, flame length, etc.); and that (D) the amount of available sulfate can vary due to the hydration state of calcium sulfate being introduced into the grinding mill. For example, gypsum can dehydrate into plaster due to the hot environment of the grinding mill, whereby the calcium sulfate is rendered more soluble; and, hence, sulfate is more rapidly available for use in balancing the aluminate reactions.

As illustrated in FIG. 3D, cements ground from three different clinkers, having different components and/or component ratios, are shown to require different sulfate contents (added as gypsum) to achieve a maximum 1-day strength. The present inventors believe this type of behavior can be found not only across various cement plants, but also within the individual manufacturing process of a single cement plant over a relatively short period of time.

Likewise, FIG. 4 shows the responses of three different cements (C1, C2, C3) to the addition of a given cement additive. FIG. 4 illustrates that the impact of cement additives on the strength of a cement depends on several characteristics of the cement that include its chemical and mineralogical composition and its physical properties. In this case, the Blaine specific surface area, which is an indication of the surface area of the cement, is held constant. Even as such, the differences in C1, C2 and C3 are a result of the respective clinker chemistry differences.

In summary, any given cement plant can have a significant fluctuation in the raw materials, kiln fuels and kiln operating conditions used for making cement clinker. Given this scenario, the present inventors believe that a mill owner (cement manufacturer) must not simply perform strength or calorimetric testing infrequently (e.g. just once a year) and rely on those test results for an extended period of time to make cement with a consistent quality.

Aside from frequent monitoring of the optimum sulfate, the present inventors also believe that the amount and form of calcium sulfate existing in the cement should be monitored and adjusted on a frequent basis, as this would help to minimize variation in the quality and performance of the cements. More preferably, the relative amounts of both calcium sulfate dihydrate (gypsum) and calcium sulfate hemihydrate (plaster) should be monitored and adjusted on a frequent basis. Doing so would permit a mill operator to take into consideration the effect of various changing environmental conditions, including plant and storage conditions, which can affect the source of calcium sulfate and levels of soluble sulfate available to control the aluminate balance, which, in turn, can affect cement performance.

Accordingly, in an exemplary embodiment, the present invention provides a method for manufacturing cement, comprising:

(A) introducing, into a grinding mill, raw materials comprising clinker, a source of sulfate chosen from gypsum, plaster, calcium anhydrite, or a mixture thereof, and optionally one or more supplemental cementitious materials and optionally at least one cement additive; grinding the raw materials, to produce a ground blend of particles comprising ground clinker and calcium sulfate; and separating the ground blend of particles within a classifier whereby a first portion of the particles or the finished cement are sent to a silo or other receptacle for containing the finished cement and whereby a second portion of the particles is recirculated into the grinding mill for further grinding;

(B) providing at least at least one sensor system chosen from infrared sensor system, laser diffraction sensor system, or both, and detecting emanation, reflectance, transmittance, or absorption of energy by or through the ground blend of particles or finished cement provided in step (A), and generating output signals corresponding to the detected energy;

(C) comparing output signals generated in step (B) to data stored in processor-accessible memory, the stored data comprising output signal values previously obtained from sensors measuring the emanation, reflectance, transmittance, or absorption of energy in the infrared spectrum, laser diffraction spectrum, or in both the infrared and laser diffraction spectrums, the stored data being correlated with a physical or chemical property of the corresponding finished cement, hydrated cement, or cementitious product made with the cement; and (D) in response to the comparison in step (C), adjusting (i) amount, form or both amount and form of calcium sulfate introduced into the grinding mill in step (A); (ii) classifier settings, thereby to change relative amounts of ground particles being sent to the silo and being recirculated back into the grinding mill; (iii) amount, type, or both amount and type of cement additives introduced into the grinding mill; (iv) amount of water being introduced into the grinding mill; (v) amount of air provided by adjusting power or speed of a fan or blower connected to ventilate the mill; (vi) amount or type of supplemental cementitious material introduced into the grinding mill; (vii) cement cooler setting, thereby to change the temperature of the finished cement or (viii) combination of any of the foregoing.

In further exemplary methods of the present invention, the amount and form of sulfate can be adjusted by taking into account (A) the total amount of calcium sulfate (i.e. gypsum, plaster and anhydrite) as well as (B) the ratios between each of the different forms monitored in the ground blend of particles or finished cement, and to adjust both (A) and (B) on a periodic basis. For example, monitoring and adjustment can occur monthly intervals or less.

In still further exemplary methods, the present inventors believe that even further advantages may be achieved through monitoring and adjusting the source of calcium sulfate (i.e., amount and/or form) in the ground blend of particles or finished cement on a more frequent basis, such as hourly, more preferably every fifteen minutes, and most preferably at an interval less than or equal to 5 minutes.

In still further exemplary methods of the present invention, the amount and type of chemical additive introduced into the mill can be adjusted on a periodic basis based on the monitoring and analysis of the ground blend of particles or finished cement.

The present invention also provides a cement grinding system which is configured to accomplish the exemplary method as described in the preceding paragraph. The cement grinding system comprises a mill and at least one IR sensor for monitoring sulfate levels in particles ground in the mill, the at least one IR sensor being in communication with a processor configured or programmed to monitor IR wavelengths reflected from particles ground in a cement grinding mill.

Further advantages and features of the invention will be discussed further hereinafter.

BRIEF DESCRIPTION OF DRAWINGS

An appreciation of the benefits and features of the invention may be more readily appreciated when the various sections of this specification are considered in conjunction with the drawings.

DETAILED DESCRIPTION OF EXEMPLARY EMBODIMENTS

Figure 1:
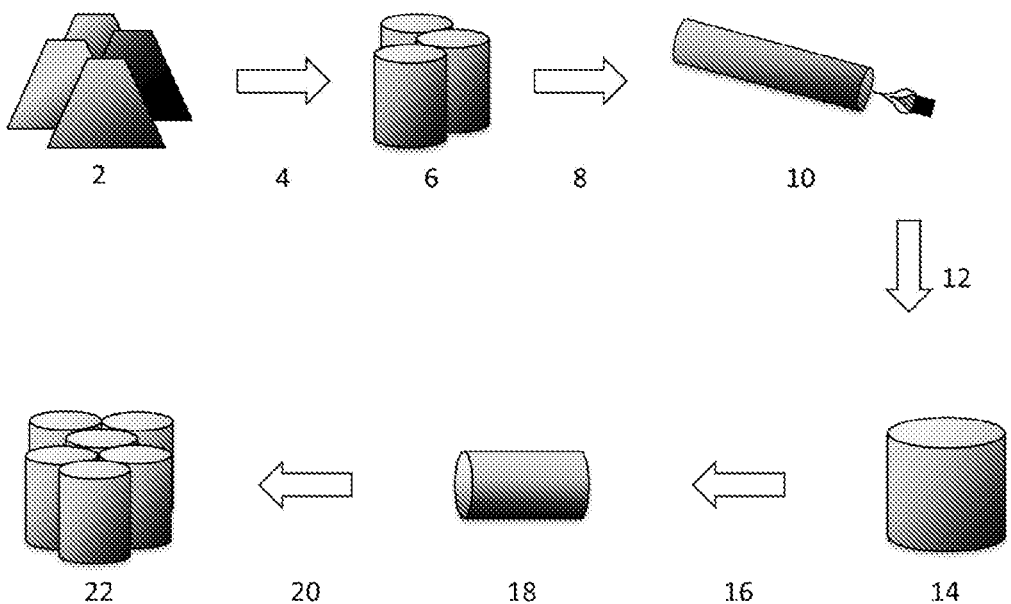
FIG. 1 is a flow diagram illustration (PRIOR ART) of clinker kiln and cement mill in the manufacture of cement (as discussed in the Background section).
Figure 2:
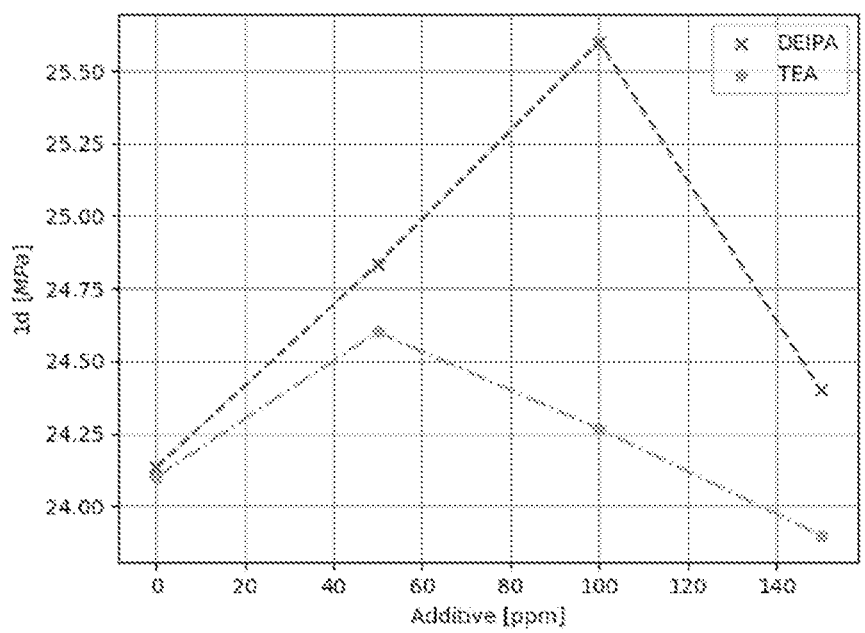
FIG. 2 is a graph illustration of 1 day compressive strength of two cements as a function of varying levels of cement additives (as discussed in the Background section).
Figure 3A:
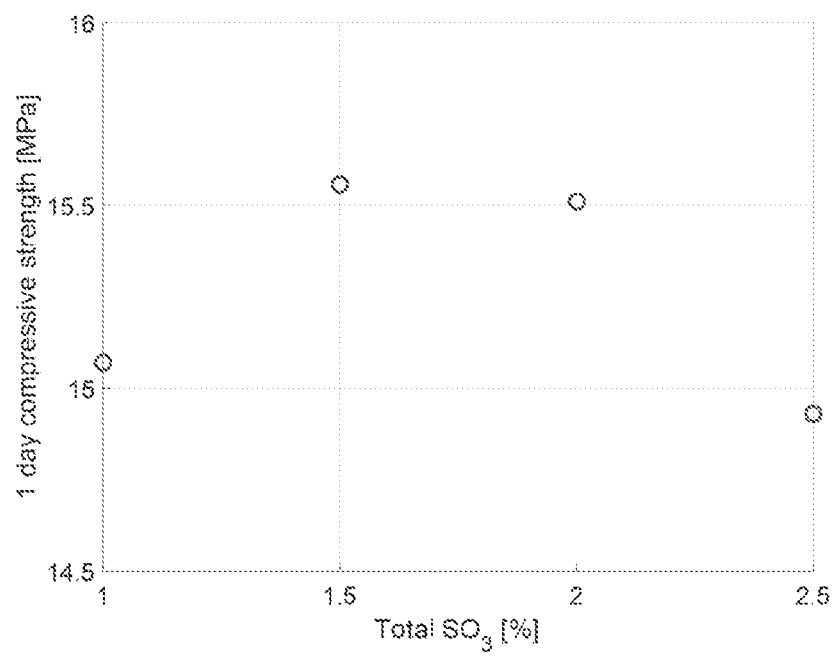
FIGS. 3A, 3B, and 3C are graph illustrations of data points obtained using conventional methods for optimizing sulfate levels in cement (as discussed in the Background section).
Figure 3B:
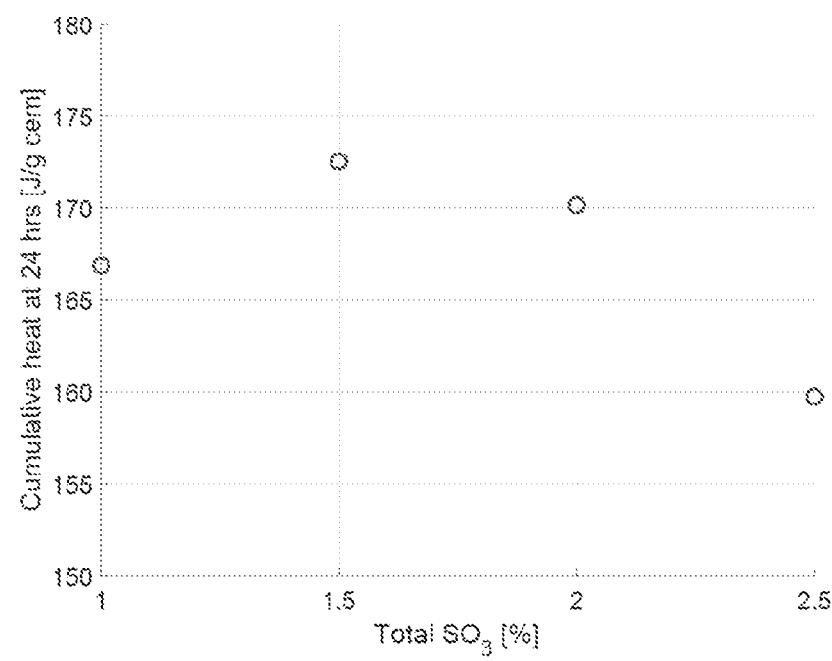
Figure 3C:
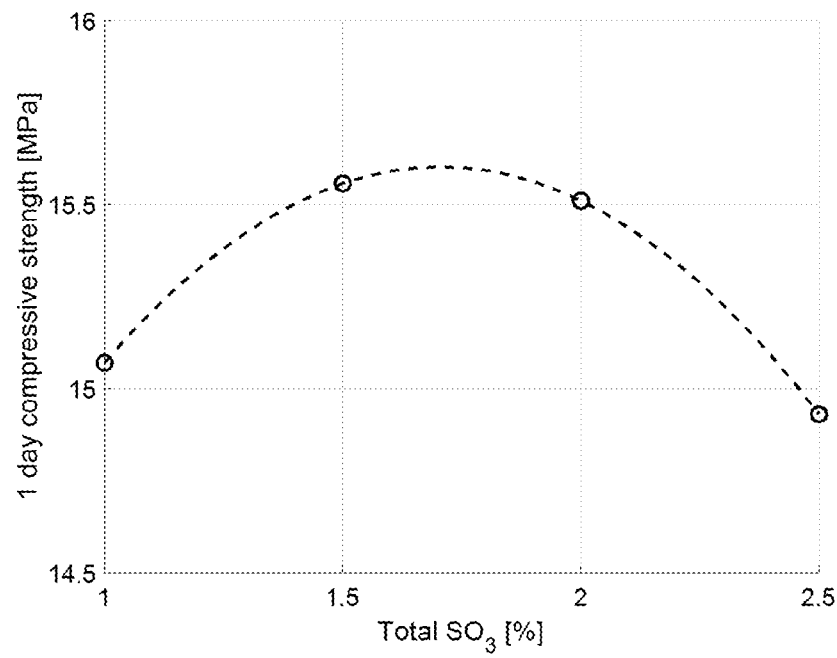
Figure 3D:
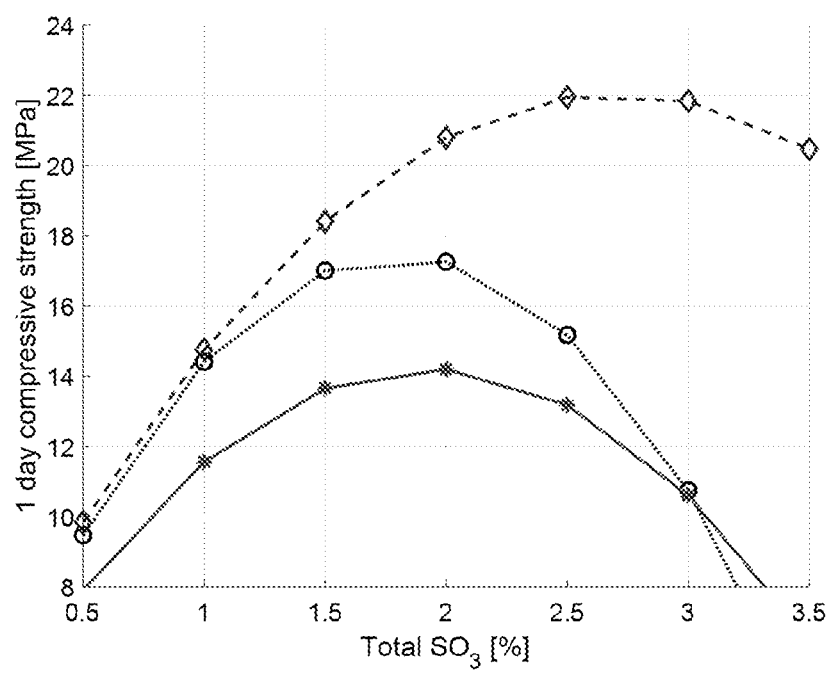
FIG. 3D is a graph illustration of one-day compressive strength as a function of varying levels of total sulfate in three cements (as discussed in the Summary section).
Figure 4:
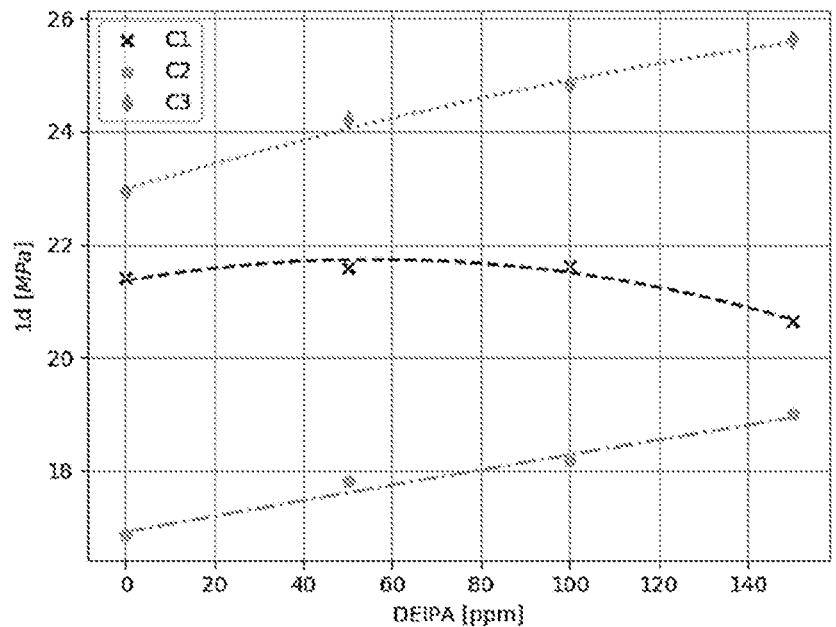
FIG. 4 is a graph illustration of varied performance when using the same cement additive in three different cements having same Blaine specific surface area (as discussed in the Background section).

As used herein, the term "cement" means and refers to hydratable cement, such as Portland cement, which is produced by grinding clinker consisting of hydraulic calcium silicates, aluminates, and aluminoferrites, and one or more forms of calcium sulfate (e.g., gypsum) as an interground addition. Frequently, Portland cement is combined with one or more supplemental cementitious materials as well as cement additives, and provided as a blend, all of which binds aggregates together to make a mortar or concrete.

The term "cement additive" means and refers to a chemical product of organic and/or inorganic nature that is added during the manufacture of cement either into the grinding mill, at the entrance of the separator or at the separator exit. Cement additives comprising grinding aids will primarily reduce the agglomeration of fine particles during the grinding process, and as a result, will increase the efficiency of the grinding mill. Cement additives comprising quality improvers or strength enhancers will primarily increase the strength of the cement during hydration. Strength can be enhanced at early ages (e.g. 1 day) or later ages (e.g. 28 days), and intermediate ages as well. Some chemical additives provide both early and later age strength enhancements. Frequently, chemical additives provide some level of both grinding enhancement and strength enhancement. Cement additives also refer to any chemical added during the cement manufacturing process that enhances any property of the cement such as, but not limited to: set time, shrinkage, expansion, workability, concrete admixture compatibility, etc.

The term "concrete admixture" means and refers to chemicals added during the manufacture of concrete.

As used herein, the phrase "supplemental cementitious materials" means and includes fly ash, silica fume, granulated blast furnace slag, limestone, clay, calcined clay, natural pozzolans, or mixtures thereof ("SCM"). These SCMs by themselves often have little or no cementitious properties, but, when blended with Portland cement and mixed with water, the blended cement and SCMs can bind aggregates together to make mortar, concrete, or other hydratable cementitious compositions.

The term "aggregate" means and refers to sand and/or stone (or crushed gravel) particles, typically having average size of 0.5 to 50 mm. Aggregates may also comprise calciferous, siliceous or siliceous limestone minerals. Such aggregates may be of either the "natural" type (e.g., derived from glacial, alluvial, or marine deposits which are typically weathered such that the particles have smooth surfaces) or may be of the "manufactured" type, which are made using mechanical crushers or grinding devices. Coarse aggregate stone particles are typically grouped into various size fractions as described for instance in ASTM C33-16e. As the size fraction used is controlled by various factors, such as the space between reinforcing bars in a proposed construction, aggregate size is often considered in concrete mix designs. The term "aggregate" may also be used to refer to crushed returned concrete (e.g. "recycled aggregate").

As used herein, the term "mortar" will refer to a mixture of cement and optionally supplemental cementitious materials such as limestone, fly ash, granulated blast furnace slag and other pozzolanic materials, water, and fine aggregates (e.g., sand). The term "concrete" is a mortar further containing a coarse aggregate, such as gravel or crushed stone. Mortars and concretes may optionally contain one or more chemical admixtures for modifying the hydratable cementitious composition in its plastic or hardened state (e.g., plasticizers for increasing workability, set accelerators, set retarders, air entrainers, air detrainers, plastic shrinkage reducing admixtures, corrosion inhibitors (for steel reinforcing bars within the concrete)).

As used herein, the phrase "a source of calcium sulfate" means and includes gypsum, plaster, and the anhydrite form of calcium sulfate. The term "gypsum" refers to the dihydrate form of calcium sulfate. Gypsum occurs as a natural mineral or by-product from industries. When subjected to sufficient heat, gypsum (more precisely $CaSO_4.2H_2O$) dehydrates to form calcium sulfate hemihydrate ($CaSO_4.0.5H_2O$) also known as "plaster." The mineral form of calcium sulfate hemihydrate is called bassanite. The complete dehydration produces calcium sulfate anhydrite ($CaSO_4$). Natural gypsum sources may contain impurities from other mineral such as quartz, calcite, dolomite, anhydrite, clays from deposits. The "gypsum" used in cement plants can also be obtained from chemical by-products such as phosphorgypsum (or phosphogypsum) from phosphoric acid manufacture, fluorogypsum from hydrofluoric acid manufacture, formogypsum from formic acid manufacture, desulphogypsum (or FGD™ brand gypsum) from flue gas desulphurization, etc. By-product gypsum can contain impurities that can affect the cement performance. Calcium sulfate dihydrate is commonly added to Portland cement clinker to control the set time and strength development of the cement.

At the optimum sulfate level for the particular cement, the rate of aluminate reactions are slowed in order to minimize their interference with the silicate reactions, thus allowing the strength of the cement to be optimized.

As used herein, the term "undersulfated" means that the level of sulfate added to the cement is below the optimum sulfate required to maximize the cement strength. Furthermore, severely undersulfated cement could cause "flash setting," referring to rapid loss of workability, large heat release, and dramatic loss of early strength development. In other cases, the undersulfated condition can lead to extended set and low strength gain development and poorer slump retention. Undersulfated conditions can also lead to problems with admixture performance, in part due to absorption of the admixture into certain hydrating aluminate phases.

As used herein, the term "oversulfated" means that the level of the sulfate added to the cement is above the optimum sulfate required to maximize the cement strength.

Amounts greater than that required to prevent the aluminates from interfering with the silicate hydrations do not help. Strength will go down further sulfate is added, sometimes sharply.

A second condition exists relative to higher sulfate levels, known as false set. This occurs when gypsum is dehydrated to form plaster (which dissolves faster), and there is relatively low aluminate activity to use of the sulfate that has dissolved. In this case, the plaster reforms into gypsum as crystals which physically lower the workability of the hydrating cement, generally in the first few minutes. While this does not directly impact the strength, addition of water to overcome the reduced workability results in a overall lower strength.

As used herein, the term "hydration" means and refers to the hydration of Portland cement which is a sequence of overlapping chemical reactions between clinker components, calcium sulfate and water, leading to setting and hardening. Cement hydration is most typically studied using a calorimeter to monitor heat released during hydration. Isothermal calorimetry is a particularly useful way to follow the progression of the cement hydration, which is the result of several simultaneous exothermic reactions. The major chemical reactions between clinker components and calcium sulfate in the cement, and water initiate the hydration process after water is mixed with the cement. The words "hydrated" or "hydration" may include the fact that cement is still curing or increasing in strength (e.g., compressive strength) over time.

In the cement and concrete industries, it is an understanding that Ordinary Portland cement (OPC) "prehydrates" during storage or handling in moist environments, forming hydration products on or near its particles' surfaces. Thus, the term "prehydration" is something of an oxymoron, since what is being referred to is unwanted hydration (or water bonding or reacting at the surface of cement particles) prior to the time at which the cement is used in concrete and mortar in combination with water and hardened into a mass or structure. Again, the term "prehydration" means and refers to an undesirable reaction between soluble components of cement (or its various phases) and moisture absorbed onto the surface of the cement particles either from liquid water or directly from the vapor phase that occurs before the cement is made into mortar or concrete upon mixing with hydration water (in amount sufficient to initiate hydration whereby concrete hardens into rock-like mass or structure). The level of prehydration of the cement can be quantitatively measured, for example, using analytical methods whereby the amount of water that is chemically bound to the particle surface is ascertained. Further detailed explication follows below.

Prehydration changes the surface of the cement particles, limiting the rate of dissolution which leads to a delay of setting, strength development and poorer flow properties. The surface change can also interfere with the action of chemical additives, rendering them less effective in some cases. Thus, it may be difficult to mitigate effects of prehydration reactions set time by using accelerators, for example. It is only necessary that a very small fraction (much less than 1%) of water taken up relative to cement mass will lead to negative effects at a later stage.

The most common adjustment made by cement plants in response to prehydration due to surface water reactions is to grind the cement particles to a higher fineness, to offset strength loss that typically occurs. This has well-known disadvantages, however, such as increased energy consumption, decreased throughput, and increased water demand for the finished cement. In summary, the prehydration of the cement can have quite significant effects on the properties of the cement once it is used to make concrete or mortar, and mitigating these effects after the prehydration reactions have occurred can be difficult.

Prehydration of the cement can be measured by heating a cement sample and measuring the weight loss within a defined temperature range. The level of prehydration reactions on the cement particle surfaces is most accurately measured using a thermogravimetric analysis (TGA) instrument. The amount or level of prehydration reactions on the cement particle surfaces is quantified for the present purposes as the parameter Wk, defined as the percentage mass loss of a cement sample as it is heated, starting at a temperature just after the completion of the gypsum dehydration and finishing at a temperature just before the calcium hydroxide (portlandite) starts to decompose. Chemically bound water starts to be released at temperatures as low as 60° C. and can continue until temperatures as high as 600° C. The Wk parameter measures the chemically bound water in a region of the weight loss versus temperature curve where only strength-giving clinker phases are dehydrating. At lower temperatures, there is also the dehydration of the added calcium sulfate phases and release of physically bound water; at higher temperatures, there is also the dehydration of calcium hydroxide from free lime and decarbonation of carbon-containing phases.

As used herein, the term "age" as it is used with respect to a cementitious composition refers to the time elapsed since the moment that water is mixed into the cement, mortar, or concrete to initiate the hydration of the cement, whereby the cement (when used to produce concrete) is hardened into a mass or structure. For example, strength properties may be measured at 1, 2, 3, 7, and/or 28 days (or at other "ages") after mixing with water. Different ages may have significance for different cement producers, and thus an optimum sulfate may refer to the sulfate required to optimize strength at a given age (e.g. 1 day, 28 days, etc.).

The major chemical reactions in cement during hydration are commonly identified in terms of five kinetic stages, as follows. These stages are most commonly observed via isothermal or semi-adiabatic colorimetry. Stage 1 represents primarily the rapid dissolution of clinker interstitial phases (including an initial dissolution of a fraction of the $C_3A$) and formation of ettringite or other aluminate reaction products. Hemihydrate dissolves, and gypsum or syngenite may form. Stage 2 is known as the induction period, which is characterized by a slowdown of the heat released. Stage 3 corresponds to the acceleration period when silicate hydrates begin to form i.e. C—S—H and CH. Stage 4 is characterized by the slowdown of the heat, which becomes even lower at the Stage 5. Although all cements hydrate when mixed with water, each stage of hydration can have a different rate, depending on multiple parameters, including but not limited to: cement chemistry, temperature, reactivity, water/cement ratio, presence of cement additives, etc.

Figure 5A:
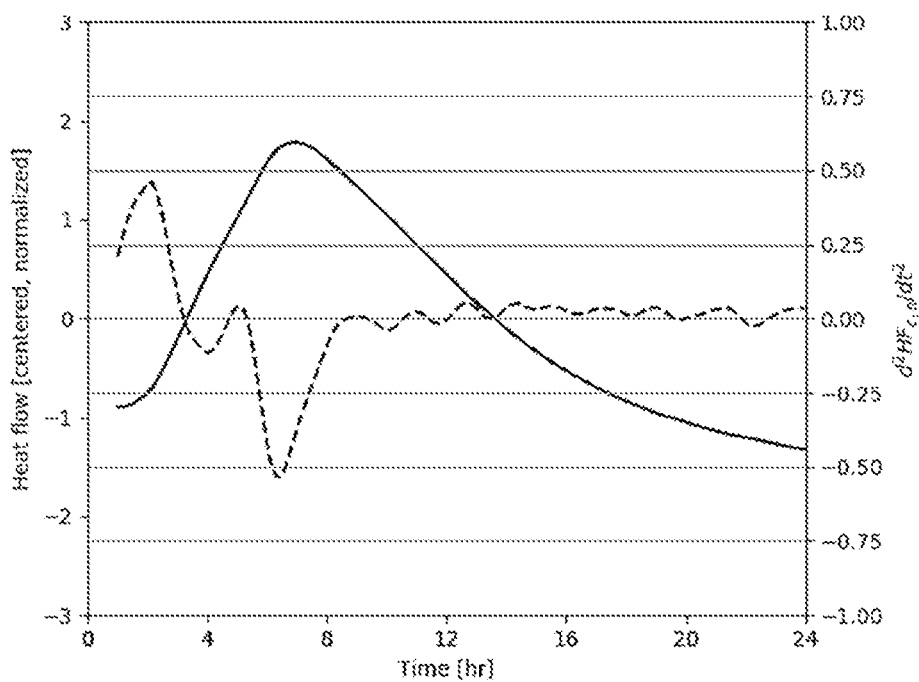
FIGS. 5A through 5E are graph illustrations of exothermic heat value (heat flow) as a function of time in five different samples of hydrating cement, demonstrating peak exothermic values corresponding to peak $C_3S$ reaction and the visible onset of the renewed or completed $C_3A$ reaction in the cement.
Figure 5B:
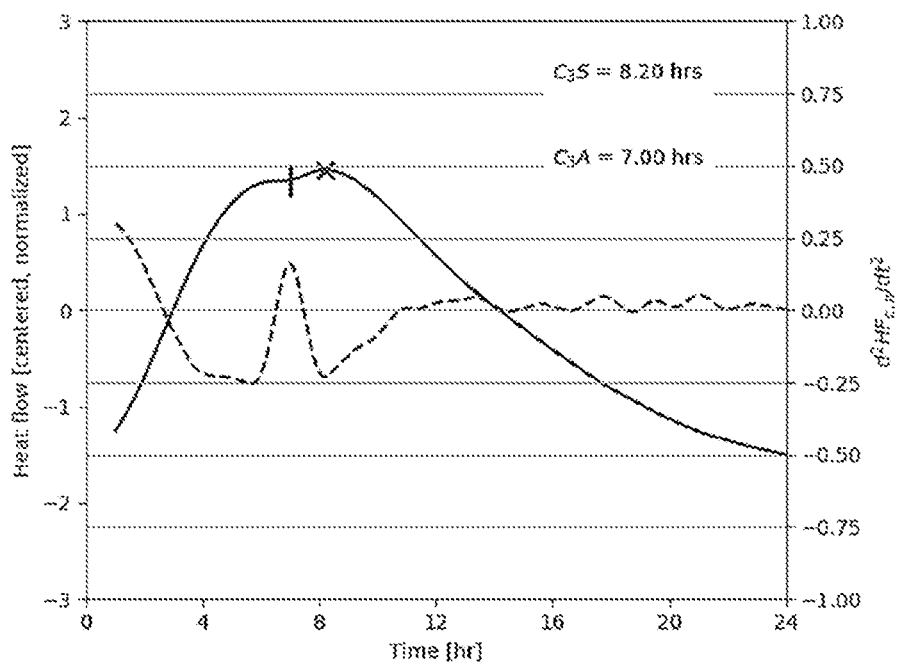
Figure 5C:
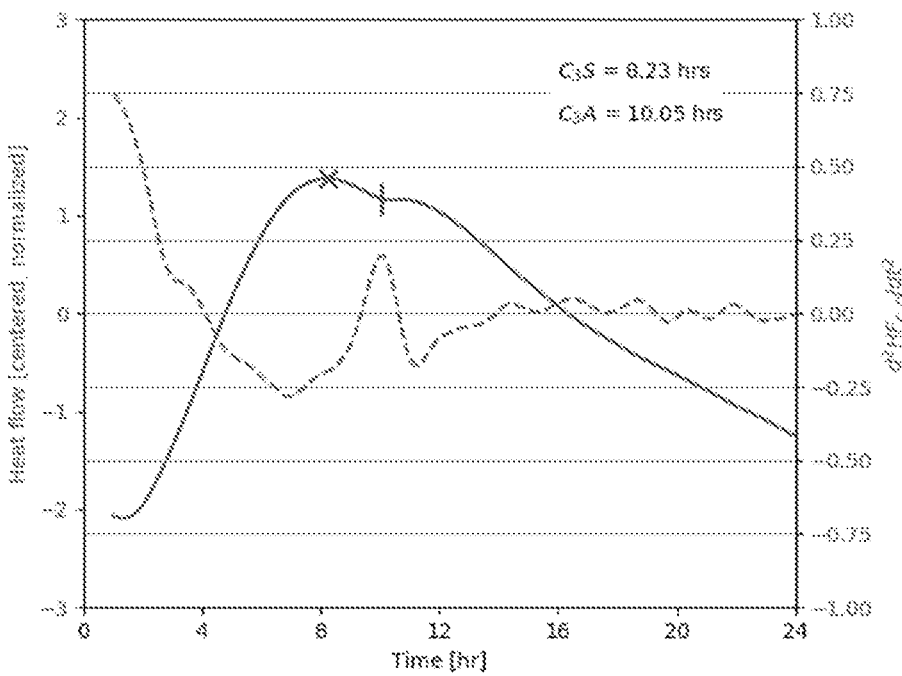

FIGS. 5A to 5E illustrate different hydration curve scenarios. The hydration behavior of a cement having a balanced sulfate content is shown in FIG. 5C. The solid line represents the heat flow, or rate of heat released by the cement system, over time. The dotted line represents the second derivative of the heat flow. In this set of figures (FIGS. 5A-5E), the heat flow is normalized and centered (i.e. the mean of the signal is subtracted from the signal and the result is divided by the standard deviation of the signal). In FIG. 5C, both the peak exothermic value corresponding to maximum $C_3S$ dissolution reaction rate (which is noted by the "X" symbol, appearing at the peak) and the visible "onset" of the renewed $C_3A$ dissolution reaction (which is represented by the "|" symbol appearing in the valley between peaks) are shown. Those skilled in the art will appreciate that the hydration curves (shown as solid lines) in FIGS. 5A-5E are summations or composites of separate reaction curves each having peaks (corresponding to primarily silicate and aluminate dissolution and precipitation reactions in the cement during hydration). Thus, the actual onset, or initiation of, the renewed $C_3A$ dissolution reaction that happens when there is no more available sulfate in hydrating cement, overlaps with the $C_3S$ reaction and vice versa. Thus, in line with typical methods in the industry (including e.g., ASTM C563-17), the present inventors focus on the visible onset from the calorimetry curve. Further analysis, such as taking first and second derivatives of the heat flow can help identify a reproducible renewed $C_3A$ onset, as one can see a local maximum in the second derivative in FIG. 5C corresponding to the onset of the renewed $C_3A$ dissolution (noted by the "|"). In FIG. 5C, the aluminate ($C_3A$) onset ("|") occurs after the maximum rate of heat released due to the $C_3S$ ("X"). It should be noted that separating the summations or composites of the reaction curves (e.g. the silicate reaction from the aluminate reaction) of the hydration curve is very difficult, and often requires other very sophisticated test methods to be run in parallel (see e.g. "Interaction of silicate and aluminate reaction in a synthetic cement system: Implications and the process of alite hydration," in *Cement and Concrete Research* 93 (2017) pp. 32-44 by Bergold et al.)

Figure 5D:
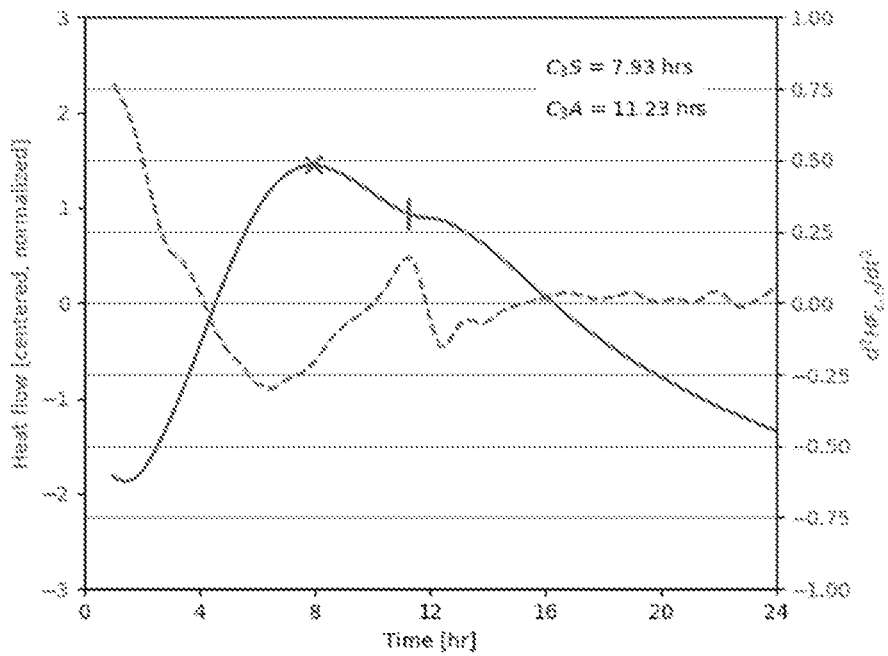
Figure 5E:
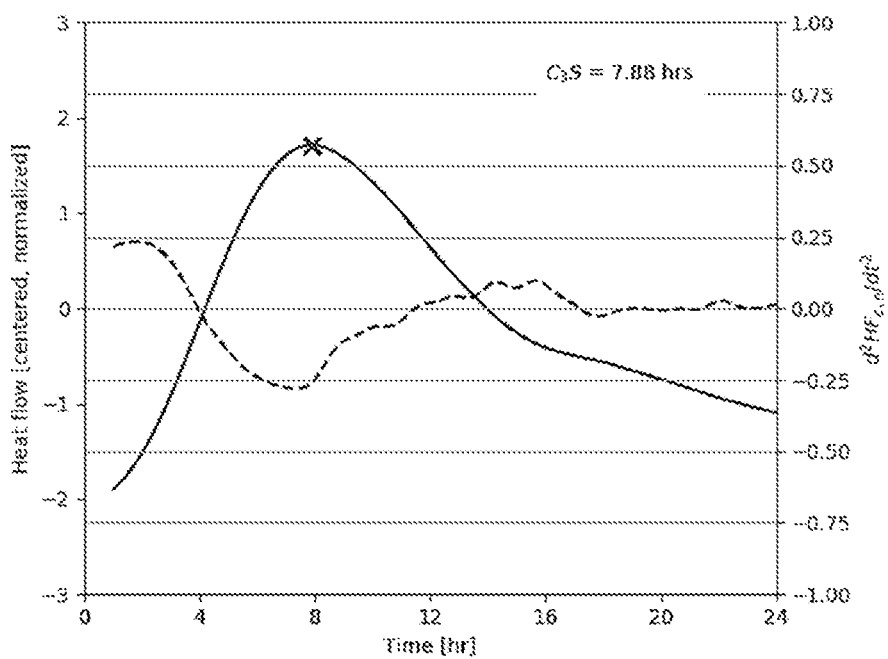

The difference between the times at which these two events described above occur is referred in this present invention as the Delta, $\Delta$ (i.e. time at $C_3A$ onset minus time at maximum $C_3S$ rate of heat release). In these cases where the system is oversulfated, Delta ($\Delta$) will be greater than zero. In FIG. 5D, the Delta is larger, and the shoulder or onset of the renewed $C_3A$ dissolution is less pronounced. However, the local maximum of the second derivative can still clearly identify the onset. In FIG. 5E, the shoulder is barely perceivable, and the local maximum of the second derivative may be considered on the same order of magnitude as the noise in the system. Although the time at maximum $C_3S$ rate of heat release is clearly defined, in this case, a system required to identify a Delta value may be programmed to assign an extreme oversulfated indicator instead of an actual Delta since the onset of the renewed $C_3A$ reaction is not clearly identifiable (through means such as a determining the local maximum of the second derivative). If the Delta is adjusted towards zero (becoming smaller), eventually, a local maximum of the second derivative will become clear, and the system can switch over to predict a numerical value for Delta when the second derivative clearly provides an indication of the renewed $C_3A$ onset. It should also be noted how clearly the maximum $C_3S$ rate of heat release is identified in over-sulfated systems (e.g. FIGS. 5C-5E).

In some cases, when the cement does not have sufficient sulfate for controlling the renewed $C_3A$ reaction, the $C_3A$ dissolution will complete before the peak of the silicate reaction. In this case, there is no renewed reaction after the peak in the $C_3S$ rate of reaction leading to a visible onset. However, there is a visible shoulder that is due to the completion of the $C_3A$ reaction. This shoulder will appear earlier in time with respect to the $C_3S$ peak. This is illustrated in FIGS. 5B and 5A. In FIG. 5B, again, the maximum $C_3S$ rate of heat release is designated at "X", while the shoulder is designated at "|". Strictly speaking, the shoulder here is actually the visible change in curvature of the curve corresponding to the completion of the aluminate reaction, that is, the point at which the dissolution of the $C_3A$ is substantially complete. After the completion of the aluminate reaction, the heat flow is primarily due to the silicate reaction. For simplicity, this feature (shoulder or visible change in curvature) is still called the onset. As was shown in FIGS. 5C and 5D, the onset is still clearly indicated by a local maximum in the second derivative in FIG. 5B. In a consistent manner, the Delta ($\Delta$) is determined by subtraction the time of maximum $C_3S$ rate of heat release from the "onset". In these cases, the Delta will be less than zero. If the system is mildly undersulfated, the $C_3A$ is allowed to react in an uncontrolled manner, and begins to hinder the $C_3S$ reaction (see FIG. 5A). In this case, the global peak corresponds to a combined heat signal from both the $C_3S$ and $C_3A$. Thus, this global peak is not strictly the $C_3S$ peak, and cannot be used as such. In this case, the $C_3S$ peak can be estimated from proper sulfated systems with nominally the same clinker. An undersulfated system is demonstrated in FIG. 5A, where there is no clear shoulder or sharp peak in the curve, and the second derivative shows no major local maximum. Similar to the extreme over-sulfated condition, a system required to return a Delta value may be programmed to recognize these conditions and assign an undersulfated indicator instead of a numerical Delta value. As the Delta is adjusted towards zero (becomes larger), eventually, a local maximum of the second derivative will become clear, and the system can switch over to predict a numerical value for Delta when the second derivative clearly provides an indication of the "onset".

The preceding paragraphs demonstrate one method to determine the Delta values. Other methods exist such as those outlined in ASTM C563-17, ASTM C1679-17, and in "Moving towards Automation" published in World Cement (July 2017).

Figure 6A:
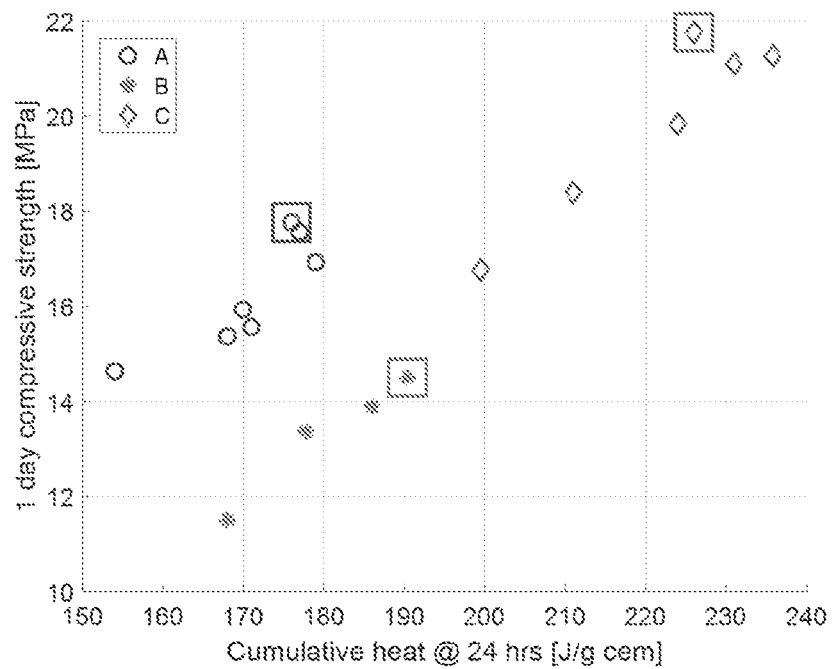
FIG. 6A is a graph illustration of one-day compressive strength as a function of exothermic values (cumulative heat) over 24 hours after water has been mixed into three cements to hydrate the cements, where the maximum strength for each cement is designated by the square symbol.

In FIG. 6A, 1 day compressive strength (measured in megapascals) is measured for three different cements (A, B and C) as a function of cumulative exothermic (heat output) over a 24-hour period (Joules/gram of cement). Furthermore, a square around the data points indicates the maximum strength for the given cement. Although within a given cement, the heat output correlates generally with the strength, the maximum strength occurs at a different heat output for each cement.

Figure 6B:
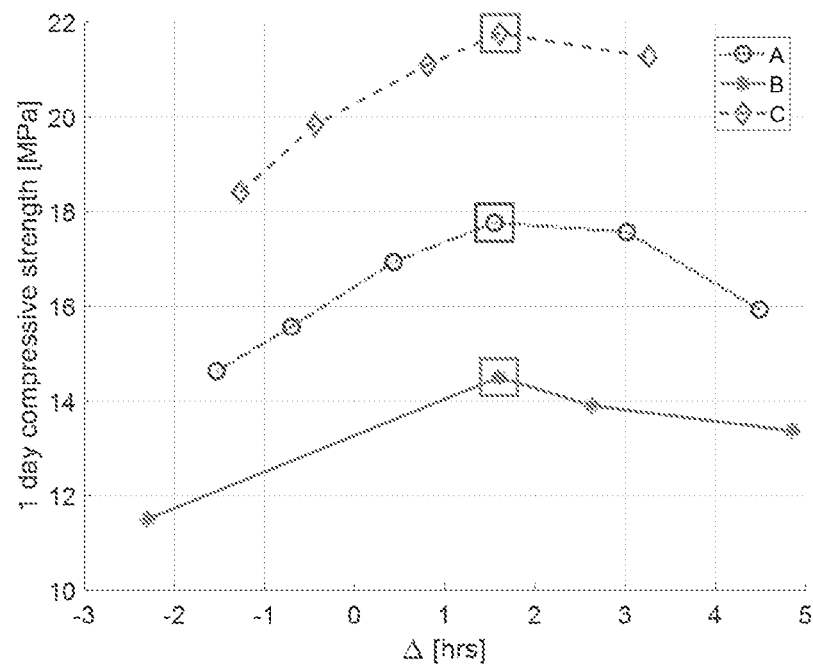
FIG. 6B is a graph illustration of one-day compressive strength as a function of the difference in the peak exothermic values which correspond to $C_3S$ and $C_3A$ dissolution in three cements, where the maximum strength for each cement is designated by the square symbol.

However, as shown in FIG. 6B, when one day compressive strength values (megapascals) were measured for three different cements and plotted on a graph as a function of Delta ($\Delta$), what appears to be a cogent pattern can be observed. In other words, the maximum strength of a cement is attained when its $\Delta$ value is in the range of ($-$)1 hours to (+)4 hours; more preferably, when its $\Delta$ value is ($-$)0 hours to (+)3 hours; and, most preferably, when its $\Delta$ value is 0.5-2.5 hours.

Based on the above discussion, a more complete and precise definition of the term Delta can be presented. A used herein, the term "Delta" ($\Delta$) refers to the time lapse (e.g., hours) between the exothermic peak corresponding to the silicate reaction ($C_3S$) and the visible onset of the exothermic peak which corresponds to (or approximates occurrence of) the renewed tricalcium aluminate reaction ($C_3A$) during hydration of the cement for systems that are oversulfated. In systems that are undersulfated, "Delta" ($\Delta$) refers to the time lapse (e.g., hours) between the exothermic peak corresponding to the silicate reaction ($C_3S$) and the visible change in curvature corresponding to the completion of the tricalcium aluminate reaction ($C_3A$).

Although the relationship discussed above between strength and sulfate content was first explained by Lerch in 1946 ("The influence of gypsum on the hydration and properties of Portland cement pastes", Proceedings, Vol. 46 of the American Society of Testing Materials), and is reflected in various standards including ASTM C563-17, the complexity of the cement production process severely limits the ability to control strength consistently. More recent means have been proposed to use the Delta as an ongoing quality control method, whereby the Delta found in calorimetry curves at the sulfate level giving the maximum heat output over the desired control period, for instance one day, three days etc., is used as a control target. However, as it takes a significant time, typically 8-24 hours for the hydration to progress to the point the Delta can be calculated, this must result at best in sulfate being adjusted to the conditions of 8-12 hours ago, not to the present time. Furthermore, this optimum Delta may have been established months ago, on potentially very different clinker, so the logic that controlling to a past optimum Delta is limiting the utility of such an approach. In the present invention, the Delta is determined continuously, and the optimum Delta target can be continuously refined by inclusion of recent test data in the model and even predicted in real-time. The present inventors therefore believe that frequent and continual monitoring of both the Delta and optimum Delta can best be performed using infrared radiation (IR).

As used herein, the term "infrared" refers to light or radiation energy having wavelength(s) in the range of 750 nanometers (nm) to 1000 micrometer (μm). The infrared (IR) radiation is commonly divided into three regions: the near IR (0.8-2.5 μm), mid IR (2.5-25 μm) and far IR (25-1000 μm) wavelengths. Infrared (IR) waves interact with a molecule, based upon vibrational changes of the atoms within the molecule. A portion of the radiation is absorbed, while the other portion is reflected radiation which can be sensed using an IR sensor and can be monitored. The IR spectrum reflected is a unique property of each molecule. The IR spectrum can serve as fingerprint to identify the presence and/or concentration of a molecule in a compound or material sample, including mixtures of ground particles as in the present invention. It is believed by the present inventors that, while mid IR has been used for organic compounds, the use of near IR ("NIR"), having higher frequency, can provide a greater resolution of information.

The use of IR sensors for assessing the content or quality of cement, clinker, and other powder materials, and for changing processing conditions, based on the spectral reflection is well-known. For example, in GB 2 111 193 A (1983), Ironmonger taught that IR could be used for irradiating a bed of clinker transported on a conveyor belt, and, based on the color reflection, could be used for determining whether the material had sufficient calcium oxide content. By using a comparator circuit to compare signal output with a threshold value, Ironmonger taught that the output stage could be used essentially to provide a control signal whereby corrective action would automatically be taken if the detection signal were to rise above the threshold. See e.g., GB 2 111 193 A at page 2, lines 54-59. As another example, in US Publ. No. 2003/0015663, Mikula et al. explained that certain peaks of intensity of reflected infrared (NIR) correlated with degrees of oxidation in oil sand ore; and they proposed on-line monitoring as a means for determining the degree of oxidation so that the information could be used to adjust processing conditions automatically (See e.g., US 2003/015663 at paragraphs 0002-0009). In Publ. No. 2004/0021077 A1, Ambuel commented that NIR analyzers were used for decades to measure constituents in pharmaceutical, refining, chemical manufacturing, and medical diagnostic fields, and thus models could be used based on the spectra to predict individual components and content. In his U.S. Pat. Nos. 7,310,581; 7,663,108; and 7,924,414; Mound confirmed that IR spectroscopic analysis could be used for analyzing bulk materials, and in U.S. Pat. No. 7,924,414 he specifically noted that IR analyzers could be used for analyzing "the mixture of clinker and gypsum transported to a mill (160), and the cement composition transported to silos for storage (175)" (See U.S. Pat. No. 7,024,414 at column 11, lines 49-56).

Data based on near infrared red (NIR), for example, has been successfully correlated with concentrations of various chemical species, and this has been used is the study of cement systems. For example, in U.S. Pat. No. 5,475,220, correlations between cement phases (e.g. $C_3S$, $C_3A$) and NIR spectra are demonstrated. Similar results can be found in U.S. Pat. No. 8,887,806. These types of correlations are practiced today (see e.g., http://www.spectraflow-analytics.com/products.html). Although chemical species are predicted today, correlations to performance characteristics such as strength and Delta ($\Delta$) have not been discovered until the present invention. Furthermore, prior art such as U.S. Pat. No. 7,924,414 focus on the raw materials entering the kiln, and subsequent process changes concerning the kiln (see e.g., Column 10, Line 66 through Column 11, Line 16).

Hence, the present inventors believe that by using a suitable energy source (e.g., infrared emitter) to irradiate ground particles of cement as they exit the grinding mill, and measuring the reflected IR radiation using an IR sensor, one may obtain information about the sulfate type and level in the ground particles. One can also obtain predicted values for actual performance properties corresponding to cement/sulfate particles having the same or similar IR data profile. For example, the reflected IR data collected by the sensor can be compared using a computer processor which is programmed to access database memory wherein IR data of previous ground clinker and calcium sulfate materials are stored along with (known or assigned) properties of the materials.

The invention is illustrated by the following enumerated example embodiments, including various exemplary aspects within the enumerated example embodiments. The following paragraphs describe a method for manufacturing cement; and, although "method" is ostensibly the term used for framing various process steps, it should be understood that the example embodiments, and various aspect descriptions, which follow also describe a "system" in that a computer processor electrically or electronically communicative with various sensors can be configured or programmed to perform the variously described steps, as follows.

In a first example embodiment, the present invention provides a method for manufacturing cement, comprising:

(A) introducing, into a grinding mill, raw materials comprising clinker, a source of sulfate chosen from gypsum, plaster, calcium anhydrite, or a mixture thereof, and optionally one or more supplemental cementitious materials; grinding the raw materials, optionally with one or more cement additives, and optionally with water, to produce a ground blend of particles comprising ground clinker and calcium sulfate; and separating the ground blend of particles within a classifier whereby a first portion of the particles or the finished cement are sent to a silo or other receptacle for containing the finished cement and whereby a second portion of the particles is recirculated into the grinding mill for further grinding;

(B) providing at least at least one sensor system chosen from infrared sensor system, laser diffraction sensor system, or both, and detecting emanation, reflectance, transmittance, or absorption of energy by or through the ground blend of particles or finished cement provided in step (A), and generating output signals corresponding to the detected energy;

(C) comparing output signals generated in step (B) to data stored in processor-accessible memory, the stored data comprising output signal values previously obtained from sensors measuring the emanation, reflectance, transmittance, or absorption of energy in the infrared spectrum, laser diffraction spectrum, or in both the infrared and laser diffraction spectrums (the stored data being correlated with a physical or chemical property of the corresponding finished cement, hydrated cement or cementitious product made with the cement, e.g., (i) strength test data, (ii) exothermic data; (iii) set initiation data; (iv) slump data; (v) dimensional stability data; (vi) air content data; (vii) prehydration level data; (viii) reduction or burn conditions data; (ix) cement particle size distribution data; or (x) a combination thereof); and (D) in response to the comparison in step (C), adjusting (i) amount, form or both amount and form of calcium sulfate introduced into the grinding mill in step (A); (ii) classifier settings, thereby to change relative amounts of ground particles being sent to the silo and being recirculated back into the grinding mill; (iii) amount, type, or both amount and type of cement additives introduced into the grinding mill; (iv) amount of water being introduced into the grinding mill; (v) the amount of air provided by adjusting power or speed of a fan or blower connected to ventilate the mill; (vi) amount or type of supplemental cementitious material introduced into the grinding mill; (vii) cement cooler setting, thereby to change the temperature of the finished cement or (viii) combination of any of the foregoing (e.g., in order to modify a physical or chemical property of the finished cement).

In a first aspect of the first example embodiment, step (B) comprises irradiating the ground blend of particles or finished cement obtained from step (A) using an infrared and/or laser radiation source. More preferably, the radiation comprises electromagnetic radiation having wavelengths in the range of 300 to 1,000,000 nanometers (nm). In preferred example embodiments, the sensors are part of an integrated system wherein an emitter or radiation unit is combined with a sensor.

In a second aspect of the first example embodiment, the grinding mill may be chosen from a ball mill or roller mill, such as a vertical roller mill. The term "roller mill" includes vertical roller mills ("VRMs") as well as horizontal roller mills (e.g., Horomill® brand horizontal roller mills), as well as mills that crush particles into finer size through nipped opposed rollers. VRMs have rollers which are pneumatically controlled to rotate in vertical direction upon a circular rotating table, and have a classifier that is integrated into or part of the same housing which contains the rollers and revolving table; and particles are fed into the center of table and move towards the outer circumference of the revolving table and crushed under the path of the rollers which are actuated by pneumatically assisted armatures. In VRMs, for example, at least one IR sensor is preferably located at the exit of particles from the housing which encloses the roller and classifier mechanisms, or, alternatively, along the pathway or conduit to the storage silo.

In a third aspect of the first example embodiment, the method comprises using the at least one sensor system to detect the infrared (IR) (e.g., energy having wavelengths in the range of 700 to 1,000,000 nanometers (nm) based upon IR reflected by, transmitted through, or absorbed by the ground blend of particles or finished cement. (Note: 700 to 1,000,000 nm wavelength corresponds to frequencies of 430 THz to 300 GHz). The at least one sensor system will preferably have ability to detect infrared radiation wavelengths in the range of 700 nm to 8 μm (430 THz to 37 THz); more preferably, in the range of 700 nm to 3 μm (430 THz to 100 THz); and, most preferably, 700 nm to 1400 nm (430 THz to 214 THz). NIR (Near Infrared Radiation) is typically 750-1400 nm (400-214 THz). SWIR (Short Wavelength IR) is typically considered to be in the range of 1400-3000 nm (214-100 THz). MWIR (Mid-Wavelength IR) is typically considered to be in the range of 3-8 μm (100-37 THz). LWIR (Long-Wavelength IR) is typically considered to be in the range of 8-15 μm (37-20 THz). FIR (Far IR) is typically 15-1000 μm (20-0.3 THz). ISO 20473 specifies that NIR encompasses the range of 0.78-3 μm, MIR (mid-infrared) encompasses the range of 3-50 μm, and FIR (far-infrared) encompasses the range of 50-1000 μm.

More preferably, the at least one sensor system provides output signals corresponding to the reflectance of energy by or through the ground blend of particles or finished cement. Using a sensor to measure reflectance (i.e., scattered reflection from the bed of particles) of energy from the IR source is preferred to measuring transmitted or absorbed energy. In still further exemplary embodiments, the sensor system may provide output signals corresponding to discrete wavelength ranges, regions, or specified spectra. One may employ two or more IR sensors, each dedicated to a region within the IR range.

In a fourth aspect of the first example embodiment, the invention provides a method involving use of the at least one sensor system which comprises a source of radiation wavelengths in the range of 300-700 nm emitted by a laser, and obtaining data based upon scattering of this radiation by and/or through the irradiated ground blend of particles or finished cement. Two types of lasers are commonly used for particle size analysis. First are red lasers, which typically are generated by HeNe lasers, producing red light at 632.8 nm. Laser diodes are also available, which use GaInP or AlGaInP quantum wells. The second type of lasers are blue lasers for wavelength detection in the range of 360 nm to 480 nm. Helium-cadmium gas lasers produce blue light at 441.6 nm, while argon-ion lasers can produce blue light having wavelengths in the range of 458 nm to 488 nm. Diode lasers (445 nm) are becoming more popular due to price. Semiconductor lasers, such as gallium nitride (GaN) can produce blue light as well. Many advances are occurring this area with new Thulium-doped and praseodymium-doped up-conversion lasers.

In a second example embodiment, which may be based upon the first example embodiment above, the invention provides a method wherein steps (A) through (D) are performed and repeated on at least a monthly basis or at shorter time intervals.

In other words, in a first aspect of this second example embodiment, the method more preferably involves steps (A) through (D) being performed and repeated on at least a weekly, daily, once-per-shift, or even hourly basis. Most preferably, the interval is every 15 minutes, and even smaller intervals such as every 2-5 minutes.

In a third example embodiment, which may be based upon any of the first through second example embodiments above, the invention provides a method wherein steps (A) through (D) are performed and repeated for successive 100,000 metric tons (MT) of cement clinker being ground in the grinding mill. More preferably, the steps can be repeated at more frequent intervals (e.g. 10,000, 1,000, or even smaller intervals).

In other words, in a first aspect of this third example embodiment, the method involves steps (A) through (D) being performed and repeated for successive 10,000 metric tons (MT), more preferably every 1,000 MT, even more preferably for successive 100 MT, and most preferably for successive 10 MT of cement produced.

In a fourth example embodiment, which may be based upon any of the first through third example embodiments above, the invention provides a method wherein steps (A) through (D) are performed and repeated upon a detected change in the cement production process. For example, the detected change can involve a fuel change, a material input change (e.g., composition of clinker, limestone, cement additives), water spray level or spray rate, temperature, internal or external air temperature, etc.).

In a first aspect of the fourth example embodiment, steps (A) through (D) are performed and repeated upon a change in the production process corresponds to a change in the kiln fuel feed rate or fuel type. It is known that the type of fuel used to heat the kiln can have a major impact on the aluminate-sulfate balance of the clinker. Examples of fuel types are coal, petcoke, oil, natural gas, as well as alternative fuels such as municipal waste, industrial waste (e.g. waste oil, animal feed, used carpets, used tires, etc.). Each of these fuels have different sulfur contents. Furthermore, within a given fuel, for example, for municipal waste, the sulfur can vary over time. Therefore, changes in fuel can cause issues for the cement producer as the resulting changes in the clinker need to be accounted for. Automatically detecting the change in the sulfate-aluminate balance (and making the necessary adjustments) not only enables a more consistent product through the fuel type change, but also can enable more fuel changes without performance issues. In particular, the switching from a high sulfur containing fuel to a lower sulfur containing fuel can have an especially dangerous impact on sulfate-aluminate balance, as it can cause formation of more highly reactive orthorhombic $C_3A$. Using the present invention, these situations can be overcome to balance the sulfate correctly for each fuel. This can be very beneficial for the environment as highly variable fuel sources such as waste (e.g. municipal waste), and can be used. The present invention thus allows for more variable fuel sources to be used.

Moreover, the NIR system can be used to determine variations in pertinent cement chemical components (e.g. sulfates, calcium aluminate form), and this can help to select the optimum type and proportions of different fuels to maintain a balanced sulfate-aluminate system. For instance if high variation in orthorhombic to cubic $C_3A$ ratio is detected by the NIR system, waste fuel streams can be adjusted to maintain consistent alkali to sulfate balance. Further, if environmental constraints dictate fuel blend changes on such a basis that the proper alkali sulfate balance is difficult to achieve, and the NIR system detects such issues, then compensating kiln feed composition changes can be made. As another example, if fuels used cannot supply enough sulfur to balance the alkali levels inherent in the raw materials, gypsum may be added to the raw feed to supply the needed available sulfate. These possibilities have previously been understood, but the NIR system's ability to continuously monitor composition is essential in enabling the determination of the level of variance and thus the relative importance of taking such steps. As orthorhombic $C_3A$ formation is also influenced by reducing conditions in the kiln, variation in the ratio absent sulfate-alkali balance changes in the kiln feed and fuel can be indicative of burning issues, which can then be addressed.

In a second aspect of the fourth example embodiment, the invention provides a method wherein steps (A) through (D) of the first example embodiment are performed and repeated when a compositional or chemical change in the raw materials, the raw meal, clinker, the finished cement or combination thereof, exceeds a predefined threshold. In particular, if $C_3A$ orthorhombic content within the clinker (as measured or estimated from, for example by XRD, XRF, etc.) exceeds a predefined threshold, steps (A) through (D) can be executed.

In a third aspect of the fourth example embodiment, the invention provides a method wherein steps (A) through (D) of the first example embodiment are performed and repeated when a change in the cement fineness exceeds a predefined threshold, such as a maximum deviation value (fineness target or range). This fineness characteristic can be measured offline (e.g. with a manual Blaine measurement) or online (e.g. with a particle size analyzer).

In a fourth aspect of the fourth example embodiment, the invention provides a method wherein steps (A) through (D) of the first example embodiment are performed and repeated when a change in a kiln process, a mill process or a both occurs. For example, if the flame length changes within the kiln, steps (A) through (D) can be executed. As another example, if the water spray rate within the mill is changed, steps (A) through (D) can be executed.

In a fifth example embodiment, which may be based upon any of the first through fourth example embodiments above, the processor is programmed to adjust the sulfate entering the mill in terms of calcium sulfate type, feed rate, or both type and feed rate. For example, this may be accomplished by adjusting feed rate of a calcium sulfate source into the mill or the ratio between forms of sulfate. As another example, during introduction of sulfate materials into the mill, one may add a combination of gypsum and anhydrite into the mill; and, once these are in the mill, one may adjust the temperature and moisture within the mill to control the dehydration of gypsum to plaster.

In a first aspect of the fifth example embodiment, the source of calcium sulfate introduced into the mill in step (A), whether in the form of gypsum, plaster, or anhydrite, can include synthetic versions (e.g., synthetic gypsum), phosphogypsum, as well as natural forms (e.g., natural anhydrites). Sulfates can include alkali or alkaline earth sulfates (e.g., calcium sulfate, sodium sulfate, potassium sulfate).

In a second aspect of the fifth example embodiment, the ratio between different forms of sulfate entering the mill is determined by using a sensor that monitors the sulfate source entering the mill. For example, an NIR sensor can be programmed to detect the relative amounts of gypsum and anhydrite (as plaster is rarely added into the mill, but appears as the gypsum is dehydrated once inside the mill) within the sulfate source being introduced into the mill. The processor can be programmed to use this information to adjust the total sulfate feed rate, adjust individual rates of gypsum and/or adjust mill processes that can control the ratios between the different sulfate forms after being introduced into the mill (including the gypsum to plaster ratio).

Both the amount and form of sulfate can affect characteristics of a cement, such as its strength and Delta. Thus, in a third aspect of the fifth example embodiment, the exemplary method further comprises storing data regarding total and relative amounts of the different sulfate forms entering the mill, and this can be performed during steps (A) through (C), and the data can be stored into processor-accessible memory (e.g., for use as later reference values). By combining the sulfate information as well as performance predictions generated from step (C), relationships between the sulfate adjustments and performance characteristics can be developed and used to make more efficient adjustments to the cement production process.

In a sixth example embodiment, which may be based upon any of the first through fifth example embodiments above, the processor can be programmed to adjust supplementary cementitious materials (SCM) entering the mill (e.g., being introduced into the mill at step (A)) in terms of type or feed rate, or both type and feed rate. This may be done for example by adjusting feed rate of an SCM source into the mill, the ratio different types of SCM introduced into the mill, or the respective feed rate of different SCM sources into the mill. For example, if a prediction based on the NIR, LD, T and/or M/RH sensors indicate that the strength (e.g. 1, 28 day) of the finished cement is 10% higher than a pre-defined strength target, the amount of fly ash can be adjusted until the predicted strength of the finished cement (including the adjusted proportion of fly ash) is reduced to the target. A similar approach can be taken if the predicted strength is lower than the target.

In a first aspect of the sixth example embodiment, the source of supplementary cementitious materials (SCMs) introduced into the mill in step (A) is chosen from limestone, fly ash, granulated blast furnace slag, clay, calcined clay, natural pozzolan, or a mixture thereof.

In a second aspect of the sixth example embodiment, the chemical composition of SCMs entering the mill can be monitored using one or more sensors to measure SCM entering the mill. For example, an NIR sensor can be programmed to detect the additional source of aluminates within the SCMs that must be accounted for in order to accurately adjust the sulfate-aluminate balance, which can affect the strength of the cement. SCMs may also have a more negative impact on early strength development due to higher amorphous contents and thus deserve monitoring and consideration in the comparison and adjustment steps.

In a third aspect of the sixth example embodiment, the exemplary method further comprises storing information regarding composition of the SCM in a processor-accessible database during performance of steps (A) through (C), and the data can be stored into processor-accessible memory (e.g., for use as later reference values). By combining the composition characteristic (e.g. $C_3A$ content, amorphous content) information as well as performance predictions generated from step (C) of the first example embodiment, and relationships between the SCM adjustments and performance characteristics can be developed and used to make more efficient adjustments to the cement production process.

In a seventh example embodiment, which may be based upon any of the first through sixth example embodiments above, the processor is programmed to adjust the introduction of chemical additives into the grinding mill in terms of type, formulation, amounts, dosage rate, or a combination thereof. For example, the dosage rate of a particular chemical or group of chemicals may be adjusted. The relative amounts of chemicals used in a formulation may be adjusted. As a further example, the processor can be programmed to adjust the rate by which specific chemical additives are introduced into the grinding mill.

The cement additive can be a conventional grinding enhancement additive, a strength enhancing additive, or other agent, or combination thereof, that modifies one or more properties of the cement during grinding, of the cement during hydration, or of the cement material after it is hardened into concrete, mortar, masonry, or a structure. The cement additive amount can be adjusted based on a strength prediction or other performance parameters, such as Delta, total heat released over a specified period of time (e.g. 24 hours), set time, slump, dimensional stability, prehydration level, etc. For example, if a prediction based on the NIR, LD, T and/or M/RH sensors indicates that the strength of the finished cement is 10% lower than a pre-defined target strength for a given age (e.g. 1 day or 28 days), the amount of a strength enhancing cement additive can be adjusted until the predicted strength of the finished cement (including adjusting proportion of cement additive) is increased to the target. If the predicted strength is higher than the target, the classifier setting can be adjusted to decrease the Blaine specific surface area in order to reduce the mill energy consumption, thus providing an energy and cost savings. Adjustment of chemical additive dosage can also cause a change in temperature due to the change in grinding efficiency. Using a combination of adjustments to both the sulfate feed and mill conditions, a wide variety of absolute amounts of gypsum/plaster/anhydrite can be achieved.

In a first aspect of this seventh example embodiment, the cement additive may be a conventional alkanolamine or acetic acid (including any salt or derivative thereof. For example, this may include triethanolamine ("TEA"), acetic acid, triisopropanolamine ("TIPA"), diethanolisopropanolamine ("DEIPA"), ethanoldipropanol-amine ("EDIPA"), tetrahydroxyethylethylene diamine ("THEED"), methyl-diethanolamine ("MDEA"), ethanol diglycine ("EDG"), a glycol, a glycerol, and mixtures thereof. Other conventional additives may be employed as desired by those skilled in the art.

In a second aspect of this seventh example embodiment, the cement additive may be chosen from the group of set accelerators and strength enhancers comprised of chloride, bromide, thiocyanate, iodide, perchlorate, formate, thiosulfate, nitrate and nitrite alkali or earth alkali salts (such as sodium sulfate), and mixtures thereof.

In a third aspect of this seventh example embodiment, the cement additive may be chosen from the group of set retarders comprised of gluconate salt, gluconic acid, molasses, sucrose, or corn syrup, or mixtures thereof.

In a fourth aspect In a third aspect of this seventh example embodiment, the cement additive may be chosen from defoamers comprising of (i) ethoxylated, propoxylated fatty alcohol or alkylphenol, (ii) polyalkoxylated polyalkylene polyamine, or (iii) a mixture thereof.

In a fifth aspect of this seventh example embodiment, the cement additive may be a combination of the above cement additives that provides performance enhancement to the ground cement. For example, organic acid chemicals such as tartaric or citric acid may be added to control the $C_3A$ side of the sulfate balance to complement a sulfate adjustment if needed (e.g. in situations where no more sulfate can be added because of limitations imparted by ASTM C1038/C1038M-14b).

In a sixth aspect of this seventh example embodiment at least one compositional or categorical characteristic of the chemical additive is stored in a processor-accessible database during performance of steps (A) through (C), and the data can be stored into processor-accessible memory (e.g., for use as later reference values). Compositional characteristics may include, for example, the relative amounts of certain chemicals within the chemical additive (e.g. amine, defoamer, etc.). A categorical characteristic can simply be the identification label for the given additive. By combining this information as well as performance predictions generated from step (C), relationships between the adjustments and performance characteristics can be developed and used to make more efficient adjustments to the cement production process. In other words, the formulation of the additive can be adjusted in real time based on how efficient the additive formulation is in adjusting one or more performance characteristics.

In an eighth example embodiment, which may be based upon any of the first through seventh example embodiments above, the processor is programmed to adjust a kiln process, a mill process or both.

In a first aspect of this eighth example embodiment, the processor is programmed to adjust the operation of the classifier that is used for removing sufficiently fine particles to send them to the storage silo and to recirculate coarser particles back into the mill. For example, the classifier can be adjusted to select out finer or coarser particles. The classifier can be adjusted a number of ways to change the particle size distribution and/or specific surface area of the finished cement, including air speed within the classifier, the rotational speed of distribution plates, vane settings, loading rates, and other factors. Many performance aspects of cement are affected by the particle size distribution and/or specific surface area, including strength, set time, workability, etc. By performing adjustments to the classifier, these performance characteristics can be adjusted. The classifier can also be adjusted in response to other changes in the mill process, such as to the introduction of a grinding aid. Because grinding aids can increase the efficiency of the grinding and classification process, the classifier can be adjusted to take into account the efficiencies imparted by the grinding aids to realize potential energy and cost savings.

In a second aspect of this eighth example embodiment, the processor can be programmed to adjust the operation of the water spray rate within the mill. One way to adjust the sulfate source is to control the temperature and humidity within the mill and thus the dehydration of gypsum to plaster (and furthermore to anhydrite in some cases), i.e. the ratio between the sulfate forms (gypsum/plaster/anhydrite). Temperature and humidity can be adjusted through the control of the mill water and temperature systems. Using predictive models, or real-time feedback from sensors (e.g. temperature, moisture or relative humidity sensors), the processor can be programmed to adjust water spray rate to adjust the temperature and humidity and thus the rate or amount dehydration of gypsum to plaster. Minimizing water spray helps to avoid or to minimize prehydration of the cement.

In a third aspect of this eighth example embodiment, the processor can be programmed to adjust the amount of air provided to ventilate the mill by adjusting the power or speed of a fan or blower connected to the mill. In addition to the water spray, the fan pulling air through the mill can also control the temperature (and thus the forms of sulfate). Again, a predictive model or real-time feedback from sensors can be used to determine deviations from pre-defined targets and thus what adjustments need to be made to incur a change of the gypsum/plaster/anhydrite forms.

In a fourth aspect of this eighth example embodiment at least one process parameter of the kiln or mill is stored in a processor-accessible database during performance of steps (A) through (C), and the data can be stored into processor-accessible memory (e.g., for use as later reference values). Process parameters may comprise, for example, the water spray rate, the air speed, a flame size, a fuel rate, an elevator bucket speed, etc. By combining this information as well as performance predictions generated from step (C), relationships between the process adjustments and performance characteristics can be developed and used to make more efficient adjustments to the cement production process.

The processor for purposes of step (D) can be programmed to perform adjustments to achieve a variety of changes to the cement production system to improve the quality of the cement. For example, the sulfate amount, the SCM blend, and any cement additive(s) can be optimized, in terms of amounts and in real time, to produce a target or maximum strength at 1 day (or other "ages" such as 28 days). As another example, the amount of water spray, air flow, and temperature can also be optimized for maximizing strength. Any of these factors or combination of these factors can alternatively be optimized for a target set time, or for compatibility with a particular concrete admixture. Another possibility is optimizing the sulfate-aluminate balance for a given climate (e.g. hot climates require more sulfate). Aside from optimization, characteristics such as strength can be optimized for consistency. That is to say, for example, the sulfate may be optimized for the given clinker, but the strength can be reduced (or increased) to match a target strength by, for example, adjusting the fineness of the cement (which depends on a control loop involving a particle size prediction from, for example a laser diffraction sensor system, or NIR sensor system) and/or by adjusting the type or amount of cement additive.

The choice of which adjustment(s) to make can be prioritized based on several factors. Some cement plants may be able to adjust only some of the processes described in (i) to (vii) of step (C) of the first example embodiment above. For example, blended cements (clinker with SCMs) are not common in the USA, and require additional feed systems. However, in Europe, blended cements are typical. The adjustments may also be prioritized based on their relative effect upon performance. For example, as fineness has a major impact on the strength of the cement (especially at early ages), it may be one of the first processes to adjust (such as by adjusting the separator settings and/or adjusting the dosage of the grinding aid). However, if prioritizing is based on manufacturing cost, it may be more preferred to grind coarser particles and instead add or adjust strength enhancing cement additives, decrease the amount of SCMs or adjust the sulfate balance. In another scenario, the $CO_2$ emissions may be a priority, and in this case, the amount of SCMs may be increased, which may require adjustments to the fineness, cement additive content or sulfate balance. Prioritization also depends on the sensor systems employed. Using an NIR sensor system with a laser diffraction sensor system may allow the cement plant to measure and manage the sulfate balance, and at the same time maintain the strength at a constant value by measuring and managing the fineness as well as adding cement additives. The choice of adjustments can also depend on balancing several different performance factors. For example, a particular sulfate level may be ideal for achieving a certain target strength, but not so favorable for achieving an acceptable setting behavior, or slump, slump retention as well as admixture response. The present invention thus makes it now possible to have flexibility to manage all of these different scenarios.

In a ninth example embodiment, which may be based upon any of the first through eighth example embodiments above, the method further comprising collecting data from at least one non-IR, non-laser sensor disposed or located within, or at the inlet or outlet of: (i) the grinding mill, (ii) an air flow inlet, outlet, or channel connected to grinding mill, or (iii) a kiln that produces cement clinker material introduced into the grinding mill. The data (e.g., output signal, associated value) from the at least one sensor is preferably stored and associated with data and/or associated value(s) previously stored in processor-accessible memory, for example, to serve as later reference values useful for step (C). The signal output of a sensor, or a value which is associated to the signal output, or both, may be stored into memory as a history of the process event and can be used in step (C).

In a first aspect of the ninth example embodiment, data collected from temperature, moisture, relative humidity sensors, or combination thereof, is stored in with the data stored in processor-accessible memory, where it can be used later, e.g., such as for reference in the comparison process described in step (C). Temperature and moisture data (which can be used to calculate relative humidity), thus producing further data or associated values which can be stored and used later as reference values in step (C)) can help determine dehydration states of gypsum (to plaster) within the mill. Also, because IR signals (i.e., NIR) are sensitive to temperature and moisture, use of independent temperature and moisture sensors can help to correct or to eliminate the effects of moisture which could otherwise adversely affect or complicate analytical predictions of cement properties (e.g. Delta, strength) based on the IR signals.

In a second aspect of the ninth example embodiment, the method of the invention further comprises an X-ray diffraction (XRD) sensor, X-ray fluorescence (XRF) sensor, thermogravimetric (TGA) sensor, particle size distribution (PSD) analyzer, prompt gamma neutron activation (PGNAA) analysis, and further comprises obtaining data from at least one of the afore-mentioned sensors and storing the data in processor-accessible memory for use in later reference, such as the previously stored data described in step (C). XRD, XRF, TGA, PSD, or cross-belt analyzers such as a PGNAA sensor from ThermoFisher® Scientific (of Waltham, Mass.) can be used to provide chemical analysis on a continual basis, which can help to confirm, improve or update calibrations for IR predictions (e.g. Delta, strength). Such sensors can also be used to trigger any of steps (A) through (D). For example, if the raw meal composition changes as detected by a PGNAA sensor, steps (A) through (D) of the first example embodiment is executed.

In a third aspect of the ninth example embodiment, exemplary methods of the invention further comprising using an ultrasonic sensor or other range-finder type sensor to generate data that can be stored in processor-accessible memory (e.g., step (C)). This information can be used, for example, to determine the distance from an IR sensor to the measured particles as they are conveyed on a conveyor belt or within a chute or other open channel. Using this distance information, the NIR received signal can be corrected in real-time for any changes in the distance from the probe to the measured particles. As another example, a particulate concentration sensor can be located in an air slide wherein the particles are measured by the NIR sensor, and this particulate concentration sensor can be used to correct in real-time for any changes in the concentration of the measured particle within the air-slide.

Furthermore, the processor in step (C) of the first example embodiment can be programmed to take into account additional inputs or signals regarding the cement manufacturing system, and these can be used to make the comparison. For example, information about the raw feed (raw material proportions, chemical composition), kiln processes (e.g. temperature, flame size, oxygen levels, output volume), fuel source and chemical composition, clinker size and chemical composition, mill processes (temperature, water spray, ventilation, mill void filling ratio, size of steel balls used, ball loading (which can be tied to acoustic sensor levels)). In addition, categorical inputs such as the name of an SCM type or additive type can be used to help indicate which data tables to use when predicting performance. For example, strength predictions when using a TEA-containing cement additive may be different than when using a DEIPA-containing cement additive. The formulation name can identify which predictive relationship to use.

In a tenth example embodiment, which may be based upon any of the first through ninth example embodiments above, the method further comprises providing an IR or laser sensor within an elevator bucket, conveyor belt, air slide, or pneumatic conveying device within or connected to the grinding mill. Sensors for measuring reflected and/or absorbed radiation can be used on moving cement particles, or cement particle samples which are removed from the production stream temporarily or permanently for IR radiation testing. Removal of a sample can be done "manually" (when desired) or "automatically" (at programmed intervals). Hence, the sensors used in step (B) for monitoring reflected, absorbed, and/or transmitted IR radiation can be located within a manually operated sampler or auto sampler.

In a first aspect of the tenth example embodiment, the method further comprises the use of an auto sampler, preferably such that if sufficient amount of sample can be removed from the product stream for IR testing, additional testing can be performed to measure strength, heat output, set time, workability, shrinkage or expansion, air content, prehydration or clinker reduction, or burn conditions associated with the cement.

In a second aspect of the tenth example embodiment, a combination of sensors at various locations can be employed. One preferred configuration involves location of a near infrared sensor (NIR), a laser diffraction sensor (LD), a temperature sensor (T), and a moisture or relative humidity sensor (M/RH) along or within a conduit, conveyer belt, channel, or pipe through or along which finished cement is conveyed from the grinding mill to a silo or other storage container. Another preferred configuration is to have the NIR, LD, T and M/RH sensors located along or within a conduit, conveyer belt, channel, air slide, or pipe through which the recirculated particles are redirected back into the grinding mill. Still another preferred configuration is to have the T and M/RH within the grinding mill and the NIR and LD along or within a conduit, conveyer belt, channel, air slide or pipe through or along which finished cement is conveyed from the grinding mill to a silo or other storage container.

In a third aspect of the tenth example embodiment, temperature sensors can be mounted after the grinding mill to monitor finished cement being sent to the cement silo (or other storage for the finished cement), including an additional temperature sensor in the silo itself. In addition, moisture or relative humidity sensors can also be mounted after the grinding mill to monitor the cement being sent to the cement silo.

In a fourth aspect of the tenth example embodiment, multiple sensors (NIR, LD, T, or M/RH) along a path (such as the path or conduit from the mill to the storage silo; or even before, within and after the cement cooler) or at different vertical levels within the storage silo, may be used to enable the operator or processor-controlled monitoring system to predict or measure the amount of gypsum conversion to plaster due to dehydration. This information can be used to adjust the source of calcium sulfate such that after conveyance to the cement silo, the final product will have the desired amount and forms of calcium sulfate. A temperature sensor (optionally in combination with a moisture sensor or relative humidity sensor), for example, can also be used to predict the amount of dehydration of gypsum to plaster. In other words, adjustments of the sulfate form and content can also be aided by an additional feedback system where the temperature of the finished cement as it is conveyed to the silo is monitored until the temperature of the cement has cooled to a final temperature (i.e. through temperature sensors installed in the silo or in proximity of the cement cooler). This information can be useful, as cement exiting the mill can still be at elevated temperatures (e.g. over 100° C.), and gypsum can still be dehydrating to plaster. By measuring temperature of cement and gypsum/plaster upon exit from the mill or classifier, and by knowing the temperature in the silo, the amount of dehydration can be predicted. This information can then be relayed to the processor which controls sulfate levels, so that adjustments can be made to take into account dehydration in the cement after it leaves the mill. Alternatively, the cement cooler settings can be adjusted to prevent further dehydration based on the temperature measurements.

In a fifth aspect of the tenth example embodiment, the invention provides a method wherein at least two energy radiation/sensor systems are employed, one of which is based on use of infrared sensor system having an infrared radiation emitter and infrared radiation sensor, the second of which is based on use of a laser diffraction sensor system having a laser emitter and radiation sensor for detecting laser energy passing through the irradiated finished cement. When two energy radiation/sensor systems are employed, two independent measurements can be taken. These independent measurements can be used to perform a variety of different tasks, for example, one measurement can be used to determine or improve the accuracy of the other measurement. Both measurements can also be used in combination to help train algorithms (e.g. regressions or machine learning sets) to predict different performance values (e.g. strength, exothermic results such as Delta). Where possible, the two independent measurements can help to control different parameters such as particle size (e.g. with the laser diffraction measurement) and sulfate balance (e.g., with the NIR measurement as measured by the Delta value).

In a sixth aspect of the tenth example embodiment, the invention further comprises employing an NIR sensor to determine chemical composition of the clinker entering the grinding mill. This signal can be compared to signals from the ground cement, which necessarily represents the composition of the bulk clinker, to better refine predictive relationships. It is understood that the signals obtained from clinker may be different compared to signals from crushed cement as the NIR reflectance of a clinker will mostly represent the surface. It is also understood that relative proportions of the chemical components of the surface of clinker may be different from the bulk of the clinker.

In an eleventh example embodiment, which may be based upon any of the first through tenth example embodiments above, the invention provides a method wherein, in step (C), the stored data obtained from finished or hydrated cement, is chosen from (i) strength test data, (ii) exothermic data; (iii) set initiation data; (iv) slump data; (v) dimensional stability data; (vi) air content data; (vii) prehydration data; (viii) reduction or burn conditions data; (ix) cement fineness data; or (x) or a mixture thereof.

In a first aspect of this eleventh example embodiment, the stored data is based on strength data and is obtained by casting a composition comprising the irradiated finished cement and water, with optional aggregates (either sand or gravel or both), and allowing the composition to harden after a specified period of time (for example, 6 hours, 1 day, 2 days, 3 days, 7 days, 28 days, 56 days, etc.). After the prescribed time has elapsed, the material (frequently cast as a prism (including a cube) or cylinder) is subjected to compressive load. The compressive strength (which may be tested, for example, in accordance with ASTM C109/C109M-16a or EN-196-1:2016,) is calculated upon failure of the specimen. These tests are usually performed under specified environmental conditions (e.g. temperature, humidity specifications), but can be performed at different conditions based on where the cement will be used by the cement producer's customers (e.g., if concrete produced with the given cement is mostly cast in warm climates, the specimens may be cast at temperatures elevated relative to what is specified by e.g. ASTM C109/C109M-16a).

In second aspect of this eleventh example embodiment, the stored data is based on calorimetric testing, whereby the heat released from a cement paste (cement and water), mortar (cement paste with sand), or concrete (mortar with gravel) are recorded over time. Different types of calorimetric tests exist such as semi-adiabatic, and isothermal (semi-adiabatic systems allow heat to leave the system, while isothermal refers to a system where the heat is measured at a constant temperature). Many different methods exist to look at heat released during the hydration of cementitious materials. For example, the total heat released over a period of time (e.g. 24 hours) can be quantified, and has been correlated to strength for similar cements. Heat released due to different reactions can also be quantified both in the intensity and time at which the reactions begin, are at their highest rate, or end.

In a third aspect of this eleventh example embodiment, the stored data is based on set initiation data, which typically involves initial set and final set times for a hydrated cement sample. The set times can be determined by penetration tests (or proctor tests), where the penetration into the material is recorded over time, and initial and final set are determined when the penetration meets certain prescribed values. Values such as initial set can also be determined by other types of tests, for example using shear wave reflection. Because liquids do not reflect shear waves, as the material hardens (sets), the shear wave reflection increases. Set time has also been shown to be indirectly estimated from calorimetric testing data.

In a fourth aspect of this eleventh example embodiment, the stored data is based on slump data. Slump data is a simplified way to refer to rheological behavior. The rheological data may be based upon or include data which reflects yield stress, viscosity, thixotropy (as measured for example by a rheometer, see e.g. ICAR rheometer), or more practical measurements such as slump (which can be measured using the drop in height when concrete is demolded from a truncated cone) or slump flow (which is usually measured in terms of horizontal spread of the concrete on a steel surface). In the cement plant environment, workability can be measured on cement pastes by, for example, the normal consistency test (see e.g. ASTM C187-16), or by use of flow tables with mortars (see e.g., ASTM C230/C230M-14). Hence, for example, reflected IR data may be correlated with slump, slump flow, or other rheology measurements.

In a fifth aspect of this eleventh example embodiment, the stored data is based on dimensional stability data, which involves changes in volume over time, such as shrinkage and expansion. There exist many standard measurements including ASTM C157/C157M-17 and ASTM C596-09(2017), for example. Hence, for example, reflected IR data may be correlated with such standard measurements.

In a sixth aspect of this eleventh example embodiment, a cement additive dosage response to one or more of the stored data is determined. The dosage response is calculated as the amount of cement additive required to achieve a given level of performance of a parameter such as strength at a given time (e.g. 24 hours), and alternatively set time, shrinkage, particle size distribution and/or specific surface area or other cement response to cement additive may be used. Furthermore, cement additives, such as grinding aids can also affect other properties such as the throughput of the mill. This data, usually represented as a response over different dosages, can be created by testing a given performance parameter for a range of dosages. Dosage responses can then be used to select a dosage or cement additive to be used during the production of the cement. Alternatively, if a less than ideal dosage or cement additive type is being used, instead of switching the dose or cement additive, the production parameters (e.g. sulfate form or amount) can be adjusted to improve the dosage response. Further, if the sulfate form is less than ideal but cannot easily be altered, the cement additive formulation can be changed based on knowledge of interaction of the cement additives with that sulfate form. Cement additives can, for example, include quality improvers (which can improve strength or other properties), grinding aids, which can improve grinding efficiency, or both.

In a seventh aspect of this eleventh example embodiment, a concrete chemical admixture dosage response to one or more of the stored data is determined. The dosage response is calculated as the amount of admixture required to achieve a given performance such as strength, set time, shrinkage reduction or other performance response. Typical concrete admixtures include "water reducing admixtures" (e.g., lignosulfonates, naphthalene sulfonates, polycarboxylate dispersant polymers), retarders, and other chemical admixtures that can affect the sulfate balance (and hence flash and false set) in many different ways. For a cement that is close to being under-sulfated (and hence has the risk of to flash set, or in other cases extended set), the use of concrete admixtures may push the cement system further towards being under-sulfated. Thus, the cement plant may choose to optimize towards a higher Delta (i.e. a greater amount of sulfate) in order to prevent such problems (i.e. the Delta is optimized for the presence of the concrete admixture). Thus, the practical target Delta may be higher than the Delta at optimum strength, in order to accommodate known field condition demands.

In an eighth aspect of this eleventh example embodiment, the stored data is based on the content or volume of air entrapped or entrained within a cementitious mixture, also known as the air content. There exist many standard measurements including ASTM C185-15a for mortar or ASTM C173/173M-16 for concrete. Cement additives can have an effect on the air generated as measured using these test methods. Undesirable air generation can lead to lower strengths for concrete or mortar mixtures created from the cement. Hence, for example, reflected IR data may be correlated with such standard measurements.

In a ninth aspect of this eleventh example embodiment, the stored data is based on the prehydration level of the cement particles (which indicates the amount of water chemically absorbed onto the surface of the cement particles). The prehydration level of the cement particles may be quantified using Thermogravimetric Analysis (TGA) and more specifically using a methodology to calculate Wk as described in "Prehydration of cement: global survey and laboratory results," in ZKG 6 (2018) by Silva, D. et al). Other quantifications of prehydration levels may include the total weight loss of the material expressed in percent weight.

In a tenth aspect of this eleventh example embodiment, the stored data is based on reduction or burn conditions data of the cement particles. During production of cement, changes to the kiln process and the resultant clinker composition can lead to reduction, over burn, and under burn conditions. Reducing 'oxygen deficient' kiln conditions can have a significant detrimental effect on the clinker and the resulting cement performance in terms of strength, setting, flow workability and kiln performance (fuel costs and maintenance). Reduction causes a series of changes to the chemistry and mineralogy of an affected clinker, including a raised orthorhombic $C_3A$ content, and reduced alite reactivity etc. The level of reduction in a specific clinker sample may be quantified using a combination of methods. Firstly, by the determination of abnormal changes in the actual clinker mineralogy determined by Quantitative X-ray Diffraction by Rietveld (known as QXRD, or alternatively XRD), as compared with the estimated qualities calculated from the bulk elemental composition—Bogue analysis (See e.g., Bogue, "The Chemistry of Portland Cement," *Journal of Physical Chemistry*, Vol. 52 (Reynolds Publishing Corporation (New York N.Y. 1947), which is determined by X-ray Diffraction analysis (XRF). Such clinker reduction can also be quantified by optical microscopy which can confirm the presence of atypical changes to the clinker microstructure (See e.g., Sibbick and Cheung, "Cement Clinker Microscopy as an Aid to Determine Performance Differences in the Presence of Chemical Additives, $36^{th}$ International Cement Microscopy Association Conference, Milan, Italy (2014)); and, finally, by the use of chemical reduction tests such as the Magotteaux test (See e.g., Hardtl, R., "Magotteaux test for cement analysis, in Betonwerk+Fertigteil-Technik, Vol. 69 (2003), or Manns, W., "Zur Braunverfärbung von Betonwaren—Möglichkeit der frühzeitigen Erkennung," Betonwerk+_Fertigteil-Technik, Vol. 68 (2002)). In a similar manner other cement kiln processes in terms of degree of burning (over to under) and other factors (raw feed residual issues, combinability, and cooling etc.) can be determined primarily by optical microscopy (alite crystal size, free lime and belite cluster contents, flux phase crystallinity) of the whole uncrushed clinker. However, these microstructural and compositional differences can also be verified by corresponding XRD and XRF analyses. Underburned clinker typically exhibits a less than optimum combination of the raw feed components into the primary calcium silicate and calcium aluminate phases, leaving partially burnt raw feed, undefined calcium silicate melt and higher than optimum free lime components. Overburned clinker typically exhibits high levels of combination into large well-formed and potentially lower reactivity alite crystals (>60 microns in diameter) and correspondingly lower belite, free lime and flux phases which can negatively impact late age strength development.

In an eleventh aspect of this eleventh example embodiment, the stored data is based on particle size distribution data of the cement particles, which involves size of a given set of particulate material. For example, the median or average particle size can be determined based on the size distribution. Other values may be the mass fraction of material above or below a given size, e.g. −32 micron represents the fraction of material below 32 microns, or the specific surface area, as measured by the Blaine test or by a laser diffraction PSD method. Furthermore, characteristics of the Rosner-Ramler relationship, such as the slope can also be used. Various particle size analysis instruments are commercially available.

In a twelfth example embodiment, which may be based upon any of the first through eleventh example embodiments above, the invention provides a method wherein, in step (B), the at least one sensor system is an infrared sensor system having an infrared emitter to irradiate the ground blend of particles or finished cement and an infrared sensor to detect infrared radiation reflected (IR) from the irradiated ground blend of particles or finished cement, the infrared sensor system thereby obtaining reflected IR data; and, in step (C), the processor compares the reflected IR data with stored reflected IR data corresponding to strength test data of hydrated ground blend of particles or finished cement at a predetermined age.

In an thirteenth example embodiment, which may be based upon any of the first through twelfth example embodiments above, the invention provides a method wherein, in step (B), the at least one sensor system is an infrared sensor system having an infrared emitter to irradiate the ground blend of particles or finished cement and an infrared sensor to detect infrared radiation reflected (IR) from the irradiated ground blend of particles or finished cement, the infrared sensor system thereby obtaining reflected IR data; and, in step (C), the processor compares the reflected IR data with stored reflected IR data corresponding to exothermic data stored in processor-accessible memory. The exothermic data is obtained by calorimetric measurement, over a period of time, of hydrating particle blends comprising ground clinker and source of calcium sulfate, wherein (i) total heat output is stored; (ii) two different exothermic time values are stored, a first value corresponding to a time $T_1$ indicating when the maximum silicate reaction rate occurs after initiation of cement hydration, a second value corresponding to a time $T_2$ indicating the visible onset of when either the renewed tricalcium aluminate reaction rate occurs (if occurring after $T_1$), or when the completion of the aluminate reaction occurs (if occurring before $T_1$) after initiation of cement hydration; or (iii) both (i) and (ii).

As used herein, the term "exothermic data" refers to temperature data obtained using a semi-adiabatic, or, more preferably, heat data obtained using an isothermal calorimeter (see e.g., commercially-available TAM® Air calorimeters). Typically, the heat output is summed over a 24 or 48 hour period, but may be measured for a longer period of time. A person skilled in the art of cement hydration will understand that accurately measuring the total heat output is not a trivial exercise. The measured heat output is quite variable depending on how fast the operator performing the test can properly mix the cement with water and place the sample in the calorimeter, as well as the difference in temperature between the calorimeter and the materials. Total heat output can be calculated by summing the heat output starting from an initial period of time (e.g. 1 hour, in which case the heat output from time=1 to 24 hours is summed and considered the total heat), or alternatively, starting from a time corresponding to the minimum heat rate during the induction period. The total heat generated is frequently correlated to a 1 day strength for a given cement type (e.g. Blaine, chemistry, etc.).

The time values corresponding to specific events during the heat evolution can provide an indication of the sulfate-aluminate balance. Sulfate (frequently in the form of gypsum) is added to the crushed clinker so that when water is added, the sulfate reacts with the aluminate phases in the crushed clinker. This is the primary aluminate reaction and happens on the order of seconds after the water is combined with the cement. Based on the amount and solubility of the gypsum (i.e. plaster is more soluble than gypsum, and as temperature increases, gypsum becomes less soluble), this primary aluminate reaction can be controlled, which allows a silicate reaction to proceed. This silicate reaction is the main contributor to the cement (and therefore concrete) strength gain. In most cases, a silicate peak is visible when looking at the heat flow rate over time during a calorimetry test (see e.g., the "X" in FIG. 5C). The time at which this occurs is $T_1$. If the sulfate-aluminate balance is sufficient, a renewed aluminate reaction will occur.

FIGS. 5A-E help to illustrate various hydration scenarios that can arise by application of calorimetry testing. The figures illustrate undersulfated to oversulfated states when the amount of sulfate mixed in with a ground clinker is changed. Based on how close the renewed aluminate reaction is to the silicate reaction, the onset can be quite visible, or, on the contrary, it can be difficult to discern. It can be revealed as a hump or shoulder (see hash mark appearing at 11.23 hours in FIG. 5D), or a clear second peak (see hump appearing to right of hash mark appearing at 10.05 hours in FIG. 5C). Many methods exist for determining the onset of the renewed aluminate peak, (e.g., ASTM C563-17, ASTM C1679-17). Determination of onset is best when done on a consistent basis (and, in this case, the $T_2$ is identified as the local max of a $2^{nd}$ derivative of the heat flow curve).

In a first aspect of the thirteenth example embodiment above, the method of the present invention may involve, in addition to use of the NIR sensor output, other information such as the gypsum amount/feed rate, or other predictions (such as the predicted gypsum amount, the predicted plaster amount, the predicted $C_3A$ content, the predicted amount of the orthorhombic form of the $C_3A$ mineral) that can also be combined with the NIR signal output value to provide a more accurate prediction of the Delta value. These other predictions can be provided based on the NIR signal or other means (such as periodic XRD or XRF measurements).

The orthorhombic form of $C_3A$ is interesting as it is remarkably more reactive in the presence of sulfate than is the alternate cubic crystal form. Its content is controlled by the complex balance of sulfate and alkali in the kiln, which can be affected not only by the raw material composition, but also by changes in the fuel sulfur level as well as by reducing conditions in the kiln, which tend to deplete the sulfate content by promoting formation of sulfur dioxide gases which exit the kiln and are not incorporated into the clinker. Due to the complexity of these interactions, unexpected changes in the orthorhombic $C_3A$ component can occur in relatively short time frames. The processor can be programmed to make a comparison between a combination of output signals from the NIR sensor as well as, for example, $C_3A$ orthorhombic content (supplied by XRD, for example), to data stored in processor-accessible memory, the stored data previously obtained by irradiating finished cements to sense an output NIR signal and accessing a $C_3A$ orthorhombic content. Based on this comparison, a prediction of a physical or chemical property of the corresponding finished cement can be made, or the current prediction can be refined and updated.

In a fourteenth example embodiment, which may be based upon any of the first through thirteenth example embodiments above, the invention provides a method wherein, in step (C), the stored reflected IR data corresponds to exothermic data comprising calorimetric measurements of hydrating ground finished cement; the method further comprising:

determining whether the difference between the time $T_2$ minus time $T_1$ is less than (−)1 hours or greater than (+)4 hours, where $T_1$ represents the time at which maximum silicate reaction rate occurs after initiation of cement hydration and $T_2$ represents the time after initiation of cement hydration at which either the renewed tricalcium aluminate reaction rate occurs (if after $T_1$) or at which the aluminate reaction is completed (if occurring before $T_1$); and, if the difference of $T_2$ minus $T_1$ is less than (−)1 hours or greater than (+)4 hours, adjusting the (i) amount, form or both amount and form of calcium sulfate introduced into the grinding mill; (ii) classifier settings, thereby to change relative amounts of ground particles being sent to the silo and being recirculated back into the grinding mill; (iii) amount, type, or both amount and type of cement additives introduced into the grinding mill; (iv) amount of water being introduced into the grinding mill; (v) amount of air provided by adjusting power or speed of a fan or blower connected to ventilate the mill; (vi) amount or type of supplemental cementitious material introduced into the grinding mill; (vii) cement cooler setting, thereby to change the temperature of the finished cement or (viii) combination of any of the foregoing.

In a first aspect of the fourteenth example embodiment, the method involves determining whether the difference between time $T_2$ minus time $T_1$ is less than 0 and greater than 3 hours; and, if the difference is less than 0 and greater than 3 hours, then any of the aforementioned adjustments or combination of adjustments can be made, based upon any of the aforementioned grinding mill conditions.

In a second aspect of the fourteenth example embodiment, the method involves determining whether the difference between time $T_2$ minus time $T_1$ is less than 0.5 and greater than 2.5 hours; and, if the difference is less than 0.5 and greater than 2.5 hours, then any of the aforementioned adjustments (or combinations thereof) can be made, based upon any of the aforementioned grinding mill conditions. A Delta between 0.5 and 2.5 hours typically maximizes the 1 day strength of the clinker. This range shifts if other performance targets are desired, for example, if later age strength are to be maximized, the Delta should be increased by 1-2 hours. Once the finished cement reaches the customer, addition of fly ash or clays (e.g. calcined clays) to the concrete mix can add additional aluminates to the cementitious system. In this case, the sulfate-aluminate balance will be shifted. A shift can also occur if the cement is cast at elevated temperatures. In this case, the increased temperature increases the reactivity of the aluminate, but decreases the solubility of the sulfate. This leads to an under-sulfated situation. In order to prevent this situation from occurring, the Delta target in the cement plant may be shifted to the right (increased). Thus, inputs from the field can be used to adjust the target Delta.

In a fifteenth example embodiment, which may be based upon any of the first through fourteenth example embodiments above, the invention provides a method wherein, in step (C), the stored reflected IR data corresponds to exothermic data comprising calorimetric measurements of hydrating ground finished cement; the method further comprising:

determining whether the difference between the time $T_2$ minus time $T_1$ is less than the predefined target minus 1 hour or greater than the predefined target plus 2 hour, where $T_1$ represents the time at which maximum silicate reaction rate occurs after initiation of cement hydration and $T_2$ represents the time after initiation of cement hydration at which either the renewed tricalcium aluminate reaction rate occurs (if after $T_1$) or at which the aluminate reaction is completed (if occurring before $T_1$); and, if the difference is less than the predefined target minus 1 hour or greater than the predefined target plus 2 hour, (i) amount, form or both amount and form of calcium sulfate introduced into the grinding mill; (ii) classifier settings, thereby to change relative amounts of ground particles being sent to the silo and being recirculated back into the grinding mill; (iii) amount, type, or both amount and type of cement additives introduced into the grinding mill; (iv) amount of water being introduced into the grinding mill; (v) amount of air provided by adjusting power or speed of a fan or blower connected to ventilate the mill; (vi) amount or type of supplemental cementitious material introduced into the grinding mill; (vii) cement cooler setting, thereby to change the temperature of the finished cement or (viii) combination of any of the foregoing.

In a first aspect of the fifteenth example embodiment, the method involves determining whether the difference between time $T_2$ minus time $T_1$ is less than the predefined target minus 0.5 hours or greater than the predefined target plus 1.5 hours; and, if the difference is less than the predefined target minus 0.5 hours or greater than the predefined target plus 1.5 hours, then any of the aforementioned adjustments (or combinations thereof) can be made, based upon any of the aforementioned grinding mill conditions.

In a second aspect of the fifteenth example embodiment, the method involves determining whether the difference between time $T_2$ minus time $T_1$ is less than the predefined target minus 0.25 hours or greater than the predefined target plus 1 hour; and, if the difference is less than the predefined target minus 0.25 hours or greater than the predefined target plus 1 hour, then any of the aforementioned adjustments (or combinations thereof) can be made, based upon any of the aforementioned grinding mill conditions.

The optimum Delta to maximize the strength is variable. While it is frequently in the time ranges identified above, so they represent appropriate starting point targets, various factors can alter it. For instance, if aluminate activity in the clinker or SCM increases, but the sulfate in the cement is in the form of more slowly soluble gypsum, a greater amount may be needed to increase the amount of sulfate that can dissolve at early times, and thus control the very early aluminate reactions so the silicate hydration is not restricted. This greater amount of gypsum for optimum strength would lead to a greater Delta, even though the actual time this extra gypsum was needed was much earlier. The ability of the present invention to detect such a change in clinker or SCM composition and adapt composition or mill control settings to accommodate the change is one of its key advantages.

In a sixteenth example embodiment, which is based upon any of the first through fifteenth example embodiments, the method further comprises comparing sensor data taken from step (B) to at least two different stored processor-accessible data sets. For example, in step (C), the sensor output signals obtained in step (B) are compared to two different types of stored data relating to different cement attributes or properties; or, as another example, relating to two different time periods from which the data was collected. It is possible that adjustments to processing conditions to change the strength will result in changes to Delta and vice versa. For example, if the Blaine specific surface area is increased to increase the strength, the ground clinker will become more reactive in terms of the aluminate phases, which will shift the Delta to lower time values. Thus, more sulfate may be added to compensate. Preferably, comparisons and subsequent adjustments are made in an iterative fashion.

In a first aspect of the sixteenth example embodiment, the at least two or more comparisons made in step (C) are further compared with respective targets; and based on the deviations from the respective targets, a processor selects adjustments and the order of adjustments, wherein the adjustments comprise (i) the amount, form or both amount and form of calcium sulfate introduced into the grinding mill in step (A); (ii) the classifier setting, thereby to change relative amounts of ground particles being sent to the silo and being recirculated back into the grinding mill; (iii) the amount or type of cement additives introduced into the grinding mill; (iv) the amount of water being introduced into the grinding mill; (v) the amount of air provided by adjusting the power or speed of a fan or blower connected to ventilate the mill; (vi) the amount or type of supplemental cementitious material introduced into the grinding mill; (vii) the cement cooler setting, thereby to change the temperature of the finished cement, or (viii) a combination of any of the foregoing.

In a seventeenth example embodiment, which may be based upon any of the first through sixteenth example embodiments above, the invention provides a method further comprising measuring the particle size of the clinker and calcium sulfate being ground in the grinding mill; and, in further response to the step (C) comparison between the obtained reflected IR data and the stored reflected IR, adjusting a particle size characteristic or property of the clinker and calcium sulfate being ground, or both.

In a first aspect of this seventeenth example embodiment, IR data, and more specifically, NIR data is used to predict a particle size characteristic of the ground cement, such as specific surface area (measured as, for example, Blaine), average particle size, $D_{x10}$, $D_{x50}$, $D_{x90}$, $D_{[4,3]}$, $D_{[3,2]}$, span 90-10, −32 micron, −45 micron, specific surface area, alpine (See e.g., M. C. Pasikatan et al., J. Near Infrared Spectrosc. 9, 153-164 (2001)), and the method involves making an adjustment to change particle size characteristic or distribution. If detected IR values do not match stored values corresponding to a desired particle size, for example, an adjustment can be done by altering classifier settings so as to obtain the desired particle size characteristic.

In a second aspect of this seventeenth example embodiment, data based on laser diffraction measurements can be similarly used to predict particle size characteristics of the ground cement, and similarly this can be compared to stored values, such that if measured laser diffraction values do not match stored laser diffraction values corresponding to a desired particle size characteristic, for example, an adjustment can be done by altering classifier settings so as to obtain the desired particle size characteristic(s).

In a third aspect of this seventeenth example embodiment, periodic data collected using the LD sensor system, which may be offline, can be used to update or refine the NIR calibration for prediction of a particle size characteristic of the ground cement.

In a fourth aspect of this seventeenth example embodiment, periodic data collected using a temperature sensor, moisture sensor, XRD, XRF, PGNAA or a combination thereof, which may be offline, can be used to update or refine the NIR calibration for prediction of a particle size characteristic of the ground cement. For example, XRD, XRF, PGNAA may give indications of iron which can help interpret the NIR signal.

In an eighteenth example embodiment, which may be based upon any of the first through seventeenth example embodiments above, the invention provides a method further comprising calculating a value corresponding to degree or level of prehydration of the cement, incorporating the value into processor-accessible memory, and initiating a decision whether to adjust the grinding mill or recirculation process conditions, and adjusting at least one of grinding mill or recirculation process conditions. For example, in step (B), the at least one energy radiation/sensor system is an infrared sensor system having an infrared emitter to irradiate the ground blend of particles or finished cement and an infrared sensor to detect infrared radiation reflected (IR) from the irradiated ground blend of particles or finished cement, the infrared sensor system thereby obtaining reflected IR data; and, in step (C), the processor compares the reflected IR data with stored reflected IR data corresponding to test result data indicating the degree or level of prehydration the cement.

In a first aspect of this eighteenth example embodiment, the method involves comparing output signal from IR sensor to stored data and calculating the degree or level of cement prehydration, the stored data being previously obtained by heating cement samples and measuring the weight loss within a defined temperature range. The prehydration level is most accurately measured using a thermogravimetric analysis (TGA) instrument.

Figure 7:
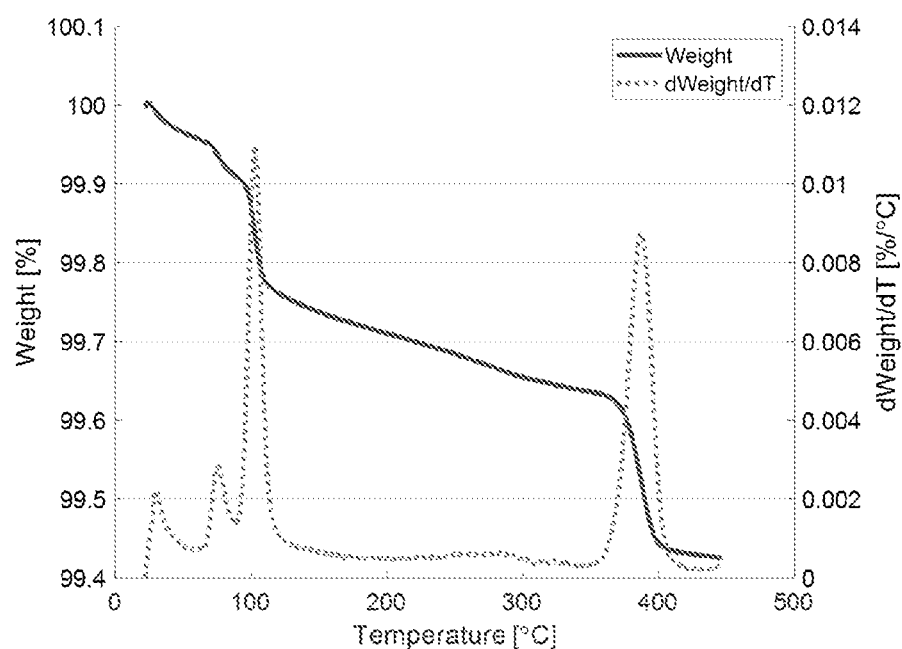
FIG. 7 is a graph illustration demonstrating weight loss over time and the derivative of the weight loss with respect to temperature for a cement sample obtained using a thermogravimetric analysis instrument. The cement sample is exposed to a temperature ramp from 22° C. to 450° C.

The quantitative measurement of "prehydration" level may be better appreciated with reference to FIG. 7, which illustrates both the weight change of cement as a function of temperature as well as the derivative of the change in weight with respect to temperature as the cement is heated from room temperature to at least 450° C. The prehydration level, designated by the symbol Wk, defined as the percentage mass loss of a cement sample as it is heated, starting just after the gypsum finishes dehydrating (about 125° C. in the example in FIG. 7) and finishing just before the portlandite (calcium hydroxide $Ca(OH)_2$) starts to decompose (about 350° C. in the example in FIG. 7).

In a second aspect of the eighteenth example embodiment, based on the prehydration level measurement (e.g., Wk), an adjustment is made to (i) the amount of water being introduced in the grinding mill in step (A), (ii) the amount of chemical additive introduced in the grinding mill in step (A), (iii) the amount of air provided (by adjusting the power or speed of the fan connected to ventilate the mill); (iv) the amount of cooling provided by the cement cooler; or (v) a combination thereof.

In a third aspect of the eighteenth example embodiment, a further comparison is made, which is based on a predefined relationship between the prehydration level and the Delta of the cement, the amount and/or type of sulfate (which is determined based on the comparison made in step (C)) is adjusted in response to a change in the measured prehydration level of the cement (which is based on a separate comparison made in step (C)), to correct Delta value so that it more accurately corresponds to or matches a predetermined target value. This can be performed as an iterative process.

In a fourth aspect of the eighteenth example embodiment, based on a predefined relationship between prehydration level and the strength of the cement (e.g. at the age of 1 day), the fineness or other parameters (as previously discussed) affecting strength is adjusted in response to a change in the measured prehydration level of the cement, to control the strength up or down to match a predetermined target value. This can be performed as an iterative process.

In a nineteenth example embodiment, which may be based upon any of the first through eighteenth example embodiments above, the invention provides a method wherein, in step (B), the at least one energy radiation/sensor system is an infrared sensor system having an infrared emitter to irradiate the ground blend of particles or finished cement and an infrared sensor to detect infrared radiation reflected (IR) from the irradiated ground blend of particles or finished cement, the infrared sensor system thereby obtaining reflected IR data; and, in step (C), the processor compares the reflected IR data with stored reflected IR data corresponding to test result data, and indicates on a monitor display, print out, or by visual or audible alarm when the degree of reduction in the clinker meets or exceeds a pre-established threshold value.

A reducing kiln environment (oxygen deficient) beyond a threshold can have a significant detrimental effect on the performance (strength) of the clinker produced and the resulting cement. A number of factors can influence the development of reducing conditions. Changes in raw meal composition, grind (size) and feed rate (and flow) can affect the oxygen consumption rate and thus the conversion of the kiln conditions from oxygen-rich to oxygen-deficient environment, without any changes to the other variables in the system. The other variables which can also influence the kiln conditions include changes in fuel type (calorific values, coal to petcoke, use of alternative fuels) and changes to kiln process (flame position and shape, air flow rates and sources, temperature etc.). To train the NIR to predict reduction, the test result can be obtained from a chemical reduction test such as the Magotteaux test (see e.g., Hardtl, R., "Magotteaux test for cement analysis, in Betonwerk+Fertigteil-Technik, Vol. 69 (2003), or Manns, W., "Zur Braunverfärbung von Betonwaren—Möglichkeit der frühzeitigen Erkennung," Betonwerk+_Fertigteil-Technik, Vol. 68 (2002)), or on results from chemical analysis such as XRD, XRF, and even furthermore from microscopy analysis.

In a twentieth example embodiment, the present invention provides a system for manufacturing cement, comprising:

a grinding mill for grinding raw materials including clinker, a source of sulfate chosen from gypsum, plaster, calcium anhydrite, or a mixture thereof, and optionally cement additives, to produce a ground blend of particles comprising ground clinker and calcium sulfate;

a classifier for separating the ground blend of particles whereby a first portion of the particles or the finished cement are sent to a silo or other receptacle for containing the finished cement and whereby a second portion of the particles is recirculated into the grinding mill for further grinding;

at least one sensor system chosen from infrared sensor system, laser diffraction sensor system, or both, for detecting emanation, reflectance, transmittance, or absorption of energy by or through the ground blend of particles or finished cement, and generating output signals corresponding to the detected energy; and a processor configured or programed to compare output signals generated by the at least one sensor system with data stored in processor-accessible memory, the stored data comprising output signal values previously obtained from sensors measuring the emanation, reflectance, transmittance, or absorption of energy in the infrared spectrum, laser diffraction spectrum, or in both the infrared and laser diffraction spectrums (the stored data being correlated with a physical or chemical property of the corresponding finished cement, hydrated cement or cementitious product made with the cement, e.g., (i) strength test data, (ii) exothermic data; (iii) set initiation data; (iv) slump data; (v) dimensional stability data; (vi) air content data; (vii) prehydration level data; (viii) reduction or burn conditions data; (ix) cement particle size distribution data; or (x) a combination thereof); and the processor further configured or programed to adjust (i) amount, form, or both amount and form of calcium sulfate introduced into the grinding mill; (ii) classifier setting, thereby to change relative amounts of ground particles being sent to the silo and being recirculated back into the grinding mill; (iii) amount, type, or both amount and type of cement additives introduced into the grinding mill; (iv) amount of water being introduced into the grinding mill; (v) the amount of air provided by adjusting power or speed of a fan or blower connected to ventilate the mill; (vi) amount or type of supplemental cementitious material introduced into the grinding mill; (vii) the cement cooler setting, thereby to change the temperature of the finished cement, or (viii) combination of any of the foregoing (e.g., in order to modify a physical or chemical property of the finished cement).

In various exemplary aspects of the above-described nineteenth example embodiment, the system of the invention may incorporate various exemplary features and aspects as previously described for the second through eighteenth example embodiments as described above.

In a twenty-first example embodiment, which may be based on any of the foregoing first through twentieth example embodiments, the invention provides a method or system which comprises, steps and/or components for:

(A) providing an indication (e.g., audible or visual alarm or indication, monitor or hand-held display, text message, email, etc.) that a physical or chemical property or amount of the raw materials, raw meal, clinker, the source of calcium sulfate, the chemical additive, the SCM, or the finished cement has changed;

(B) performing at least one test to determine a physical or chemical property on the finished cement chosen from (i) strength test data, (ii) exothermic data; (iii) set initiation data; (iv) slump data; (v) dimensional stability data; (vi) air content data; (vii) prehydration level data (i.e., measurement of amount or degree of chemical change and/or reaction product formed on cement particle surface due to reaction between absorbed moisture and certain phases of the cement); (viii) reduction or burn conditions data; (ix) cement particle size distribution data; and (x) a combination thereof;

(C) detecting from the finished cement tested in step (B) using at least one sensor system chosen from infrared sensor system, laser diffraction sensor system, or both; the at least one sensor system providing output signals corresponding to the reflectance, transmittance, or absorption of energy by or through the ground blend of particles or finished cement; (D) storing both the test results of (B) and (C) into a database accessible by a processor; and (E) making an adjustment to a model predicting at least one of physical or chemical properties listed above in subparts (B(i)) through (B(ix)), making an adjustment to a target value for at least one of (i) through (ix) or both.

In a first aspect of this twenty-first example embodiment, the indication is (i) a change in the fuel source; (ii) a predefined deviation from a chemical property as measured by IR, LD, QXRD, XRF, PGNAA or a combination thereof; (iii) a predefined deviation in the mill temperature or humidity; (iv) a predefined deviation in the relative raw materials entering the kiln; (v) a change in a kiln processing condition; (vi) a change in a mill processing condition; or (vii) a notification that a manual or automated cement sample was taken.

In a second aspect of this twenty-first example embodiment, the sample is obtained via an autosampler and more preferably, a sample obtained via an autosampler that is not composited over time.

In a third aspect of this twenty-first example embodiment, the indication is a change in any predicted value derived from a comparison between an IR signal and (i) strength test data, (ii) exothermic data; (iii) set initiation data; (iv) slump data; (v) dimensional stability data; (vi) air content data; (vii) prehydration level data; (viii) reduction or burn conditions data or; (ix) cement particle size distribution data; or (x) a combination thereof.

In a fourth aspect of the twenty-first example embodiment, the model is adjusted by recalibrating the model with the new data. The comparison described for step (C) of the first example embodiment can be performed through use of look up tables or by using algorithms configured to generate predicted test results. For example, this can be done by using the NIR signal output value to identify a similar signal stored in the memory and retrieve the associated test result data. This can also be done by using a mathematical function, based on the NIR, LD, T, M/RH sensor values, to generate a predicted test result value (e.g., a strength value). The algorithm or mathematical function can be derived based on standard regression techniques such as linear regression, partial least squares regression, regression techniques combined with principal component analysis or factor analysis approaches, or even machine learning, which includes both supervised (e.g. support vector machines, Bayesian methods, random forest methods, etc.) and unsupervised machine learning methods (k-means clustering, neural networks, etc.).

In a twenty-second example embodiment, which may be based on any of the foregoing first through twenty-first example embodiments, the invention provides a system and method of analyzing the performance of a cement, comprising: steps and/or system for (A) detecting from a ground blend of particles or finished cement obtained from step (A) using infrared sensor system output signals corresponding to the emanation, reflectance, transmittance, or absorption of energy by or through the ground blend of particles or finished cement; (B) comparing, using a processor, output signals provided by the infrared sensor system to data stored in processor-accessible memory, the stored data previously obtained by detecting from the finished cements by at least one sensor system (the stored data being correlated with a physical or chemical property of the corresponding finished cement, hydrated cement or cementitious product made with the cement, e.g., (i) strength test data, (ii) exothermic data; (iii) set initiation data; (iv) slump data; (v) dimensional stability data; (vi) air content data; (vii) pre-hydration level data, or; (viii) reduction or burn conditions data; (ix) cement particle size distribution data; and (C) returning a predicted physical or chemical property of the corresponding finished cement.

In a first aspect of the twenty-second example embodiment, at least two physical or chemical properties of the cement are predicted from the infrared sensor system output signal.

The invention can be embodied in many different modes and should not be construed (nor should expressions regarding what the "invention is or provides" be construed) as a limitation to the exemplary embodiments set forth herein; rather, these embodiments are provided so that this disclosure will be thorough and complete and fully convey the scope of the invention to those of ordinary skill in the art.

EXEMPLIFICATIONS

Figure 8:
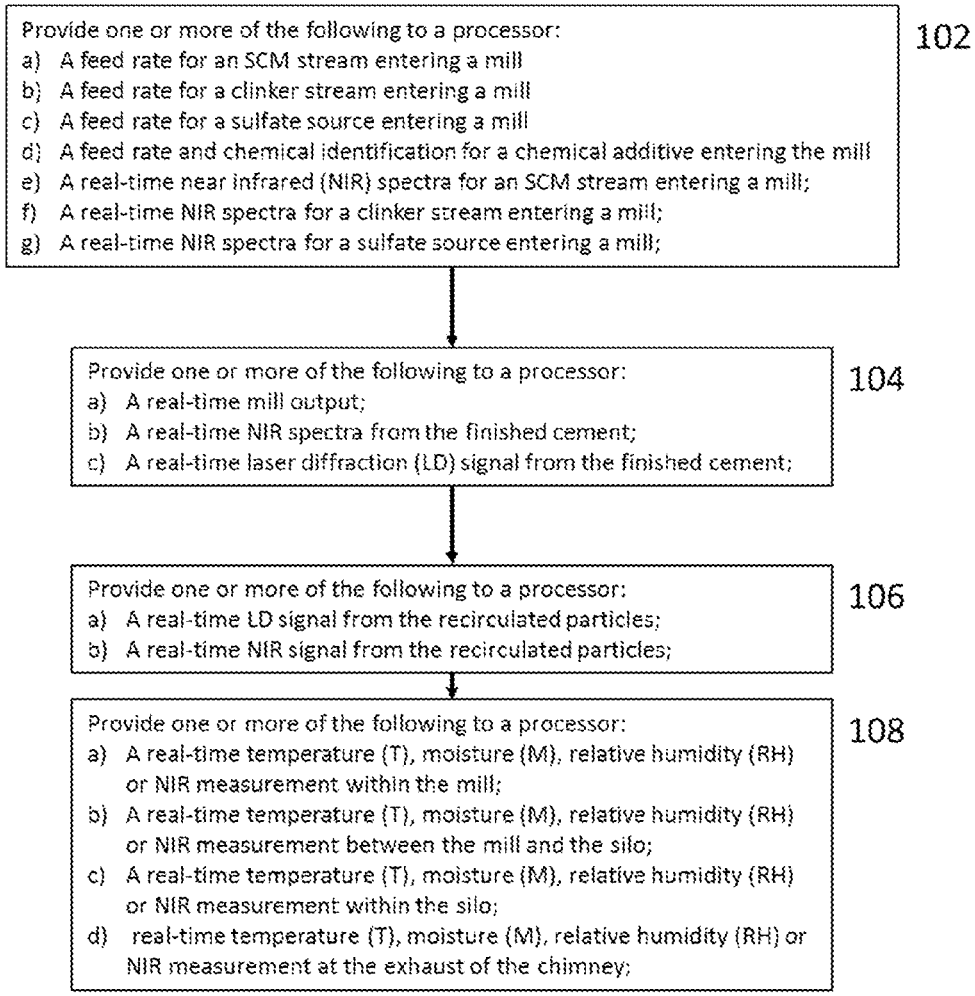
FIG. 8 is a flow chart of an exemplary method of the present invention.
Figure 9:
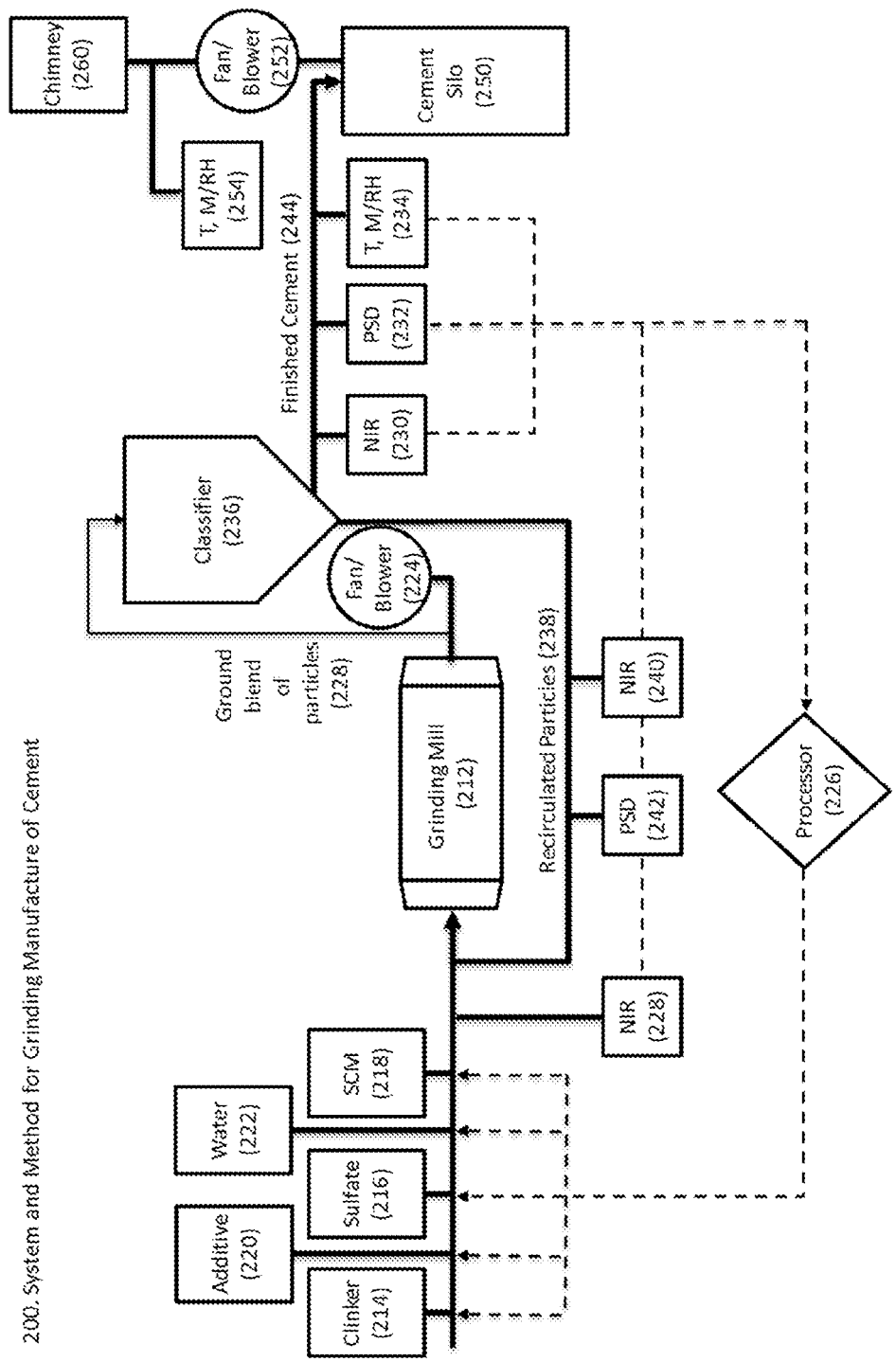
FIG. 9 is a diagram illustration of an exemplary system of the present invention.

In a first example, an illustrative method and system of the invention for adjusting sulfate levels in grinding manufacture of cement is outlined in the flow chart of FIG. 8 and illustrated in FIG. 9.

In block 102 of FIG. 8, a cement grinding mill (212 of FIG. 9) (e.g. a ball mill, vertical roller mill, etc.) is fed a combination of clinker (214), a source of sulfate (e.g. gypsum) (216), and optionally one or more SCMs (e.g. fly ash, slag) (218) and/or cement additives (e.g. strength enhancers, grinding aids, set modifiers, workability modifiers, sodium sulfate, chromium reducers) (220) at known rates, and exposed during the milling process to a water spray (222) at a known rate and a ventilation fan (224) set at a known speed. A computer processor (226) receives information about the feed rates and characteristics of each component (e.g. an identifying name). Furthermore, a near infrared (NIR) sensor (228) can obtain a reflection signal from the clinker, SCM and sulfate sources independently or as a group. These signals can be sent to and then analyzed by the processor via predetermined lookup tables or correlation functions to determine features such as alkali sulfates from the clinker; aluminate content from the SCM; gypsum/anhydrite ratios from the sulfate source (plaster is formed by dehydration of the gypsum during the milling process). For the chemical additive, identifiers (e.g. product name) or detailed information about the formulations (e.g. TEA content) can also be sent to the processor.

In block 104 of FIG. 8, the processor also receives information about the mill output volume as well as NIR spectra (230 of FIG. 9), a laser diffraction (LD) signal (232) and optionally a temperature, moisture or humidity (234) from the finished cement exiting the mill or optionally a temperature, moisture or humidity (254) from the chimney (260). These signals (including those on the SCM/sulfate/etc.) can be collected, for example, every minute. The multiple real-time NIR spectra can be collected using the same NIR spectrometer via input from different sensor channels. For example, the Bruker MATRIX-F FT-NIR spectrometer allows collection of signals from six different sensors. The signals are collected using sensor heads that transfer the signal to the spectrometer using fiber optic cables which preserves signal quality. This allows not only multiple sampling points, but also, allows the spectrometer itself to be placed in a protected area free from cement dust and other harmful elements (e.g. humidity and heat).

For NIR sensors situated to monitor material being carried on belts, the distance between the surface of the material (e.g., cement or SCM) bed and the sensor can vary with time as the material bed passes below the sensor. This can affect the measured NIR signal. A protective casing made of an optically clear (e.g. low light absorbance) material such as quartz, sapphire, or glass can be used to submerge the sensor within the material particles. This can allow the distance between the sensor and the material particles to remain constant.

Alternatively, a distance sensor, such as an ultrasonic range finder, can be installed next to the NIR detector so that a distance measurement can be made and used to adjust the NIR measurement or prediction in real time. Such a range finder is commercially available under the ULTRASONIC® brand (See e.g., https://www.maxbotix.com/Ultrasonic_Sensors.htm). Aside from the distance of the material to the detector, the material bed depth should be sufficient depending on the internal setup of the NIR instrument. In most cases, a bed height of more than 1 cm is sufficient.

Cement and other fine particulates can also be transported via a pneumatic tube or with air slides or other air-flow channels instead of a moving belt. In this case, an optically clear window can be installed in-line with the tube (or on a bypass tube connected to the tube). NIR signals can then be collected. For NIR instruments situated to monitor air slides, the concentration of the fluidized bed particles may affect the NIR signal. In this case, the NIR signal may be adjusted based on changes in parameters such as the air slide flow rate.

Preferred for use in the present invention are IR detectors suited to measure diffuse light (e.g., light that is scattered by a particle bed).

The system may also include more than one NIR sensor. In one example, different NIR sensors may be programmed to only scan a narrow window of wavelengths to improve the speed and/or accuracy at which the spectra is collected. For example, one NIR may be dedicated to determine a gypsum amount while another may be dedicated to a Delta measurement. It may be that different predictions of parameters (e.g. Delta or strength) require different spectral ranges or values. It is also possible to program a wavelength hopping scheme, where discrete regions of the wavelength spectra is collected instead of the entire spectra.

Figure 10A:
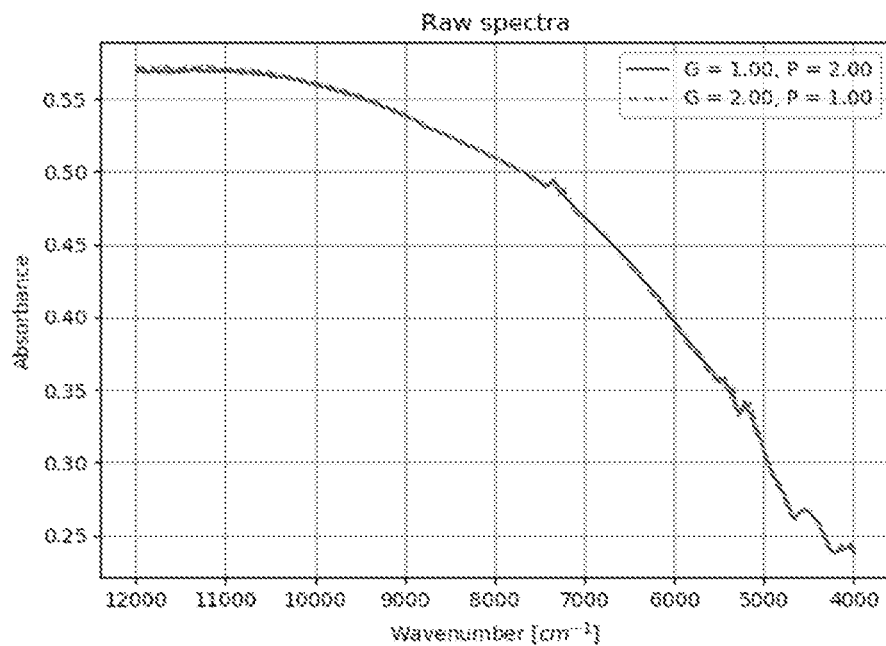
FIGS. 10A through 10D are graph illustrations of the relationship of infrared (IR) light intensity (obtained from cement samples) as a function of IR wavelength, and their derivatives.
Figure 10B:
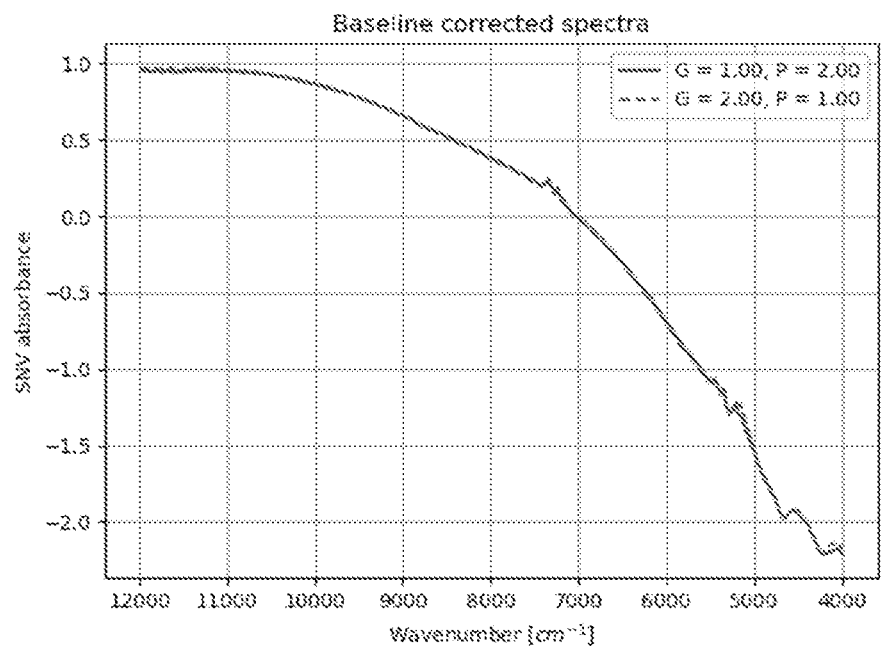
Figure 10C:
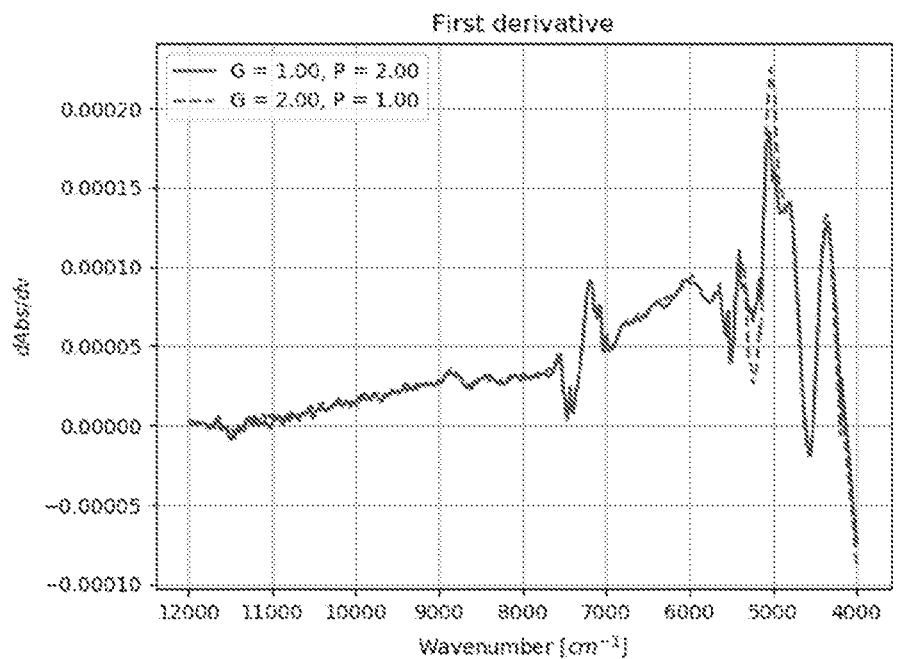
Figure 10D:
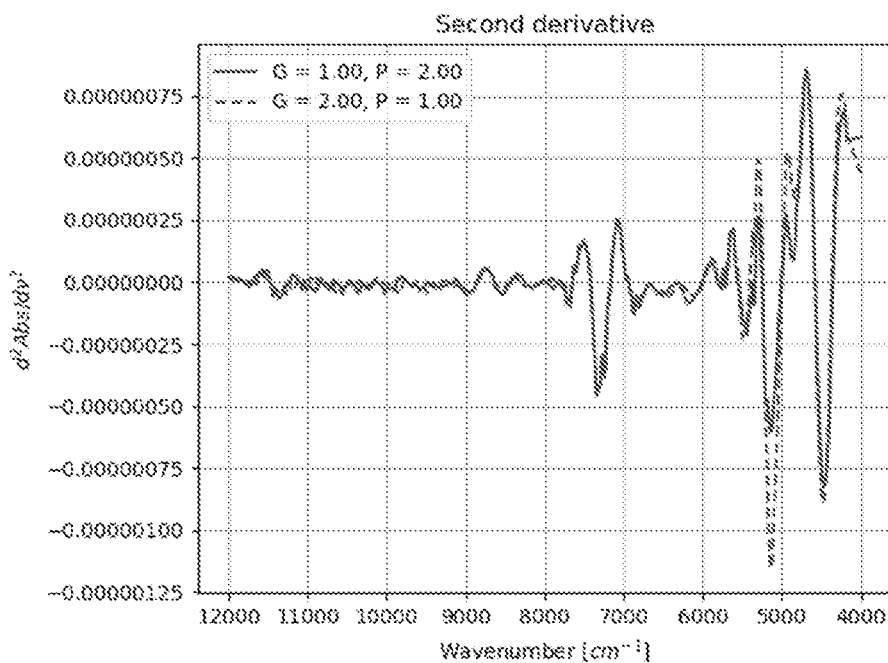

An example of an NIR signal is shown in FIGS. 10A-D. A raw signal is given in FIG. 10A over a wavenumber range between 4000 and 12000 $cm^{-1}$. The raw intensity is reported. In FIG. 10B, a standard, normal variate transformation is applied to normalize the baseline. In FIGS. 10C and 10D, the first and second derivatives are given respectively. In the generation of predictive models, one or more of these signals can be used as inputs for the model.

Based on the NIR signal, properties of the finished cement can be determined using lookup tables or correlation functions. These correlation functions or models can be generated using several standard techniques including multiple linear regression, multivariate regression, principal component regression, partial least squares regression, machine learning or other methods. For example, a well-known technique used to develop NIR correlations (to species concentrations), is partial least squares regression (PLS). See e.g., Wold, S.; Sjostrom, M.; Eriksson, L. (2001). "PLS-regression: a basic tool of chemometrics". Chemometrics and Intelligent Laboratory Systems. 58 (2): 109-130, and U.S. Pat. No. 5,475,220, which is specific to cement phase analysis. Other approaches may involve for example, Fourier transforms (see, e.g. McClure, W. F.; Hamid, A.; Giesbrecht, F. G.; Weeks, W. W.; (1984). "Fourier analysis enhances NIR diffuse reflectance spectroscopy." Applied Spectroscopy. 38 (3): 322-328), and machine learning methods (See e.g., Borin A.; Ferrão M. F.; Mello C.; Maretto D. A.; Poppi R. J.; (2006). "Least-squares support vector machines and near infrared spectroscopy for quantification of common adulterants in powdered milk." Analytica Chimica Acta. 579 (1): 25-32).

These models or lookup tables are constructed by obtaining NIR signals from multiple cement samples and measuring the desired property of interest (e.g. strength or setting time) for the corresponding hydrated cement samples (in the case of strength, for example) or unhydrated samples (in the case of a fineness parameter or pre-hydration, for example). As association is then made between the NIR signal and the property of interest, allowing the property to be predicted just from the NIR signal.

In addition to the predicted properties from the received NIR signals on the finished cement, the LD signal is used to determine a fineness characteristic of the cement (e.g. specific surface area, mean particle size, fraction below a certain sieve size, etc.). See e.g. the Insitec particle size analyzers commercially available from Malvern. This fineness characteristic is more preferably obtained from the NIR signal.

Based on the predictions from the NIR and LD signals, the finished cement produced can be adjusted towards one or more desired targets. For example, a finished cement may require to meet both a Delta target and strength target. Although maximum targets can be specified, in general, a balance of multiple properties is desired, which may not be the optimum for any one property. More desirable may be a consistent cement product. Thus, for example, a Delta of 2 hours with a strength of 42.5 MPa may be a target for a given finished cement.

The target can be assigned in multiple ways depending on the cement producer's preferences or needs. For example, a cement producer may be producing a cement with a certain class of strength (e.g. class 42.5 (minimum strength of 42.5 MPa, maximum strength of 62.5 MPa at the age of 28 days). Targets for Delta can also be determined using standards such as ASTM C563-17 tests or equivalent. In these cases, it is possible to use sulfate contents corresponding to the strength or calorimetry results and combine these data with NIR signals of the corresponding cement (the NIR signals obtained before hydrating the cement). The inventors have found that the optimum Delta, (i.e. the Delta corresponding to the highest strength) can be predicted based on the NIR signals. This provides an enormous advantage as both the target Delta and the current Delta (with a given amount of sulfate added) can be predicted in real-time. Currently, there is no method to provide a real-time optimum Delta. Still, the cement producer may also tailor, for example, their Delta to the region or market that they are selling to. In warmer climates a higher temperature may lower the solubility of plaster. If plaster has been used to control rapid aluminate reaction a sulfate deficiency may result. Furthermore, the reactivity of the aluminates increase, which can greatly increase the susceptibility to flash setting or extended set. Therefore, the cement producer may want an increased Delta. As another example, if the cement producer's market typically produce cement which is later combined with high volumes of class C fly ash, an increased Delta may also be desired to avoid common flash setting or extended set with class C fly ash (as the fly ash contributes more aluminate to the overall cementitious system without enough sulfate to balance). Or, the cement producer may decide to make an adjustment to the NIR-predicted optimum Delta. In other words, as the NIR-predicted optimum may indicate the Delta required to optimize strength, the producer may want to increase the Delta by, for example, 1 hour from this optimum Delta in order to account for the region (e.g. a warmer climate where the Delta will be reduced) or market (e.g. where fly ash is frequently added to the concrete and will supply extra aluminate that will lead to a reduced Delta). Targets may also be assigned to meet other related constraints, such as cost, carbon dioxide emissions, workability retention, admixture response, achievement of required early strength without exceeding statutory maximum strength, etc.

Figure 11:
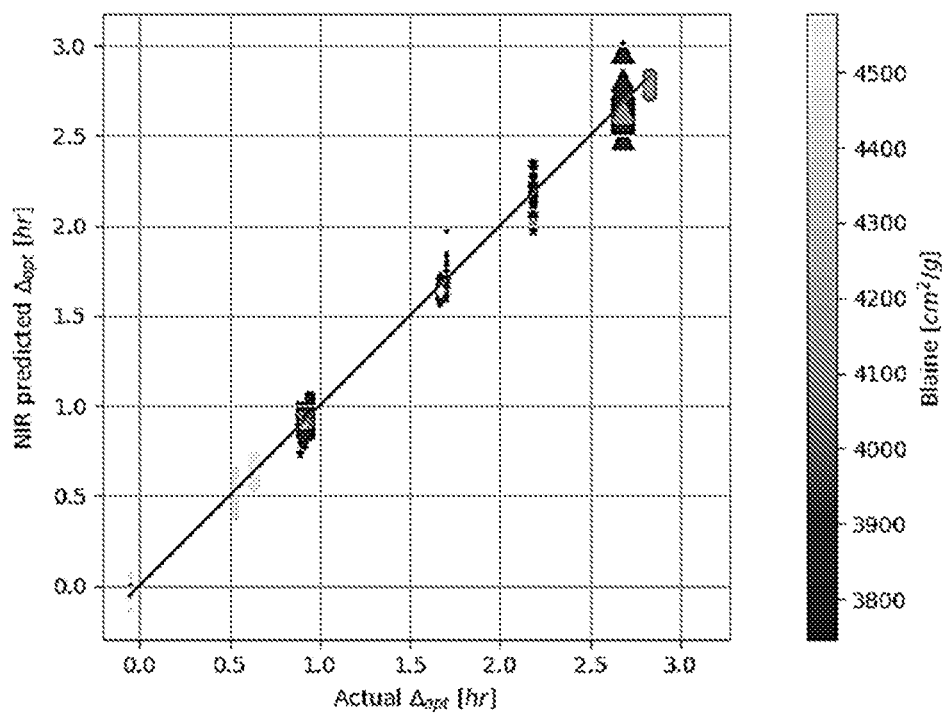
FIG. 11 is a graph illustration demonstrating the prediction accuracy of a model that receives an NIR signal spectra and that provides a predicted optimum Delta value, wherein the data plot confirms a one-to-one correlation (illustrated by the solid straight line) across a wide range of clinker chemistries and Blaine specific surface areas.

In FIG. 11, optimum Delta values predicted based on NIR signals are compared to actual measured optimum Delta values on the corresponding cements. Ten individual clinkers were crushed in a laboratory ball mill. Each crushed clinker was then blended with various levels of gypsum and plaster. For each blend, an NIR signal was obtained using a Bruker MATRIX-F FT-NIR spectrometer. Output signals similar to those in FIGS. 10A through 10D were obtained. In addition, for each blend, a mortar specimen was created according to EN-196-1:2016, which includes mixing with a standard sand sample and water to cement ratio. Various properties such as workability, air, strength, and Delta were obtained. Delta values were obtained through analysis of heat flow curves generated by a TAM® Air calorimeter, generating output signals similar to those of FIGS. 5A through 5E. In order to develop the NIR output signal—optimum Delta relationship shown in FIG. 11, the maximum strength (in this example, the compressive strength after 1 day) was determined for a set of crushed clinker with different sulfate levels, each with a different, measured Delta. The optimum Delta, therefore, corresponds to the maximum strength attained. This optimum Delta is valid for a given clinker (which was produced at a given instance in time). Data sets including the NIR output signals and the measured optimum Delta values were partitioned into cross-validation sets, using a repeated-stratified K-fold method. For each set, a partial least-squares (PLS) model was fit to a training partition, and validated on the remaining data (the testing partition). In implementing the PLS model, the number of components yielding the best fit according to the average accuracy over all the cross-validation sets was chosen. This PLS was then applied to all of the data and the fit is shown in FIG. 11. In FIG. 11, the predicted optimum Delta is plotted against the actual measured optimum Delta, with the solid line representing a one-to-one relationship. For this particular model, applied over 432 points, over 91% of the predicted values were within 0.5 hours of the actual measured values. Note that this prediction is valid over a large range of clinker chemistries and physical properties (e.g. Blaine specific surface area).

In addition to targets given for Delta and strength based on, for example, NIR predictions or fineness characteristics, ancillary limits can be provided to prevent certain processes from leading to suboptimal cement properties or mill conditions. For example, a maximum and minimum gypsum feeder rate, or rates of change of such feeder rate can be established. Likewise, limits on the water spray and ventilation fan speed can be enforced. Because the relationships between for example the water spray, pre-hydration level, and gypsum dehydration can be complex, limiting the process can limit unexpected interaction issues (e.g. the water spray rate or the cement cooler may affect both temperature and moisture in the mill). These limits can help to prevent runaway conditions where catastrophic results may occur.

Figure 12:
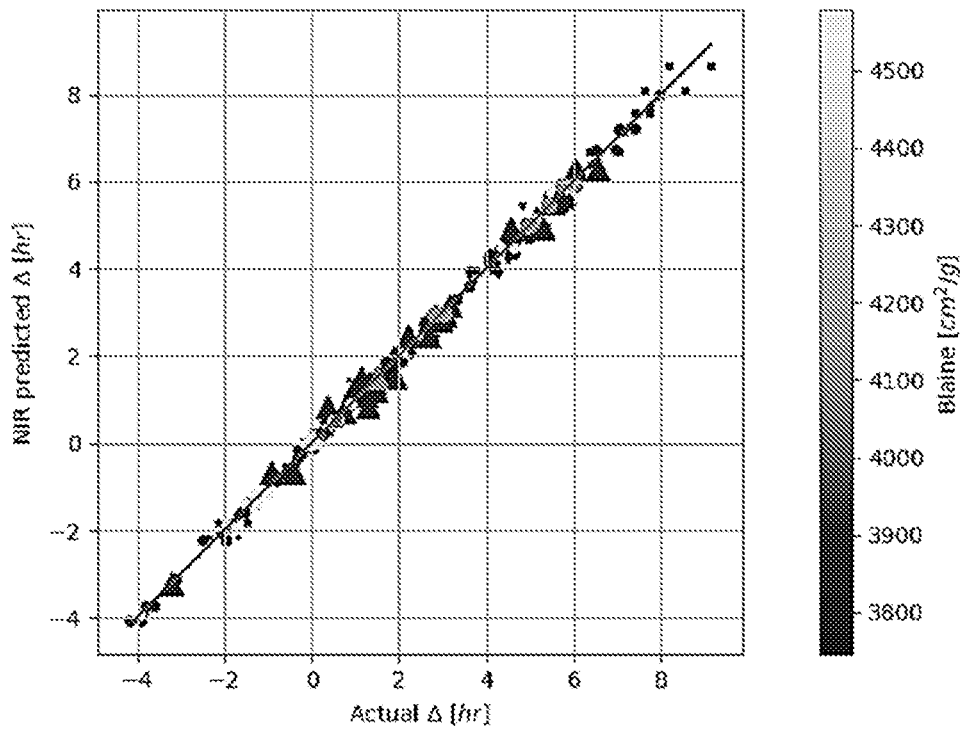
FIG. 12 is a graph illustration demonstrating the prediction accuracy of a model that receives an NIR signal spectra and that provides a predicted Delta value, wherein the data plot confirms a one-to-one correlation (illustrated by the solid straight line) across a wide range of clinker chemistries and Blaine specific surface areas.

In order to achieve the targets, predictions of both Delta and strength may be determined. In FIG. 12, Delta values predicted based on NIR signals are compared to actual measured Delta values on the corresponding cements. The model was generated using the same cement sets that the optimum Delta was calculated from, which again includes ten individual clinkers. For this particular model, applied over 365 points representing ten individual clinkers, 98% of the data was predicted within 0.5 hour of the actual measured value. Note that this has been performed over a very wide range of clinker chemistries (represented by the shape of the data point), sulfate levels and Blaine specific surface areas (represented by the shade of the data point) and surprisingly has shown a very high accuracy. It is expected that within a given plant, the range of both clinker chemistries and specific surface areas will be narrower than the data used to generate FIG. 12, which may lead to improvements in accuracy. Thus, based on the prediction, a current Delta value of the finished cement can be determined. Based on a deviation from the target, several different options can be taken. For example, in the event that the Delta is greater than the target, the sulfate content can be reduced. The amount of reduction can be determined based on a predetermined relationship between a sulfate dose and Delta. However a more preferred method is to make a small adjustment in the sulfate content (in this case a reduction) that is large enough to be detected by the NIR signal, but small enough not to cause a catastrophic change in the cement properties (i.e. to avoid under- or over-dosing). After the change has been made, another NIR signal and prediction can be executed to measure the deviation of the Delta with respect to the target. This process can be repeated until the Delta is within a predefined distance from the target. A similar process can be performed if the Delta is less than the target (e.g. the sulfate source can be incrementally increased). Moreover, the invention allows not only the total sulfate, but the amounts of gypsum and plaster to be adjusted. The plaster content is not as straightforward as adding or subtracting the sulfate source because there are cases where a given total sulfate content is required along with a specific gypsum to plaster ratio. In these cases, changes to the mill processing parameters can be performed, thus affecting the amount of gypsum dehydration to plaster. For example, if the gypsum/plaster ratio is to be decreased, the temperature in the mill can be increased and/or the water spray rate can be decreased. However, the mill system is complex and this action may affect pre-hydration or other factors affecting strength. It is with such system complexities that a real-time measurement of both Delta and strength enables true control.

As another method of control, an evolutionary optimization scheme can be implemented. Evolutionary optimization is an artificial intelligence algorithm inspired by biological evolution. Related to the present invention, small actions, which may be random, are taken to introduce a change to the cement production process. Measurements are made (through the use of NIR, for example) to determine the effects of the small actions. Because measurements can be made in real-time, many small actions can be taken. Each action and measurement is recorded and the algorithm begins to learn the best way to optimize toward a pre-defined goal, for example to achieve a strength target of 42.5 MPa and a Delta of 2 hours. This method provides an advantage over a traditional optimization method, since traditional methods rely on understanding accurate relationship between actions and the changes measured (e.g. increasing Blaine and achieving a certain change in strength as measured by NIR). Because of the complexity of the system, understanding both the relationships and the interaction effects (e.g. changes in Delta as they affect changes in strength and vice versa) is very difficult.

Figure 13:
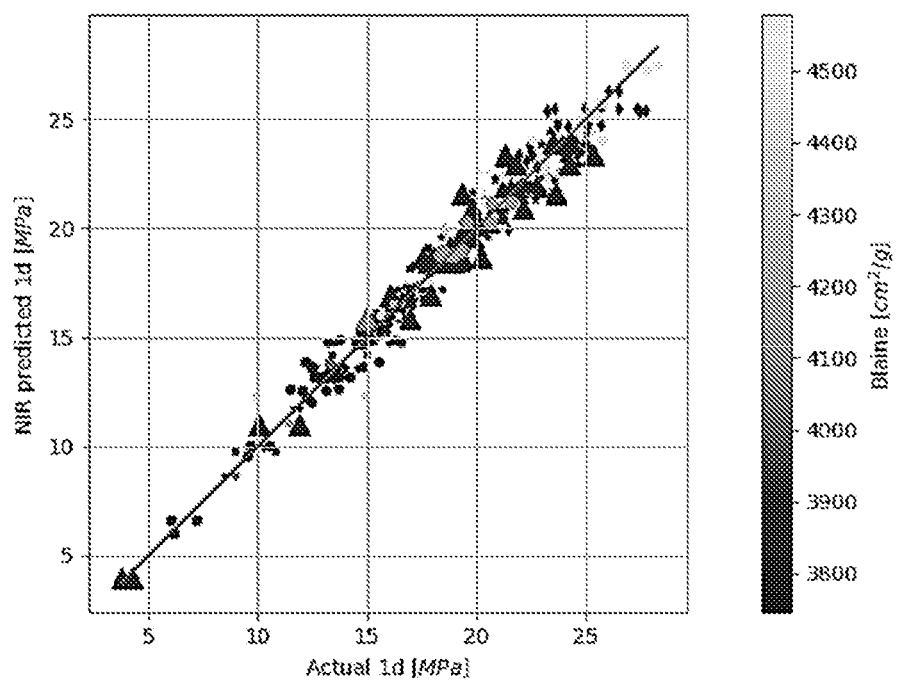
FIG. 13 is a graph illustration demonstrating the prediction accuracy of a model that receives an NIR signal spectra and outputs a predicted 1 day strength value, wherein the data plot confirms a one-to-one correlation (illustrated by the solid straight line) across a wide range of clinker chemistries and Blaine specific surface areas.

As a second example, in FIG. 13, strength values predicted based on NIR signals are compared to actual measured strength values on corresponding cements. The model was generated using the same cement sets that the Delta was calculated from, which again includes ten individual clinkers. In this case, after the PLS model was generated (in the same fashion as described above), 77% of the predicted values fall within 5% of the actual measured strength. This is a surprisingly high degree of accuracy considering that the correlation function used to make the prediction was developed using a wide range of clinker chemistries (represented as the shape of the data point) and Blaine specific surface areas (represented as the shade of the data point). It is expected that when the range of variation in the clinker and cement properties is lower, as would be expected when only measuring the cement made from a single plant using clinker from the same kiln, the accuracy should improve. This is supported by FIG. 14, which shows that the accuracy is higher when only one clinker source is considered, at similar Blaine specific areas (98% of the predicted values fall within 5% of the actual measured strength). To the inventors' knowledge, a direct relationship between strength and NIR signals has not previously been demonstrated.

Figure 14:
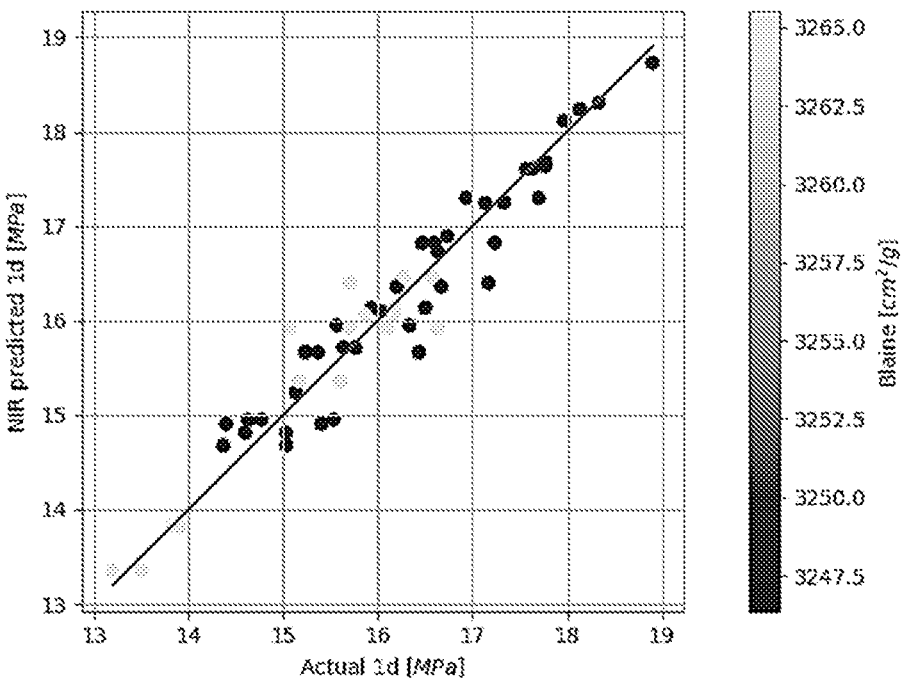
FIG. 14 is a graph illustration demonstrating the improved prediction accuracy of a model that receives an NIR signal spectra and outputs a predicted 1 day strength value, wherein the data confirms a one-to-one correlation (illustrated by the solid straight line) for a single clinker chemistry.

With a strength prediction as shown in FIG. 13 or 14, not only can the deviation from a target strength be determined, but the change in strength relative to the Delta can also be determined. Thus, an iterative approach is possible where both the predicted Delta and strength are constantly monitored in conjunction with other possible measured parameters, and adjusted, leading to an understanding of how optimum Delta varies with other factors. The present invention enables this on a frequency basis on the order of minutes, which is of the same order of magnitude as the cement residence time in the mill. Furthermore, this also enables each adjustment (to one or more parameters/processes) to be of small increment, because the application of online sensors allow prediction of both Delta and strength a multiplicity of times over a short period of minutes, strengthening the statistical confidence in the direction of performance change brought about by said small adjustment. Having confidence in the result of the adjustment, further adjustments can be made. Such a method allows a rapid iterative process to accommodate changes in the clinker, sulfate source, SCM, additive performance, etc. This is a distinct improvement over what is available to cement producers today. For example, if a cement producer were today using calorimetry to control to a pre-determined optimum Delta, the Delta could be known at best every 8-16 hours (depending on when the Delta actually occurs in the cement). This has two distinct disadvantages. Firstly, the clinker, sulfate source or SCM composition, cement fineness, and other properties may well have changed in the 12 hours since the cement sample was collected, so the adjustment indicated by the calorimetry test may no longer be the correct or optimal one. In other words, the target or optimal Delta is assumed to be constant for a clinker even though the chemistry of the clinker, sulfate source, or SCM, or fineness of the cement has changed, thus possibly resulting in a change of the optimal Delta. Secondly, if the calorimetry indicates that Delta is far off from the optimal value, then this means that sub-optimal cement has been produced for the past 12 hours. In the case of optimizing and adjusting based on strength measurements, this problem is even worse, since, by definition, it requires at least 24 hours to obtain a 1-day strength measurement.

Moreover, when considering management of more than one parameter (in this case, strength and Delta), the inability for real-time monitoring in current practice makes the control even more difficult. For example, in order to adjust Delta, a calorimetry test must be performed, which takes 8 hours at minimum. After the result is received, an adjustment is made for example, to the sulfate feed rate. After this has occurred, another sample must be taken to determine the effect on strength. This test takes 24 hours. If an adjustment is made to strength, then the Delta must be rechecked, which takes another 8 hours. Thus, a complete "cycle" of adjustments takes 40 hours with the current technology. In 40 hours, for instance, 4000 MT of cement can be made, and as was stated in the previous paragraph, it is possible that the composition of the clinker, sulfate source or SCM has already changed. Further, due to the long lead-time, larger changes must be made, with increased risk that it is not in the right direction. A real-time measure and manage system applied iteratively circumvents these issues and allows the cement producer to produce a consistent product.

A real-time solution is especially necessary if changes are made outside of the mill, i.e. in the kiln. Based on the chemistry of the clinker as determined by an NIR sensor on the cement produced, or on the stream of clinker entering the mill, it may be desirable to make changes to the raw material ratios into the kiln. This would be much less advantageous if accomplished at intervals of 8 or more hours (i.e. as is possible with calorimetry today). Aside from changes in the kiln raw meal, changes in the processing can also be done based on clinker and finished sample monitoring.

During the classification of the cement within the classifier (236 of FIG. 9), coarse particles are recirculated back to the mill (238) while finer particles are transferred to the cement silo (250) as finished cement (244). In block 106 of FIG. 8, a LD signal from the recirculated portion can be obtained. Based on this signal, a fineness characteristic can be calculated, which, when combined with a fineness characteristic of the finished cement, can be used to determine how to change the particle size distribution of the finished cement. Control of the classifier includes several methods: air speed, volume loading, etc. Based on the combined LD signals, one method may be more preferential than another. Alternatively, an NIR sensor can replace or augment the LD sensor to also provide a fineness characteristic.

It is also envisioned that an acoustic sensor that monitors the grinding mill can provide information to the filling (of steel balls) of the mill. This information may be useful for particle size adjustments.

Figure 15:
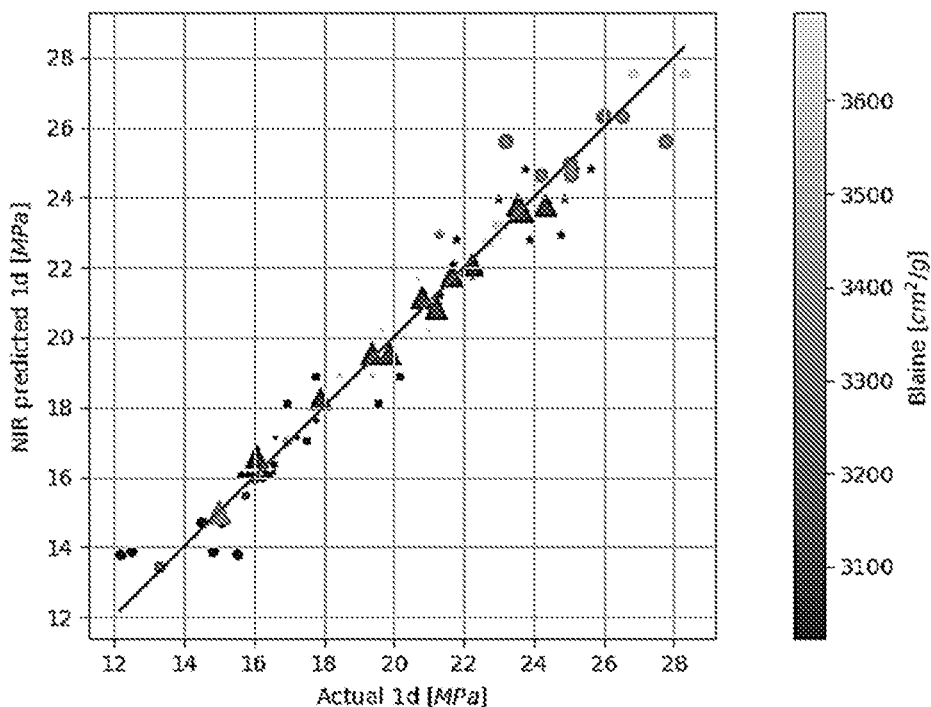
FIG. 15 is a graph illustration demonstrating the improved prediction accuracy of a model that receives an NIR signal spectra and outputs a predicted 1 day strength value, wherein the Delta is between 1.5 and 2.5 hours, and, furthermore, wherein the data plot confirms a one-to-one correlation (illustrated by the solid straight line).

Another beneficial feature enabled by real-time monitoring and management of the cement process is the ability to selectively make certain properties constant. This is an advantage from a modeling point of view, as predictions can become more accurate. For example, in FIG. 15, Delta was held constant while strength was predicted. Compared to FIG. 13, the cross-validation accuracy improved 6 percentage points. Thus, it may be advantageous to first adjust the Delta to the desired target and then adjust strength (iteratively). Alternatively, the Blaine specific surface area can be held constant (or at least the variation can be minimized through a closed-loop control system, for example). In this case, again, the improvement in the strength prediction can be demonstrated.

In block 108 of FIG. 8, a temperature (T), moisture (M) or relative humidity (RH) sensor (or a combination thereof) (234 or 254 of FIG. 9) can be used to give an indication of the gypsum dehydration. This information can be used to correct for the dehydration by adjusting the sulfate feed rate or other mill processes (e.g. water spray) to adjust the ratio between gypsum and plaster. An NIR sensor can also be used to determine the temperature, moisture or relative humidity or even the dehydration rate directly. Similarly, in block 108 of FIG. 8, the conduit (e.g. belt or air slide) between the mill and the silo can be instrumented with T, M, RH sensors or a combination thereof (234 of FIG. 9), or the cement cooler between the mill and the silo to monitor the dehydration during the transportation to the mill. And finally, the same type of sensors can be instrumented in the silo itself (250) to provide correction factors due to the dehydration, as shown in block 108 of FIG. 8. Again, an NIR sensor can be used to collect similar information.

Aside from gypsum dehydration, it is envisioned by the inventors that pre-hydration can also be predicted from T, M, RH or NIR sensors readings in these same locations.

The performance of cement additives depends on sulfate type and content (gypsum, hemihydrate, anhydrite), on cement fineness and on the degree of cement pre-hydration. Therefore, modifications on the type and dosage of the cement additive need to consider the advantages and disadvantages of changing other factors. The next four examples illustrate some of these relationships.

Cement additives can affect Delta. A reduction in Delta may happen when ingredients that chelate aluminum (such as alkanolamines or sugars) are present in the cement additive. A higher sulfate content can ensure Delta is within the preferred range for maximum strength. Adapting to a Delta or to a compressive strength target may therefore involve changing the composition of the cement additive and/or adjusting the content of sulfate.

Figure 16:
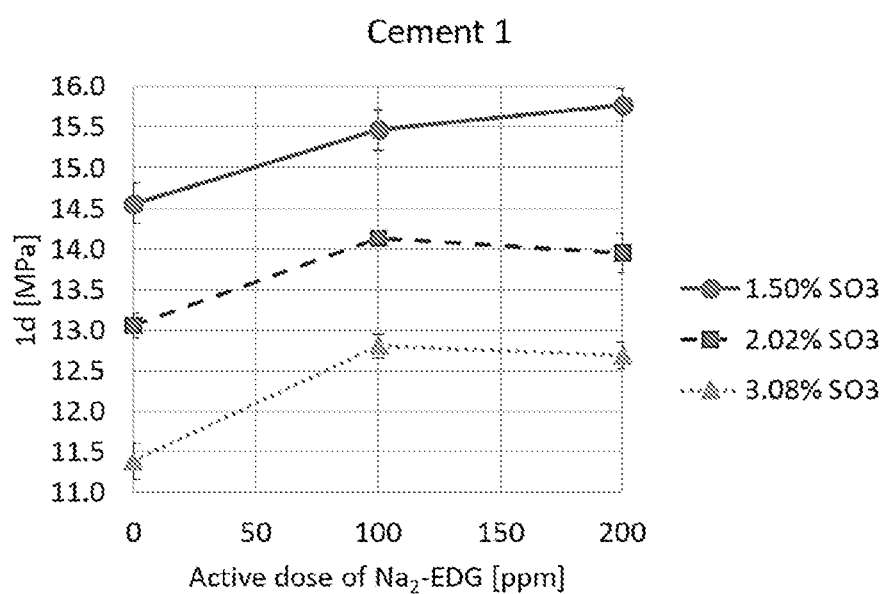
FIG. 16 is a graph illustration demonstrating the compressive strength response of Cement 1 sulfated at three different levels and exposed to four levels of a cement additive comprising $Na_2$-EDG.

FIG. 16 shows the compressive strength at 1 day of EN-196-1:2016 mortars prepared with a cement ground in the laboratory using an industrial ASTM C 150 type II/V clinker as a function of the active dose of disodium ethanol diglycinate ($Na_2$-EDG; dose in ppm of cement) and the added content of $SO_3$ (as gypsum and plaster). 3325 grams of crushed clinker were ground with 63.5 grams of gypsum and 39.4 grams of plaster in a laboratory ball mill to a Blaine specific surface area of 3,400 cm2/g to produce an initial cement with 1.50% $SO_3$. The $SO_3$ weight ratio of this grind is 1:0.74 gypsum:plaster). The two other levels of $SO_3$ (2.02% and 3.08%) were obtained by dry blending gypsum and plaster in the same $SO_3$ weight ratio as the initial cement prior to the mortar mixing. The graph shows that there is 1.5-2.0 MPa strength decrease of for every level of $SO_3$ added and the performance trend of $Na_2$-EDG is independent of the changes in $SO_3$ content in the range tested.

Figure 17:
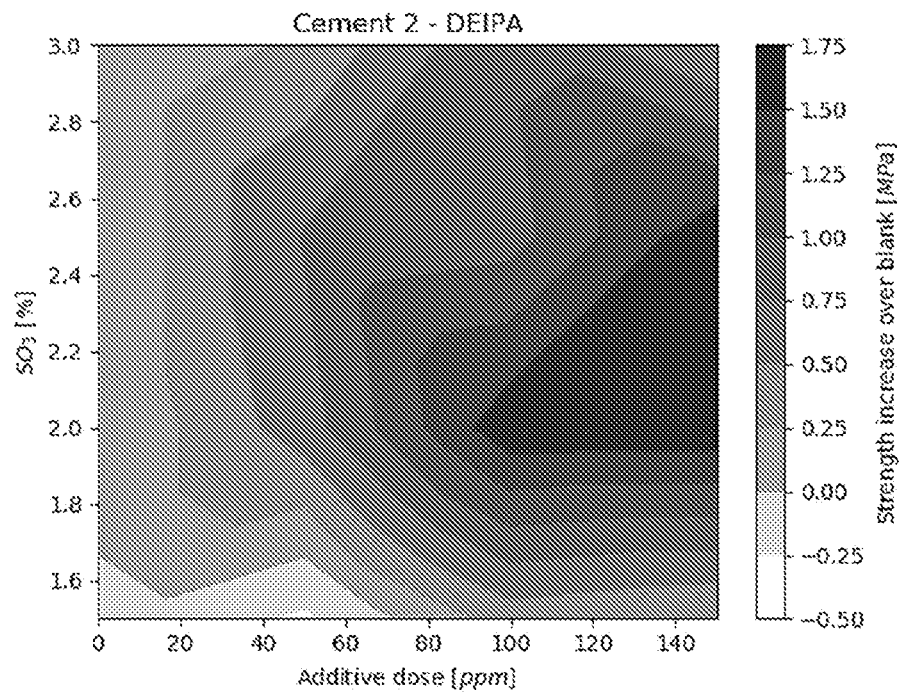
FIG. 17 is a graph illustration demonstrating the compressive strength response of Cement 2 sulfated at two different levels and exposed to four levels of a cement additive comprising DEIPA.
Figure 18:
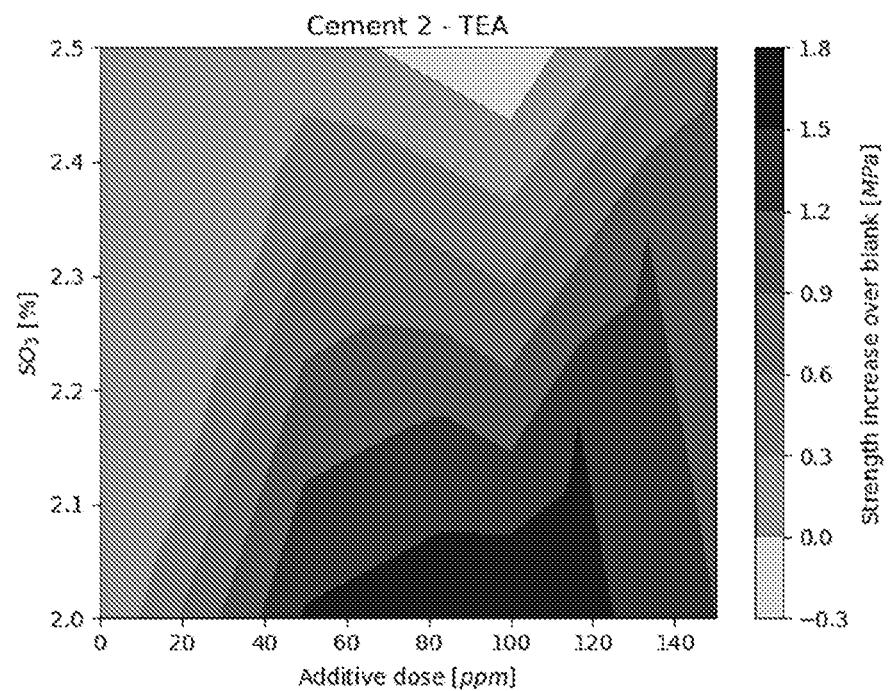
FIG. 18 is a graph illustration demonstrating the compressive strength response of Cement 3 sulfated at two different levels and exposed to four levels of a cement additive comprising DEIPA.
Figure 19:
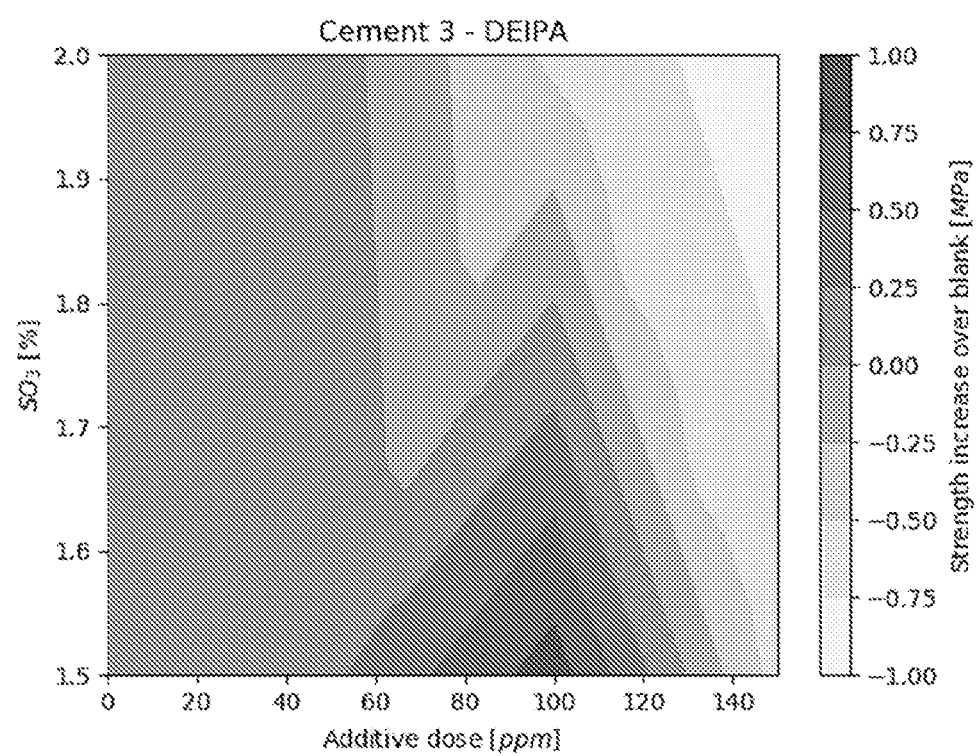
FIG. 19 is a graph illustration demonstrating the compressive strength response of Cement 4 sulfated at two different levels and exposed to four levels of a cement additive comprising DEIPA.

In the next example, FIGS. 17, 18 and 19 show the compressive strength at 1 day of EN-196 mortars prepared with cements ground in the laboratory using industrial ASTM C 150 type I or I/II clinkers as a function of both the active dose of different additives in ppm of cement and $SO_3$. The strength response is represented as a contour plot. To produce these samples, 3325 grams of crushed clinker were ground in a laboratory ball mill to a Blaine specific surface area of either 3,300 or 4,300 cm2/g without any source of calcium sulfate. The levels of $SO_3$ tested for each clinker were obtained by dry blending gypsum and plaster to the ground cement prior to the mortar mixing.

FIGS. 17 and 18 compare two different additives (diethanol isopropanolamine (DEIPA), and triethanol amine (TEA)) within the same cement. The contour plots in FIGS. 17 and 18 demonstrate the complexity of the additive efficiency, as it depends on both the additive dosage and the sulfate content for Cement 2. The present invention can ensure that the proper ranges of both are satisfied to maximize efficiency of the additive. In FIG. 19, DEIPA is added to a different cement (Cement 3). In comparing FIGS. 17 and 19, it is demonstrated that the response is different depending on the cement. Thus, in order to optimize additives for properties such as strength, real-time sulfate and strength predictions based on for example, and NIR signal, can help to determine optimal additive dosages. For example, adjustments can be made to move the system in a certain sulfate range.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Skilled artisans can make variations and changes without departing from the spirit of the invention.

It is claimed:

1. A method for manufacturing cement, comprising:
   (A) introducing, into a grinding mill, raw materials comprising clinker, a source of sulfate chosen from gypsum, plaster, calcium anhydrite, or a mixture thereof; grinding the raw materials, to produce a ground blend of particles comprising ground clinker and calcium sulfate; and separating the ground blend of particles within a classifier whereby a first portion of the particles or the finished cement is removed from the grinding mill and whereby a second portion of the particles is recirculated for further grinding in the grinding mill;
   (B) providing at least one sensor system comprising a processor that is communicative with processor-accessible memory, the at least one sensor system chosen from infrared sensor system, laser diffraction sensor system, or both, and detecting emanation, reflectance, transmittance, or absorption of energy by or through the ground blend of particles or finished cement provided in step (A), and generating output signals corresponding to the detected energy;
   (C) comparing, using the processor, the output signals generated in step (B) to data stored in the processor-accessible memory, the stored data comprising output signal values previously obtained from sensors measuring the emanation, reflectance, transmittance, or absorption of energy in the infrared spectrum, laser diffraction spectrum, or in both the infrared and laser diffraction spectrums, the stored data being correlated with a physical or chemical property of the corresponding finished cement, hydrated cement, or cementitious product made with the cement; and
   (D) in response to the comparison in step (C), adjusting a grinding mill condition chosen from (i) adjusting amount and form of calcium sulfate introduced into the grinding mill in step (A); (ii) adjusting classifier settings thereby to change relative amounts of ground particles being removed from the grinding mill and being recirculated back into the grinding mill; (iii) adjusting amount, type, or both amount and type of cement additives introduced into the grinding mill; (iv) adjusting amount of water being introduced into the grinding mill; (v) adjusting amount of air provided by adjusting power or speed of a fan or blower connected to ventilate the mill; (vi) adjusting amount or type of supplemental cementitious material introduced into the grinding mill; or (vii) performing a combination of the foregoing adjustments of grinding mill conditions.

2. The method of claim 1 wherein steps (A) through (D) are performed and repeated on at least a monthly basis or at shorter time intervals.

3. The method of claim 1 wherein steps (A) through (D) are performed and repeated for at least successive 100,000 metric tons (MT) of cement clinker being ground in the grinding mill or at shorter volume intervals.

4. The method of claim 1 wherein steps (A) through (D) are performed and repeated upon a detected change in the cement production process.

5. The method of claim 1 wherein, in step (A), the processor is programmed to adjust sulfate entering the mill in terms of calcium sulfate type, feed rate, or both type and feed rate.

6. The method of claim 1 wherein the processor is programmed to adjust supplementary cementitious materials (SCM) entering the mill in terms of type, feed rate, or both type and feed rate.

7. The method of claim 1 wherein the processor is programmed to adjust the introduction of chemical additives into the grinding mill in terms of type, formulation, amounts, dosage rate, or a combination thereof.

8. The method of claim 1 wherein the processor is programmed to adjust a kiln process, a mill process or both.

9. The method of claim 1 further comprising collecting data from at least one non-IR, non-laser sensor disposed or located within, or at the inlet or outlet of: (i) the grinding mill, (ii) an air flow inlet, outlet, or channel connected to grinding mill, or (iii) a kiln that produces cement clinker material introduced into the grinding mill.

10. The method of claim 1 further comprising providing an IR or laser sensor within an elevator bucket, conveyor belt, air slide, or pneumatic conveying device within or connected to the grinding mill.

11. The method of claim 1 wherein, in step (C), the data stored is correlated with a physical or chemical property of finished or hydrated cement, which physical or chemical property is chosen from (i) strength test data, (ii) exothermic data; (iii) set initiation data; (iv) slump data; (v) dimensional stability data; (vi) air content data; (vii) prehydration data; (viii) reduction or burn conditions data; (ix) cement fineness data; or (x) a mixture thereof.

12. The method of claim 1 wherein, in step (B), the at least one sensor system is an infrared sensor system having an infrared emitter to irradiate the ground blend of particles or finished cement and an infrared sensor to detect infrared radiation (IR) reflected from the irradiated ground blend of particles or finished cement, the infrared sensor system thereby obtaining reflected IR data; and, in step (C), the processor compares the reflected IR data with stored reflected IR data corresponding to strength test data of hydrated ground blend of particles or finished cement at a predetermined age.

13. The method of claim 1 wherein, in step (B), the at least one sensor system is an infrared sensor system having an infrared emitter to irradiate the ground blend of particles or finished cement and an infrared sensor to detect infrared radiation (IR) reflected from the irradiated ground blend of particles or finished cement, the infrared sensor system thereby obtaining reflected IR data; and, in step (C), the processor compares the reflected IR data with stored reflected IR data corresponding to exothermic data stored in processor-accessible memory.

14. The method of claim 1 wherein, in step (C), the stored reflected IR data corresponds to exothermic data comprising calorimetric measurements of hydrating ground finished cement; the method further comprising:

determining whether the difference between the time $T_2$ minus time $T_1$ is less than (−)1 hours or greater than (+)4 hours, where $T_1$ represents the time at which maximum silicate reaction rate occurs after initiation of cement hydration and $T_2$ represents the time after initiation of cement hydration at which either the renewed tricalcium aluminate reaction rate occurs (if after $T_1$) or at which the aluminate reaction is completed (if occurring before $T_1$); and if the difference of $T_2$ minus $T_1$ is less than (−)1 hours or greater than (+)4 hours, adjusting the amount of gypsum, plaster, calcium anhydrite or a combination thereof within the sulfate source introduced into the grinding mill, adjusting the sulfate feed rate into the mill.

15. The method of claim 14 further comprising adjusting amount of water introduced into the mill, power or speed of a fan or blower connected to ventilate the mill, amount of additive or additives introduced into the grinding mill; or a combination thereof.

16. The method of claim 1 wherein, in step (C), the stored reflected IR data corresponds to exothermic data comprising calorimetric measurements of hydrating ground finished cement; the method further comprising:

determining whether the difference between the time $T_2$ minus time $T_1$ is less than the predefined target minus 1 hour or greater than the predefined target plus 2 hour, where $T_1$ represents the time at which maximum silicate reaction rate occurs after initiation of cement hydration and $T_2$ represents the time after initiation of cement hydration at which either the renewed tricalcium aluminate reaction rate occurs if after $T_1$ or at which the aluminate reaction is completed if occurring before $T_1$; and if the difference is less than the predefined target minus 1 hour or greater than the predefined target plus 2 hours, adjusting a grinding mill condition chosen from (i) amount, form or both amount and form of calcium sulfate introduced into the grinding mill; (ii) classifier settings, thereby to change relative amounts of ground particles being sent to the silo and being recirculated back into the grinding mill; (iii) amount, type, or both amount and type of cement additives introduced into the grinding mill; (iv) amount of water being introduced into the grinding mill; (v) amount of air provided by adjusting power or speed of a fan or blower connected to ventilate the mill; (vi) amount or type of supplemental cementitious material introduced into the grinding mill; (vii) cement cooler setting, thereby to change the temperature of the finished cement or (viii) a combination thereof.

17. The method of claim 1 wherein, in step (C), the method further comprises comparing sensor data taken from step (B) to at least two different stored processor-accessible data sets.

18. The method of claim 1 further comprising measuring the particle size of the clinker and calcium sulfate being ground in the grinding mill; and, in further response to the step (C) comparison between the obtained reflected IR data and the stored reflected IR, adjusting a particle size characteristic or property of the clinker and calcium sulfate being ground, or both.

19. The method of claim 1 further comprising the steps of calculating a value corresponding to degree or level of prehydration of the cement, incorporating the value into processor-accessible memory, and initiating decision whether to adjust at least one of the grinding mill or recirculation conditions, and, if the decision to adjust grinding mill or recirculation conditions is initiated, adjusting at least one of the grinding mill or recirculation conditions.

20. The method of claim 1 wherein, in step (B), the at least one energy radiation/sensor system is an infrared sensor system having an infrared emitter to irradiate the ground blend of particles or finished cement and an infrared sensor to detect infrared radiation (IR) reflected from the irradiated ground blend of particles or finished cement, the infrared sensor system thereby obtaining reflected IR data; and, in step (C), the processor comparing the reflected IR data with stored reflected IR data corresponding to test result data, and indicating on a monitor display, by print out, or by visual or audible alarm indicating the degree of reduction in the clinker or otherwise that a pre-established threshold of clinker reduction has been met or exceeded.

21. The method of claim 1 further comprising introducing into the grinding mill and into the raw materials at least one cement additive.

22. The method of claim 21 further comprising adjusting amount, type, or both amount and type of the at least one cement additive introduced into the grinding mill.

23. A system for manufacturing cement, comprising:

a grinding mill for grinding raw materials including clinker, a source of sulfate chosen from gypsum, plaster, calcium anhydrite, or a mixture thereof to produce a ground blend of particles comprising ground clinker and calcium sulfate;

a classifier for separating the ground blend of particles whereby a first portion of the particles or the finished cement is removed from the grinding mill and whereby a second portion of the particles is recirculated for further grinding in the grinding mill;

at least one sensor system comprising a processor that is communicative with processor-accessible memory, the at least one sensor system chosen from infrared sensor system, laser diffraction sensor system, or both, the sensor system detecting emanation, reflectance, transmittance, or absorption of energy by or through the ground blend of particles or finished cement, and the sensor system effective for generating output signals corresponding to the detected energy; and the processor configured or programmed to compare output signals generated by the at least one sensor system with data stored in the processor-accessible memory, the stored data comprising output signal values previously obtained from sensors measuring the emanation, reflectance, transmittance, or absorption of energy in the infrared spectrum, laser diffraction spectrum, or in both the infrared and laser diffraction spectrums; and the processor further configured or programmed to perform an adjustment chosen from (i) adjusting amount and form of calcium sulfate introduced into the grinding mill (ii) adjusting the classifier settings thereby to change relative amounts of ground particles being removed from the grinding mill and being recirculated back into the grinding mill; (iii) adjusting amount, type, or both amount and type of cement additives introduced into the grinding mill; (iv) adjusting amount of water being introduced into the grinding mill; (v) adjusting the amount of air provided by adjusting power or speed of a fan or blower connected to ventilate the mill; (vi) adjusting amount or type of supplemental cementitious material introduced into the grinding mill; (vii) performing a combination of the foregoing adjustments of grinding mill conditions.

24. The system of claim 23 further comprising introducing at least one cement additive to the raw materials being ground.

25. The system of claim 24 wherein the processor is further programed to adjust amount, type, or both amount and type of cement additive introduced into the grinding mill.

26. A method for manufacturing cement, comprising:
(A) introducing, into a grinding mill, raw materials comprising clinker, a source of sulfate chosen from gypsum, plaster, calcium anhydrite, or a mixture thereof, and at least one cement additive; grinding the raw materials, to produce a ground blend of particles comprising ground clinker and calcium sulfate and the at least one cement additive; and separating the ground blend of particles comprising the ground clinker, calcium sulfate, and the at least one cement additive, within a classifier whereby a first portion of the particles or the finished cement is removed from the grinding mill and whereby a second portion of the particles is recirculated for further grinding in the grinding mill;

(B) providing at least one sensor system comprising a processor that is communicative with processor-accessible memory, the at least one sensor system chosen from infrared sensor system, laser diffraction sensor system, or both, and detecting emanation, reflectance, transmittance, or absorption of energy by or through the ground blend of particles or finished cement comprising the ground clinker, calcium sulfate, and the at least one cement additive, as provided in step (A), and generating output signals corresponding to the detected energy;

(C) comparing, using the processor, the output signals generated in step (B) to data stored in the processor-accessible memory, the stored data comprising output signal values previously obtained from sensors measuring the emanation, reflectance, transmittance, or absorption of energy in the infrared spectrum, laser diffraction spectrum, or in both the infrared and laser diffraction spectrums, the stored data being correlated with a physical or chemical property of the corresponding finished cement, hydrated cement, or cementitious product comprising the ground clinker, calcium sulfate, and the at least one cement additive; and (D) in response to the comparison in step (C), adjusting amount, type, or both amount and type of the at least one cement additive introduced into the grinding mill.

27. The method of claim 26 further comprising, in Step (D) response to the comparison in step (C), adjusting a grinding mill condition chosen from adjusting the amount and form of calcium sulfate introduced into the grinding mill in step (A); adjusting classifier settings thereby to change relative amounts of ground particles being removed from the grinding mill and being recirculated for further grinding in the grinding mill; adjusting amount of water being introduced into the grinding mill; adjusting amount of air provided by adjusting power or speed of a fan or blower connected to ventilate the mill; adjusting amount or type of supplemental cementitious material introduced into the grinding mill; or performing a combination of the foregoing adjustments of grinding mill conditions.

* * * * *